US012486524B2

(12) United States Patent
Hwang et al.

(10) Patent No.: US 12,486,524 B2

(45) Date of Patent: Dec. 2, 2025

(54) METHODS OF CULTURING A MAMMALIAN CELL

(71) Applicant: Genzyme Corporation, Cambridge, MA (US)

(72) Inventors: Christopher Hwang, Cambridge, MA (US); Timothy Johnson, Cambridge, MA (US); Jason Walther, Cambridge, MA (US); Cheng Cheng, Cambridge, MA (US); Jonathan Wang, Cambridge, MA (US); Neha Shah, Cambridge, MA (US); Seul-A Bae, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/572,978

(22) Filed: Jan. 11, 2022

(65) Prior Publication Data

US 2022/0145348 A1 May 12, 2022

Related U.S. Application Data

(62) Division of application No. 14/976,486, filed on Dec. 21, 2015, now Pat. No. 11,306,341.

(60) Provisional application No. 62/095,734, filed on Dec. 22, 2014.

(51) Int. Cl.

*C12P 21/00* (2006.01)
*C07K 16/00* (2006.01)
*C12N 5/00* (2006.01)

(52) U.S. Cl.

CPC .............. *C12P 21/00* (2013.01); *C07K 16/00* (2013.01); *C12N 5/0043* (2013.01); *C12N 5/005* (2013.01); *C07K 2317/14* (2013.01); *C12N 2500/50* (2013.01); *C12N 2510/02* (2013.01)

(58) Field of Classification Search

None

See application file for complete search history.

(56) References Cited

U.S. PATENT DOCUMENTS

| | | | |
|---|---|---|---|
| 4,522,811 A | 6/1985 | Eppestein et al. | |
| 5,721,121 A | 2/1998 | Etcheverry et al. | |
| 6,458,571 B1 | 10/2002 | Seiden | |
| 6,458,574 B1 | 10/2002 | Selden et al. | |
| 6,974,681 B1 | 12/2005 | McGrew | |
| 8,765,415 B2 * | 7/2014 | Arunakumari | C12P 21/02 435/71.1 |
| 8,911,964 B2 | 12/2014 | Pla et al. | |
| 9,260,695 B2 | 2/2016 | Crowley et al. | |
| 11,306,341 B2 | 4/2022 | Hwang et al. | |
| 11,702,628 B2 | 7/2023 | Wang et al. | |
| 2003/0113915 A1 | 6/2003 | Heidemann et al. | |
| 2005/0186669 A1 | 8/2005 | Ho et al. | |
| 2005/0272124 A1 | 12/2005 | Chen et al. | |
| 2008/0199958 A1 | 8/2008 | Hui | |
| 2008/0206819 A1 * | 8/2008 | Tsao | C12N 5/0018 435/70.1 |
| 2009/0233334 A1 | 9/2009 | Hildinger et al. | |
| 2011/0020929 A1 | 1/2011 | Schober et al. | |
| 2011/0053265 A1 | 3/2011 | Follstad et al. | |
| 2012/0164066 A1 | 6/2012 | Greene et al. | |
| 2014/0154726 A1 | 6/2014 | Yang et al. | |
| 2014/0255994 A1 | 9/2014 | Konstantinov et al. | |
| 2014/0271633 A1 | 9/2014 | Hossler | |
| 2014/0273206 A1 | 9/2014 | Jin et al. | |
| 2015/0158907 A1 | 6/2015 | Zhou et al. | |
| 2015/0183821 A1 | 7/2015 | Konstantinov et al. | |
| 2015/0202595 A1 | 7/2015 | Godawat et al. | |
| 2015/0203529 A1 | 7/2015 | Godawat et al. | |
| 2015/0203531 A1 | 7/2015 | Godawat et al. | |
| 2015/0203532 A1 | 7/2015 | Godawat et al. | |
| 2015/0232505 A1 | 8/2015 | Konstantinov et al. | |
| 2015/0353896 A1 | 12/2015 | Bruninghaus et al. | |
| 2016/0002594 A1 | 1/2016 | Yang et al. | |
| 2016/0017280 A1 | 1/2016 | Villiger-Oberbek et al. | |
| 2016/0017291 A1 | 1/2016 | Yang et al. | |
| 2016/0177361 A1 | 6/2016 | Hwang et al. | |
| 2019/0225934 A1 | 7/2019 | Pla et al. | |
| 2022/0333054 A1 | 10/2022 | Barrett et al. | |
| 2022/0340948 A1 | 10/2022 | Coffman et al. | |

FOREIGN PATENT DOCUMENTS

| | | |
|---|---|---|
| JP | 2011-507550 | 3/2011 |
| JP | 2014-221765 | 11/2014 |
| JP | 2017-519497 | 7/2017 |
| KR | 10-2011-0017233 | 2/2011 |

(Continued)

OTHER PUBLICATIONS

Tordhal et al ("Study of a perfusion process of Chinese hamster ovary cells by ATF filtration in bioreactor ovary cells by ATF filtration in bioreactor," Sep. 11, pp. 1-47 (Year: 2009).*

Sandadi et al Bioprocess Biosyst Eng 34:819-832 (Year: 2011).*

Peng et al Biotechnol. Prog, 30:1411-1418 (Year: 2014).*

Sieblist et al Biotechnol. Prog., 29:1278-1288 (Year: 2013).*

Qi et al Lindner-Olsson et al. (eds.), Animal Cell Technology: From Target to Market, 412-415, pp. 412-413 (Year: 2001).*

Clincke (Biotechnol. Prog., vol. 29, No. 3, 754-767 (Year: 2013).*

Narayanappa et al Biotechniques, 67 (2), 98-109 (Year: 2019).*

Tharmalingam Biotechnology & Engineering, 112: 832-837 (Year: 2015).*

Chalmer et al in ed Al-Rubeai (ed.), Animal Cell Culture, Cell Engineering 9, 163-183 , only 163-180 (Year: 2015).*

Office Action in Brazilian Patent Application No. BR112017013423-3, dated Sep. 22, 2022, 12 pages (with machine translation).

(Continued)

*Primary Examiner* — Anoop K Singh

(74) *Attorney, Agent, or Firm* — Fish & Richardson P.C.

(57) ABSTRACT

Provided herein are methods of culturing a mammalian cell in a liquid medium including poloxamer-188 at a concentration of 1.8 g/L or at a greater concentration than 1.8 g/L more or a liquid medium that includes a poloxamer-188 concentration that is selected based on one or more factors selected from the group of: pore size, pore type, gas flow rate, viable cell density in the medium, and markers related to cell stress.

5 Claims, 15 Drawing Sheets

(56) References Cited

FOREIGN PATENT DOCUMENTS

| | | | |
|---|---|---|---|
| WO | WO 2002/050251 | 6/2002 | |
| WO | WO 2002/101019 | 12/2002 | |
| WO | WO 2003/039459 | 5/2003 | |
| WO | WO 2006/033935 | 3/2006 | |
| WO | WO 2006/138143 | 12/2006 | |
| WO | WO 2008/106515 | 9/2008 | |
| WO | WO 2009/034186 | 3/2009 | |
| WO | WO 2009/061446 | 5/2009 | |
| WO | WO 2012/152945 | 11/2012 | |
| WO | WO 2013/116449 | 8/2013 | |
| WO | WO 2013/151616 | 10/2013 | |
| WO | WO 2014/066519 | 5/2014 | |
| WO | WO 2014/130864 | 8/2014 | |
| WO | WO 2014/130872 | 8/2014 | |
| WO | WO 2014/137903 | 9/2014 | |
| WO | WO 2014/143691 | 9/2014 | |
| WO | WO 2014/151901 | 9/2014 | |
| WO | WO 2014/194137 | 12/2014 | |
| WO | WO-2014194137 A1 * | 12/2014 | ............ A61K 47/10 |
| WO | WO 2015/039115 | 3/2015 | |
| WO | WO 2015/109146 | 7/2015 | |
| WO | WO 2015/109151 | 7/2015 | |
| WO | WO 2015/188009 | 12/2015 | |
| WO | WO 2015/188106 | 12/2015 | |
| WO | WO 2015/191462 | 12/2015 | |
| WO | WO 2021/058713 | 4/2021 | |

OTHER PUBLICATIONS

Office Action in Israeli Patent Application No. 253071, dated Apr. 30, 2023, 9 pages (with English translation).
Office Action in Russian Patent Application No. 2020101112, dated Jun. 7, 2023, 15 pages (with English translation).
Office Action in Brazilian Patent Application No. BR 122022026227.9, dated Mar. 6, 2023, 14 pages (with English machine translation).
Office Action in Canadian Patent Application No. 2,971,861, dated Oct. 25, 2022, 3 pages.
U.S. Appl. No. 14/061,657, filed Oct. 23, 2013, Yang et al.
U.S. Appl. No. 14/769,772, filed Aug. 21, 2015, Yang et al.
U.S. Appl. No. 14/769,783, filed Aug. 21, 2015, Jianguo et al.
U.S. Appl. No. 14/976,486, filed Dec. 21, 2016, Bae et al.
U.S. Appl. No. 62/009,058, filed Jun. 6, 2014, Villiger-Oberbek et al.
U.S. Appl. No. 62/095,734, filed Dec. 22, 2014, Bae et al.
Australian Office Action in Patent Application No. 2015369809, dated Mar. 15, 2021, 4 pages.
Barrett et al., "Microwell engineering characterization for mammalian cell culture process development," Biotechnol Bioeng., Feb. 1, 2010, 105(2):260-275.
Brazilian Office Action in Patent Application No. BR112017013423-3, dated Aug. 25, 2020, 5 pages.
Canadian Office Action in Patent Application No. 2,971,861, dated Nov. 2, 2021, 4 pages.
Chaturvedi et al., "Comparison of the behavior of CHO cells during cultivation in 24-square deep well microplates and conventional shake flask systems, " Biotechnology Reports, 2014, 1:22-26.
Chinese Office Action in Patent Application No. 201580076640.3, dated Dec. 26, 2019, 8 pages.
Chinese Office Action in Patent Application No. 201580076640.3, dated Jan. 21, 2020.
Chinese Office Action in Patent Application No. 201580076640.3, dated Jul. 7, 2020, 13 pages.
Chinese Office Action in Patent Application No. 201580076640.3, dated Nov. 2, 2020, 11 pages.
Clincke et al., "Very high density of CHO cells in perfusion by ATF or TFF in WAVE bioreactor Part I, Effect of the cell density on the process," Biotechnol. Prog May 2013, 29(3):754-767.
Costa et al., "The impact of microcarrier culture optimization on the glycosylation profile of a monoclonal antibody," Springer Plus, Jan. 28, 2013, 2(25):1-10.
Danielson et al., "Maximizing cell densities in miniprep-scale cultures with H15 medium and improved oxygen transfer," Biochemical Engineering J, 2004, 17:175-180.
De Jesus et al., "Tubespin satellites, A fast track approach for process development with animal cells using shaking technology," Biotechnology and Bioengineering Journal, 2004, 17:217-223.
European Communication in Patent Application No. 13786587.9, dated Sep. 27, 2016, 11 pages.
European Communication in Patent Application No. 15843061.1, dated Aug. 11, 2017, 2 pages.
European Communication in Patent Application No. 15843061.1, dated Jul. 1, 2019, 8 pages.
Fernandes-Platzgummer et al., "Scale-up of mouse embryonic stem cell expansion in stirred bioreactors," American Institute Chemical Engineers, Sep./Oct. 2011, 27(5):1421-1432.
Gargi, et al., "Development of a new bioprocess scheme using frozen seed train intermediates to initiate CHO cell culture manufacturing campaigns," Biotech. Bioeng., May 4, 2013, 110(5):1376-1385.
Gebauer et al., "Engineered protein scaffolds as next-generation antibody therapeutics," Curr Opin Chem Biol., Epub Jun. 6, 2009, 13(3):245-255.
Indian Office Action in Patent Application No. 201737025477, dated Nov. 22, 2020, 8 pages.
Invitation to Pay in International Application. No. PCT/US2015/034494, dated Aug. 12, 2015, 6 pages.
Israel Office Action in Patent Application No. 253071, dated Dec. 17, 2019.
Israel Office Action in Patent Application No. 253071, dated Feb. 15, 2021, 10 pages (with English translation).
Japanese Office Action in Patent Application No. 2017-533539, dated Feb. 2, 2021, 2 pages.
Japanese Office Action in Patent Application No. 2017-533539, dated Jun. 23, 2020, 9 pages.
Japanese Office Action in Patent Application No. 2017-533539, dated Nov. 26, 2019, 7 pages.
Japanese Office Action in Patent Application No. 2020-177700, dated Nov. 9, 2021, 10 pages (with English translation).
Katakam et al., "Effect of Surfactants on the physical stability of recombinant human growth hormone," Journal of Pharmaceutical Association, Jun. 1, 1995, 84(6):713-716.
Kim et al., "Batch, Fed-Batch and Microcarrier Cultures with CHO cell lines in a pressure-cycle driven miniaturized bioreactor," Biotechnology and Bioengineering, 2011, 109(1):137-145.
Mexican Office Action in Patent Application No. MX/a/2017/008338, dated Nov. 24, 2020, 8 pages.
Mexican Office Action in Patent Application No. MX/a/2017008338, dated Feb. 25, 2021, 6 pages (with English translation).
Nam et al., "The effects of microcarrier culture on recombinant CHO cells under biphasic hypothermic culture conditions," Cytotechnology, 59(2):81-91, Epub May 2, 2009.
Notification of Transmittal of the International Search Report and The Written Opinion issued in PCT/US2013/066410, on Jan. 31, 2014 (12 pages).
PCT International Preliminary Report on Patentability in International Appln. No. PCT/US2013/066410, dated May 7, 2015, 8 pages.
PCT International Preliminary Report on Patentability in International Appln. No. PCT/US2014/017785, dated Sep. 3, 2015, 8 pages.
PCT International Preliminary Report on Patentability in International Appln. No. PCT/US2014/017803, dated Aug. 25, 2015, 8 pages.
PCT International Preliminary Report on Patentability in International Appln. No. PCT/US2015/067040, 12 pages.
PCT International Search Report and Written Opinion in International Appln. No. PCT/US2014/017785, dated May 20, 2014, 11 pages.
PCT International Search Report and Written Opinion in International Appln. No. PCT/US2014/017803, dated May 20, 2014, 11 pages.

(56) References Cited

OTHER PUBLICATIONS

PCT International Search Report and Written Opinion in International Appln. No. PCT/US2015/034494, dated Nov. 30, 2015, 24 pages.
PCT International Search Report and Written Opinion in International Appln. No. PCT/US2015/034709, dated Oct. 30, 2015, 13 pages.
PCT International Search Report and Written Opinion in International Appln. No. PCT/US2015/067040, dated Sep. 5, 2016, 19 pages.
Peng et al., "Development of small scale cell culture models for screening poloxamer 188 lot-to-lot variation," Biotechnol Prog, 2014, 30:1411-1418.
Pohlscheidt et al., "Optimizing capacity utilization by large scale 3 000 L perfusion in seed train bioreactors," Biotech. Prog. 29(1): 2220229, Jan. 1, 2012.
Rodrigues et al., "Technological progresses in monoclonal antibody production systems," Biotechnol Prog., Mar.-Apr. 2010, 26(2):332-351.
Rosario, "Growth of Mesenchymal Stromal Cells in Automated Microwell Cultures, Influence of the Engineering Environment on Cell Growth Kinetics and Non-Directed Differentiation," Thesis submitted for the degree of Doctor of Philosophy, Sep. 1, 2008.
Russian Office Action in Patent Application No. 2017126045, dated Jun. 24, 2019, 4 pages.
Russian Office Action in Patent Application No. 2017126045, dated Nov. 12, 2019, 18 pages.
Scott, "Growth of mesenchymal stromal cells in automated microwell cultures: influence of the engineering environment on cell growth kinetics and non-directed differentiation," (Doctoral dissertation, UCL (University College London), 202 pages, Sep. 2008.
Silk et al., "Fed-batch operation of an industrial cell culture process in shaken microwells," Biotechnol Lett., 32(1):73-78, print Jan. 2010, Epub Sep. 17, 2009.
Singapore Written Opinion in Application No. 11201705103W, dated Dec. 2, 2019, 5 pages.
Singapore Written Opinion in Patent Application No. 11201506339R, dated Jul. 21, 2016.
Singapore Written Opinion in Patent Application No. 11201506343Q, dated Jun. 27, 2016, 5 pages.
Singapore Written Opinion in Patent Application No. 11201705103W, dated May 15, 2018, 7 pages.
Smelko et al., "Performance of high intensity fed-batch mammalian cell cultures in disposable bioreactor systems," Biotechnology Progress, Sep. 2011, 27(5):1358-1364.
Strnad et al., "Optimization of cultivation conditions in spin tubes for Chinese hamster ovary cells producing erythropoietin and the comparison of glycosylation patterns in different cultivation vessels," Biotechnology Progress, 26(3):653-663 (2010).
Taiwanese Office Action in Patent Application No. 104143177, dated Aug. 24, 2020, 8 pages.
Taiwanese Office Action in Patent Application No. 104143177, dated Feb. 22, 2021, 4 pages (with English translation).
Taiwanese Office Action in Patent Application No. 104143177, dated Feb. 4, 2020, 7 pages.
Taiwanese Office Action in Patent Application No. 104143177, dated Jun. 2, 2021, 6 pages (with English translation).
Tao et al., "Development and implementation of a perfusion-based high cell density cell banking process," Biotechnol. Prog., 2011, 27(3):824-829.
Tharmalingam et al., "Evaluating the Impact of High Pluronic F68 Concentrations on Antibody Producing CHO Cell Lines," Biotechnology and Bioengineering, Apr. 2015, vol. 11, No. 4, 832-837.
Tordahl et al., "Study of a perfusion process of Chinese hamster ovary cells by ATF filtration in bioreactor ovary cells by ATF filtration in bioreactor," Sep. 11, 2009.
USPTO Final Office Action issued in U.S. Appl. No. 14/976,486, dated Mar. 29, 2021, 12 pages.
USPTO Non-Final Office Action issued in U.S. Appl. No. 14/976,486, dated Sep. 18, 2020, 18 pages.
Villiger-Oberbek, Development and application of a high-throughout platform for perfusion-based cell culture processes, Journal of Biotechnology, 212, (2015) pp. 21-29.
Wright et al., "A novel seed-train process: using high-density cell banking, a disposable bioreactor, and perfusion technologies," BioProcessInt., Mar. 10, 2015 Supplement.
Yang et al., "Perfusion seed cultures improve biopharmaceutical fed-batch production capacity and product quality," Biotech. Prog. 30(3): 616-625, May 1, 2014.
Zhang et al., "A robust high-throughput sandwich cell-based drug screening platform," Biomaterials, Feb. 1, 2011, 32(4):1229-124.
Zhang et al., "Foaming and media surfactant effects on the cultivation of animal cells in stirred and sparged bioreactors," J Biotechnology, Dec. 31, 1992, pp. 289-306.
Office Action in Israel Patent Application No. 253071, dated Apr. 12, 2022, 5 pages (with English translation).
Moretto et al., "Process Raman Spectroscopy for In-Line CHO Cell Culture Monitoring," American Pharmaceutical Review, Apr. 2011, retrieved on Jun. 16, 2022, retrieved from URL <https://www.americanpharmaceuticalreview.com/Featured-Articles/37040-Process-Raman-Spectroscopy-for-In-Line-CHO-Cell-Culture-Monitoring/>, 9 pages.
Whelan et al., "In situ Raman spectroscopy for simultaneous monitoring of multiple process parameters in mammalian cell culture bioreactors," Biotechnology Progress, Sep./Oct. 2012, 28(5):1355-1362.
Office Action in European Patent Application No. 15843061.1, dated Jun. 22, 2022, 7 pages.
Office Action in Japanese Patent Application No. 2022-079207, dated Apr. 25, 2023, 17 pages (with English translation).
DeZengotita et al., "Effects of CO2 and osmolality on hybridoma cells: growth, metabolism and monoclonal antibody production," Cytotechnology, Sep. 1, 1998, 28(1-3):213-227.
International Search Report and Written Opinion in International Application No. PCT/US2022/024781, mailed on Jul. 11, 2022, 11 pages.
Kimura et al., "Effects of elevated pCO2 and/or osmolality on the growth and recombinant tPA production of CHO cells," Biotechnology and Bioengineering, Oct. 5, 1996, 52(1):152-160.
Office Action in Korean Patent Application No. 10-2017-7020466, dated Oct. 31, 2022, 9 pages (with English translation).
International Preliminary Report on Patentability in International Application No. PCT/US2022/024781, mailed on Oct. 26, 2023, 8 pages.
Office Action in Japanese Patent Application No. 2022-079207, dated Oct. 3, 2023, 12 pages (with English translation).
Office Action in U.S. Appl. No. 17/721,003, dated Nov. 30, 2023, 14 pages.
Office Action in Brazilian Patent Application No. BR122022026227-9, dated Jul. 18, 2023, 8 pages (with English translation).
Office Action in Indian Patent Application No. 201737025477, dated Jan. 5, 2024, 9 pages.
Office Action in Taiwanese Patent Application No. 110131996, dated Nov. 17, 2023, 12 pages (with English translation).
Chisti, "Animal-cell damage in sparged bioreactors," Trends in Biotechnology, Oct. 1, 2000, 18(10):420-432.
Ma et al., "Quantitative studies of cell-bubble interactions and cell damage at different Pluronic F-68 and cell concentrations," Biotechnology Progress, 2004, 20(4):1183-1191.
Michaels et al., "Analysis of cell-to-bubble attachment in sparged bioreactors in the presence of cell-protecting additives," Biotechnology and Bioengineering, Aug. 20, 1995, 47(4):407-419.
Office Action in Israeli Patent Application No. 308064, dated Jun. 5, 2024, 6 pages (with English translation).
Office Action in U.S. Appl. No. 17/721,003, dated Jul. 1, 2024, 27 pages.
Notice of Allowance in Australian Patent Application No. 2022204152, dated Nov. 12, 2024, 3 pages.
Office Action in Australian Patent Application No. 2022204152, dated Aug. 30, 2024, 2 pages.

(56) References Cited

OTHER PUBLICATIONS

Office Action in Canadian Patent Application No. 3,225,136, dated Jun. 19, 2025, 3 pages.

* cited by examiner

METHODS OF CULTURING A MAMMALIAN CELL

CROSS-REFERENCE TO RELATED APPLICATIONS

This application is a divisional application of U.S. patent application Ser. No. 14/976,486, filed Dec. 21, 2015, which claims priority to U.S. Provisional patent application Ser. No. 62/095,734, filed Dec. 22, 2014, the entire contents of which are herein incorporated by reference.

TECHNICAL FIELD

This invention relates to methods of biotechnology and the manufacturing of recombinant proteins.

BACKGROUND

Mammalian cells containing a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic protein drug substances.

SUMMARY

The present invention is based, at least in part, on the discovery that mammalian cells including a nucleic acid encoding a recombinant protein are viable and proliferate in culture media including poloxamer-188 at a concentration of 1.8 or at a greater concentration than 1.8 g/L (e.g., greater than 2.0 g/L, greater than 2.5 g/L, greater than 3.0 g/L, greater than 3.5 g/L, greater than 4.0 g/L, greater than 4.5 g/L, greater than 5.0 g/L, greater than 5.5 g/L, greater than 6.0 g/L, greater than 6.5 g/L, or greater than 7.0 g/L poloxamer-188), that optimal cell growth is achieved at a particular ratio of poloxamer-188 and antifoam, that high cell densities can be achieved by increasing poloxamer-188 concentration in the cell culture as a function of the viable cell density, and that the optimal poloxamer-188 concentration to be added to a cell culture in order to promote cell proliferation depends on one or more factors from the group of: pore size, pore type, gas flow rate, viable cell density in the medium, and markers related to cell stress.

Provided herein are methods of culturing a mammalian cell that include: perfusion culturing a mammalian cell comprising a recombinant protein-encoding nucleic acid under conditions sufficient to produce the recombinant protein, where perfusion culturing includes culturing in a liquid medium including poloxamer-188 at a concentration of 1.8 g/L or at a greater concentration than 1.8 g/L and where the poloxamer-188 is present in the medium and/or is added to the medium prior to the culturing step and/or is added to the medium during the culturing step. In some embodiments of any of the methods described herein, the medium includes poloxamer-188 at a concentration of 1.8 g/L or at a greater concentration that 1.8 g/L (e.g., at a concentration of 2.8 g/L or at a greater concentration that 2.8 g/L, at a concentration of 4.0 g/L or at a greater concentration than 4.0 g/L, at a concentration of 6.0 g/L or at a greater concentration that 6.0 g/L, at a concentration of 8.0 g/L or at a greater concentration than 8.0 g/L, or at a concentration of 10.0 g/L or at a greater concentration than 10.0 g/L).

In some embodiments of any of the methods described herein, the medium further includes antifoam and the ratio of antifoam (g/L) to poloxamer-188 (g/L) in the medium is between about 0.5% to about 6.0% (e.g., between about 1.0% to about 5.5%, or between about 1.5% to about 5.0%) in the liquid medium. In some embodiments of any of the methods described herein, the method includes adding poloxamer-188 to the medium prior to the culturing step and/or adding polaxamer-188 to the medium during the culturing step to provide in the medium poloxamer-188 at a concentration of 1.8 g/L or at a greater concentration than 1.8 g/L. In some embodiments of any of the methods provided herein, poloxamer-188 is present in the medium. In some embodiments of any of the methods described herein, the method includes adding poloxamer-188 to the medium prior to the culturing step and/or adding poloxamer-188 to the medium during the culturing step to provide in the medium poloxamer-188 at a concentration of 2.8 g/L or at a greater concentration than 2.8 g/L (e.g., at a concentration of 4.0 g/L or at a concentration of greater than 4.0 g/L, at a concentration of 6.0 g/L or at a greater concentration than 6.0 g/L, at a concentration of 8.0 g/L or at a greater concentration than 8.0 g/L, or at a concentration of 10.0 g/L or at a greater concentration than 10.0 g/L).

In some embodiments of any of the methods described herein, the method includes increasing the poloxamer-188 concentration in the medium over time. In some embodiments of any of the methods described herein, increasing the poloxamer-188 concentration in the medium over time is based on the viable cell density in the medium. In some embodiments of any of the methods described herein, the method includes increasing the poloxamer-188 concentration in the medium to greater than 1.8 g/L (e.g., between about 1.8 g/L to about 3.0 g/L, or between about 2.3 g/L to about 3.0 g/L), when the viable cell density in the medium is between about $35\times10^6$ cells/mL to about $60\times10^6$ cells/mL. In some embodiments of any of the methods described herein, the method includes increasing the poloxamer-188 concentration in the medium to greater than 3.0 g/L (e.g., between about 3.0 g/L to about 6.0 g/L, or between about 3.6 g/L to about 6.0 g/L), when the viable cell density in the medium is between about $60\times10^6$ cells/mL to about $90\times10^6$ cells/mL. In some embodiments of any of the methods described herein, the method includes increasing the poloxamer-188 concentration in the medium to greater than 6.0 g/L (e.g., greater than 7.0 g/L, greater than 8.0 g/L, or greater than 10.0 g/L), when the viable cell density in the medium is greater than $90\times10^6$ cells/mL. Some embodiments of any of the methods described herein include: increasing the poloxamer-188 concentration in the medium to between about 1.8 g/L to about 3.0 g/L when the viable cell density in the medium is between about $35\times10^6$ cells/mL to about $60\times10^6$ cells/mL; increasing the poloxamer-188 concentration in the medium to between about 3.0 g/L to about 6.0 g/L when the viable cell concentration density in the medium is between about $60\times10^6$ cells/mL to about $90\times10^6$ cells/mL; and increasing the poloxamer-188 concentration in the medium to greater than 6.0 g/L when the viable cell density concentration in the medium is greater than $90\times10^6$ cells/mL. Some embodiments of any of the methods described herein further include determining the viable cell density in the medium at one or more time points during the culturing.

In some embodiments of any of the methods described herein, the perfusion culturing includes: providing a vessel including mammalian cells disposed in a first liquid medium; incubating the vessel with agitation and for a culturing period of at least about 7 days at a temperature between about 32° C. to about 40° C.; and continuously or periodically after the first 48 to 96 hours of the culturing period removing a first volume of the first liquid medium and adding to the first liquid medium a second volume of a second liquid medium, wherein the first and second volumes are about equal. In some embodiments of any of the methods described herein, the second liquid medium includes poloxamer-188 at greater concentration than that in the first liquid medium. In some embodiments of any of the methods described herein, the first liquid medium includes poloxamer-188 at a concentration of 1.8 g/L or at a concentration less than 1.8 g/L, and the second liquid medium comprises poloxamer-188 at a greater concentration than 1.8 g/L (e.g., a greater concentration than 2.8 g/L, a greater concentration than 4.0 g/L, a greater concentration than 6.0 g/L, a greater concentration than 8.0 g/L, or a greater concentration than 10.0 g/L). In some embodiments of any of the methods described herein, the method includes, before or after adding the second volume of the second liquid medium to the first liquid medium, adding poloxamer-188 to the second liquid medium to provide in the second medium poloxamer-188 at a concentration of 1.8 g/L or at a greater concentration that 1.8 g/L (e.g., at a greater concentration than 2.8 g/L, at a greater concentration than 4.0 g/L, at a greater concentration than 6.0 g/L, at a greater concentration than 8.0 g/L, or at a greater concentration than 10.0 g/L).

Some embodiments of any of the methods described herein further include: collecting recombinant protein from the mammalian cells, from the first liquid medium, or the second liquid medium, or any combination thereof. Some embodiments of any of the methods described herein further include formulating the collected recombinant protein into a pharmaceutical composition. In some embodiments of any of the methods described herein, collecting is performed after the culturing achieves a viable cell density of greater than $30\times10^6$ cells/mL (e.g., greater than $50\times10^6$ cells/mL, greater than $100\times10^6$ cells/mL, greater than $150\times10^6$ cells/mL, or greater than $200\times10^6$ cells/mL).

Also provided herein are methods of culturing a mammalian cell that include: providing a culturing system including a vessel, a liquid medium disposed within the vessel, and a sparger disposed within the vessel including a plurality of pores configured to dispense gas through the sparger into the liquid medium; and perfusion culturing a mammalian cell including a recombinant protein-encoding nucleic acid in the culturing system under conditions and a gas flow rate sufficient to produce the recombinant protein in the system, wherein the medium includes a poloxamer-188 concentration that is selected based on one or more factors selected from the group of: pore size, pore type, gas flow rate, viable cell density in the medium, and markers related to cell stress. In some embodiments of any of the methods described herein, the selected poloxamer-188 concentration is achieved by adding poloxamer-188 to the medium prior to the culturing step and/or adding poloxamer-188 to the medium during the culturing step.

In some embodiments of any of the methods described herein, the factor is pore type and the pore type is a sintered pore or a drilled pore. In some embodiments of any of the methods described herein, the method includes selecting based on pore type and pore size, poloxamer-188 at a concentration of between about 2.3 g/L to about 3.3 g/L when the pore type is a drilled pore and the pore size is between about 750 μm to about 1.5 mm or poloxamer-188 at a concentration of between about 2.5 g/L to about 3.1 g/L when the pore type is a drilled pore and the pore size is between about 900 μm to about 1.1 mm. In some embodiments of any of the methods described herein, the method includes selecting based on pore type and pore size, poloxamer-188 at a concentration of between about 3.3 g/L to about 4.3 g/L when the pore type is a drilled pore and the pore size is between about 250 μm to about 750 μm or poloxamer-188 at a concentration of between about 3.5 g/L to about 4.1 g/L when the pore type is a drilled pore and the pore size is between about 400 μm to about 600 μm. In some embodiments of any of the methods described herein, the method includes selecting based on pore type and pore size, poloxamer-188 at a greater concentration than 4.3 g/L (e.g., at a greater concentration than 5.0 g/L, at a greater concentration than 6.0 g/L, at a greater concentration than 8.0 g/L, or at a greater concentration than 10.0 g/L) when the pore type is a drilled pore and the pore size is between about 1 μm to about 250 μm (e.g., between about 1 μm to about 200 μm, between about 160 μm to about 190 μm, or between about 170 μm to about 180 μm).

In some embodiments of any of the methods described herein, the method includes selecting based on pore type and pore size, poloxamer-188 at a concentration of between about 1.8 g/L to about 3.3 g/L when the pore type is a sintered pore and the pore size is greater than 150 μm. In some embodiments of any of the methods described herein, the method includes selecting based on pore type and pore size, poloxamer-188 at a concentration of between about 3.3 g/L to about 4.3 g/L when the pore type is a sintered pore and the pore size is between about 80 μm to about 150 μm or poloxamer-188 at a concentration of between about 3.5 g/L to about 4.1 g/L when the pore type is a sintered pore and the pore size is between about 90 μm to about 110 μm. In some embodiments of any of the methods described herein, the method includes selecting based on pore type and pore size, poloxamer-188 at a greater concentration than 4.5 g/L (e.g., at a greater concentration than 5.0 g/L, at a greater concentration than 6.0 g/L, at a greater concentration than 8.0 g/L, or at a greater concentration than 10.0 g/L), when the pore type is a sintered pore and the pore size is between about 1 μm to about 80 μm.

In some embodiments of any of the methods described herein, the perfusion culturing includes: incubating the culturing system including a first liquid medium with agitation and for a culturing period of at least about 7 days at a temperature between about 32° C. to about 40° C.; and continuously or periodically after the first 48 to 96 hours of the culturing period removing a first volume of the first liquid medium and adding to the first liquid medium a second volume of a second liquid medium. In some embodiments of any of the methods described herein, the second liquid medium includes poloxamer-188 at a greater concentration than the concentration of poloxamer-188 in the first liquid medium. In some embodiments of any of the methods described herein, the second medium includes the selected poloxamer-188 concentration.

Some embodiments of any of the methods described herein further include: collecting recombinant protein from the interior of the mammalian cells, from the first liquid medium, or the second liquid medium, or any combination thereof. Some embodiments of any of the methods described herein further include formulating the collected recombinant protein into a pharmaceutical composition.

In some embodiments of any of the methods described herein, the vessel is a perfusion bioreactor. In some embodiments of any of the methods described herein, the perfusion bioreactor has a volume between about 1.5 L to about 25,000 L. In some embodiments of any of the methods described herein the culturing period is greater than 10 days. In some embodiments of any of the methods described herein, removing the first volume of the first liquid medium and adding the second volume of the second liquid medium in (c) is performed continuously. In some embodiments of any of the methods described herein, removing the first volume of the first liquid medium and adding the second volume of the second liquid medium in (c) is performed periodically. In some embodiments of any of the methods described herein, the first volume of the first liquid medium removed and the second volume of the second liquid medium added in (c) are increased over time. In some embodiments of any of the methods described herein, the first liquid medium and/or second liquid medium is selected from the group of: a chemically-defined liquid culture medium, a serum-free liquid culture medium, a serum-containing liquid culture medium, an animal-derived component free liquid culture medium, and a protein-free medium. In some embodiments of any of the methods described herein, after about the first 48 to 96 hours of the period of time, in each 24-hour period, the first volume of the first liquid medium removed and the second volume of the second liquid medium added in (c) is about 0.3× to about 10× of the volume of the first liquid medium or the volume of the vessel.

In some embodiments of any of the methods described herein, the mammalian cell is a Chinese hamster ovary (CHO) cell, a human embryonic kidney (HEK) cell, an NSO cell, a baby hamster kidney (BHK) cell, a PerC6 cell, a Vero cell, or a HT-1080 cell line. In some embodiments of any of the methods described herein, the recombinant protein is an immunoglobulin, an enzyme, a growth factor, a protein fragment, or an engineered protein.

As used herein, the word "a" before a noun represents one or more of the particular noun. For example, the phrase "a mammalian cell" represents "one or more mammalian cells."

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated or undifferentiated cell. Non-limiting examples of mammalian cells are described herein. Additional examples of mammalian cells are known in the art.

The term "culturing" or "cell culturing" means the maintenance or proliferation of a mammalian cell under a controlled set of physical conditions.

The term "culture of mammalian cells," "culture," or "cell culture" means a liquid medium containing a plurality of mammalian cells that is maintained or proliferated under a controlled set of physical conditions.

The term "liquid culture medium" or "liquid medium" means a fluid that contains sufficient nutrients to allow a cell (e.g., a mammalian cell) to grow or proliferate in vitro. For example, a liquid medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid medium can contain serum from a mammal. In some embodiments, a liquid medium does not contain serum or another extract from a mammal (a defined liquid medium). In some embodiments, a liquid medium can contain trace metals, a mammalian growth hormone, and/or a mammalian growth factor. Another example of liquid medium is minimal medium (e.g., a medium containing only inorganic salts, a carbon source, and water). Non-limiting examples of liquid medium are described herein. Additional examples of liquid medium are known in the art and are commercially available. A liquid medium can contain any density of mammalian cells. For example, as used herein, a volume of liquid medium removed from a bioreactor can be substantially free of mammalian cells.

The term "animal-derived component free liquid culture medium" means a liquid medium that does not contain any components (e.g., proteins or serum) derived from a mammal.

The term "serum-free liquid culture medium" means a liquid medium that does not contain a mammalian serum. The term "serum-containing liquid culture medium" means a liquid medium that contains a mammalian serum.

The term "chemically-defined liquid culture medium" is a term of art and means a liquid medium in which all of the chemical components are known. For example, a chemically-defined liquid medium does not contain fetal bovine serum, bovine serum albumin, or human serum albumin, as these preparations typically contain a complex mix of albumins and lipids.

The term "protein-free liquid culture medium" means a liquid medium that does not contain any protein (e.g., any detectable protein).

The term "agitation" means stirring or otherwise moving a portion of liquid medium in a vessel. This is performed in order to, e.g., increase the dissolved $O_2$ concentration in the liquid medium in a bioreactor. Agitation can be performed using any art known method, e.g., an instrument or propellor. Exemplary devices and methods that can be used to perform agitation of a portion of the liquid medium in a bioreactor are known in the art.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a $F(ab')_2$ fragment, or a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art. A recombinant immunoglobulin can be produced using any of the methods described herein.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the methods described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence. A recombinant engineered protein can be produced using any of the methods described herein.

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid medium). Skilled practitioners will appreciate that a "secreted" protein need not dissociate entirely from the cell to be considered a secreted protein.

The term "perfusion bioreactor" means a bioreactor containing a plurality of cells (e.g., mammalian cells) in a first liquid medium, wherein the culturing of the cells present in the bioreactor includes periodic or continuous removal of the first liquid medium and at the same time or shortly thereafter adding substantially the same volume of a second liquid medium to the bioreactor. In some examples, there is an incremental change (e.g., increase or decrease) in the volume of the first liquid medium removed and added over incremental periods (e.g., an about 24-hour period, a period of between about 1 minute and about 24-hours, or a period of greater than 24 hours) during the culturing period (e.g., the liquid medium refeed rate on a daily basis). The fraction of media removed and replaced each day can vary depending on the particular cells being cultured, the initial seeding density, and the cell density at a particular time. "RV" or "reactor volume" means the volume of the liquid medium present at the beginning of the culturing process (e.g., the total volume of the liquid medium present after seeding).

The term "fed-batch bioreactor" is a term of art and means a bioreactor containing a plurality of cells (e.g., mammalian cells) in a first liquid medium, wherein the culturing of the cells present in the bioreactor includes the periodic or continuous addition of a second liquid medium to the first liquid medium without substantial or significant removal of the first liquid medium or second liquid medium from the cell culture. The second liquid medium can be the same as the first liquid medium. In some examples of fed-batch culture, the second liquid medium is a concentrated form of the first liquid medium. In some examples of fed-batch culture, the second liquid medium is added as a dry powder.

The term "sparger" is a term of art and means an apparatus having an inlet, a body, and a surface having one or more pores, where the inlet, the body, and the one or more pores are designed to allow for the flow of gas through the inlet, through the body, and out of the one or more pores. When spargers are used in a cell culture, one of the one or more pores is in contact with the cell culture, such that the gas flows out of the at least one pore and into the cell culture. Spargers are often described by their pore size and pore type. Non-limiting examples of spargers having different combinations of pore sizes and pore types are described herein.

The term "pore size" is a term of art and refers to the diameter of a single pore in a sparger having a single pore or an average diameter of two or more pores in a sparger having two or more pores.

The term "marker related to cell stress" is a term of art and means a biological molecule that is released by a cell under physiological stress (e.g., a cell undergoing necrotic cell death or apoptotic cell death) into the liquid medium or a biological molecule produced or having elevated levels in a cell under physiological stress (e.g., a cell undergoing necrotic cell death or apoptotic cell death). Non-limiting examples of markers related to cell stress that are released by a cell under physiological stress include proteases (e.g., activated caspases), lactate dehydrogenase, genomic DNA (e.g., nucleosomal DNA), cytochrome c, and activated PARP. Non-limiting examples of markers related to cell stress that are produced or have elevated levels in a cell under physiological stress include activated caspases, cytochrome c, activated PARP, and externalized phosphatidylserine.

"Specific productivity rate" or "SPR" is a term of art and as used herein refers to the mass or enzymatic activity of a recombinant protein produced per mammalian cell per day. The SPR for a recombinant therapeutic antibody is usually measured as mass/cell/day. The SPR for a recombinant therapeutic enzyme is usually measured as units/cell/day or (units/mass)/cell/day.

"Volume productivity rate" or "VPR" is a term of art and as used herein refers to the mass or enzymatic activity of recombinant protein produced per volume of culture (e.g., per L of bioreactor, vessel, or tube volume) per day. The VPR for a recombinant therapeutic antibody is usually measured as mass/L/day. The VPR for a recombinant therapeutic enzyme is usually measured as units/L/day or mass/L/day.

The phrases "poloxamer-188 at a concentration" and "poloxamer-188 concentration" are used interchangeably herein. The phrases "poloxamer-188 of X g/L or more" and "poloxamer-188 at a concentration of X g/L or at a greater concentration than X g/L" are used interchangeably herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

(triangles); and a perfusion cell culture run performed using a sparger with a drilled pore having a size of 500 pin and culture media that contain increasing amounts of poloxamer-188 over the length of the culture period (increasing from 1.8 g/L to 3.8 g/L) (filled circles).

Figure 12:
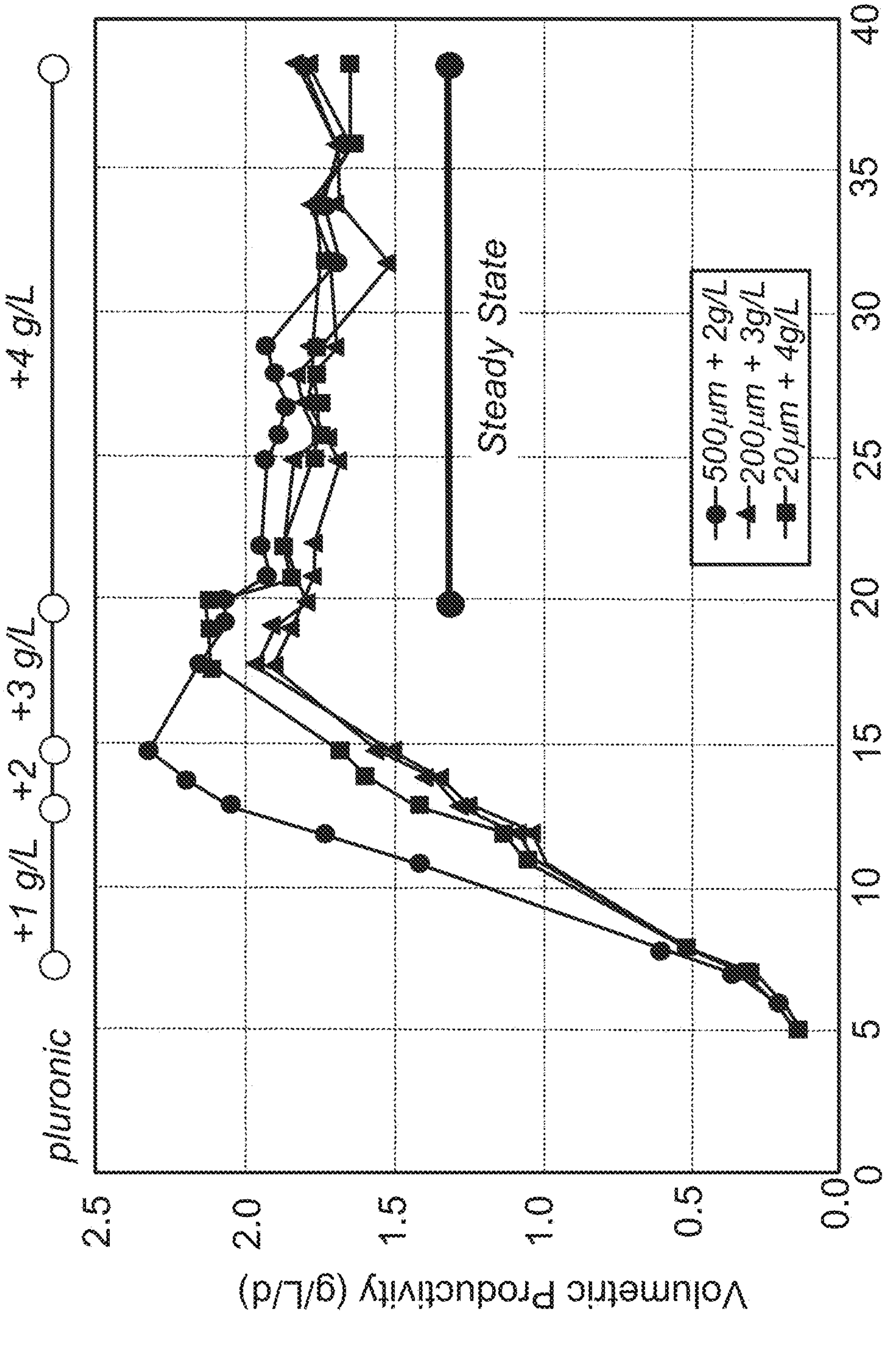

FIG. 12 is a graph of the volumetric productivity over time for a perfusion cell culture run performed using a sparger with a sintered pore having a size of 20 pin and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period) (triangles); and a perfusion cell culture run performed using a sparger with a drilled pore having a size of 500 μm and culture media that contain increasing amounts of poloxamer-188 over the length of the culture period (increasing from 1.8 g/L to 3.8 g/L) (circles).

Figure 13:
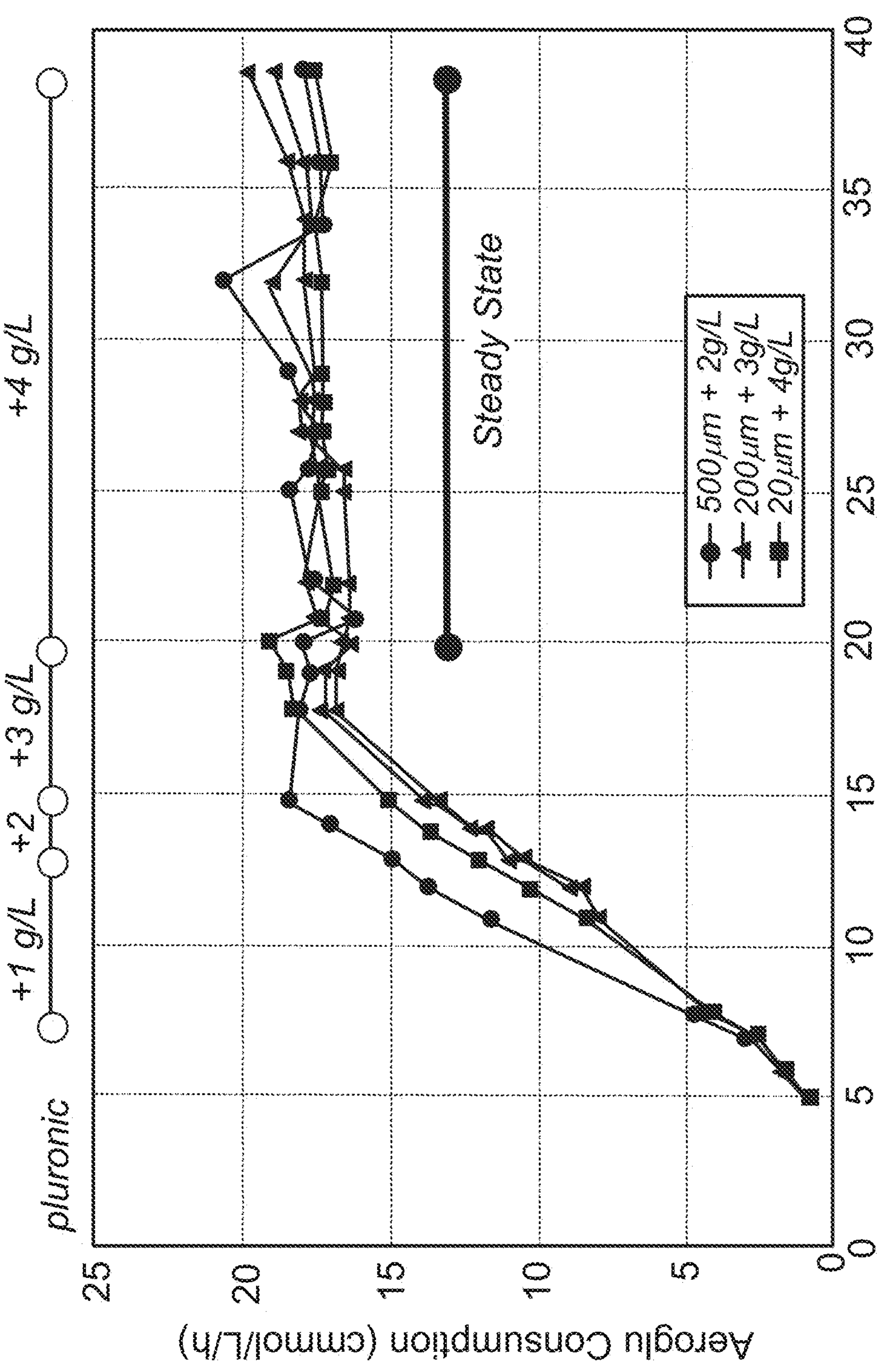

FIG. 13 is a graph of the aerobic glucose consumption over time for a perfusion cell culture run performed using a sparger with a sintered pore having a size of 20 μm and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period) (triangles); and a perfusion cell culture run performed using a sparger with a drilled pore having a size of 500 μm and culture media that contain increasing amounts of poloxamer-188 over the length of the culture period (increasing from 1.8 g/L to 3.8 g/L) (circles).

Figure 14:
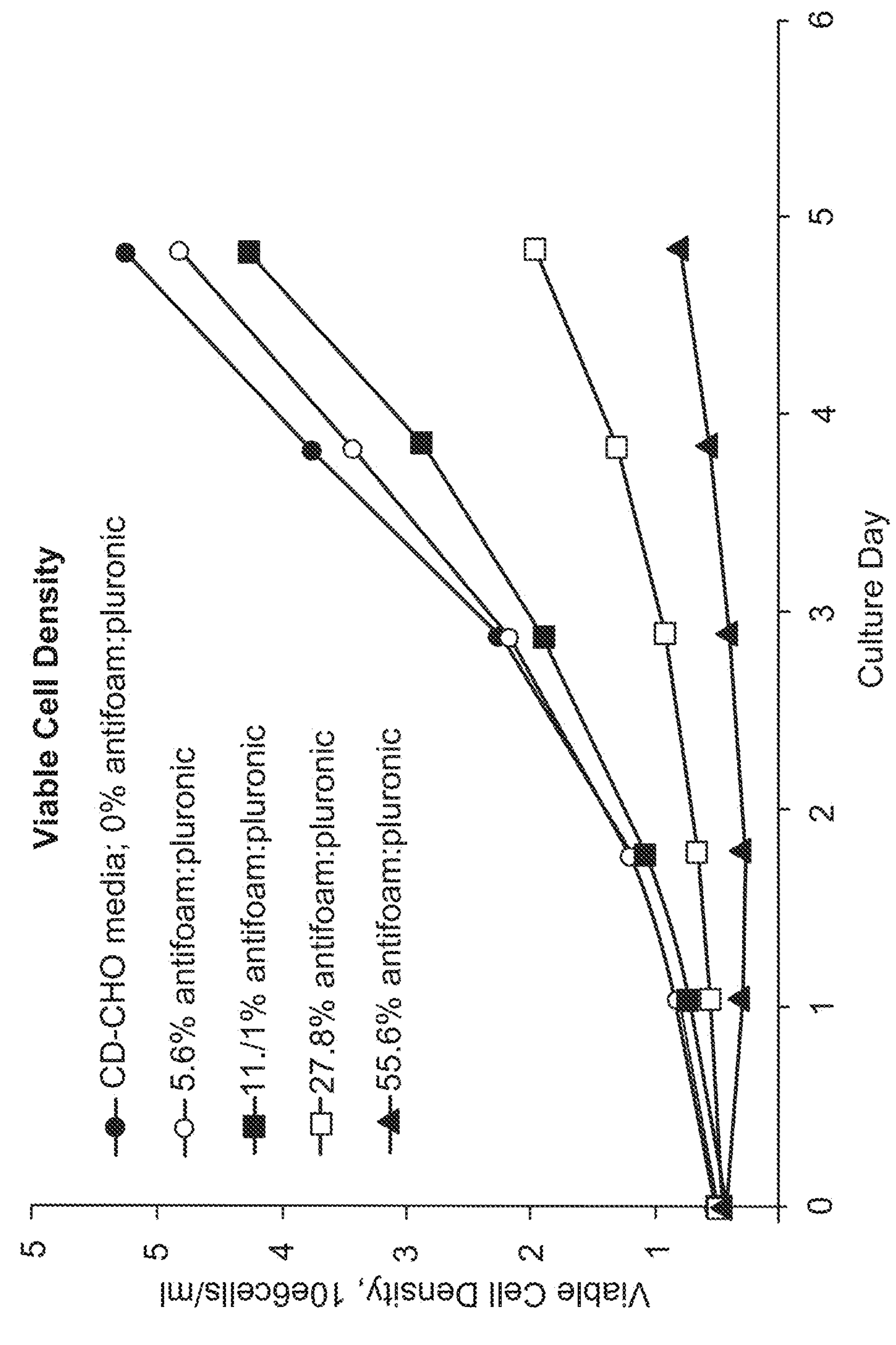

FIG. 14 is a graph of the viable cell density over time for different batch shake flask cell culture runs performed using CD-CHO liquid medium containing a 0% antifoam-c to poloxamer-188 ratio (filled circles), a 5.6% antifoam-c to poloxamer-188 ratio (open circles), a 11.1% antifoam-c to poloxamer-188 ratio (filled squares), a 27.8% antifoam-c to poloxamer-188 ratio (open squares), or a 55.6% antifoam-c to poloxamer-188 ratio (filled triangles).

Figure 15:
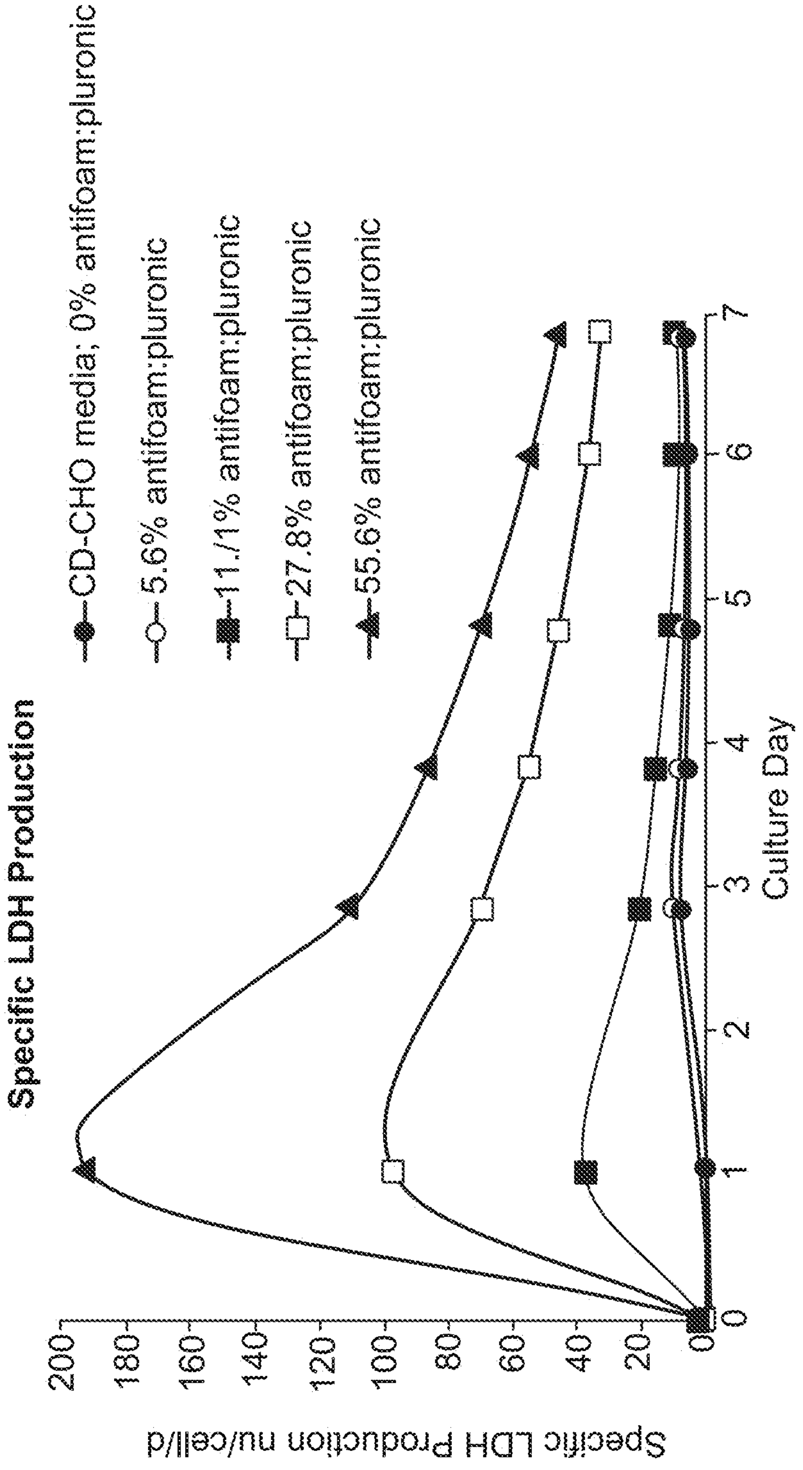

FIG. 15 is a graph of the specific lactate dehydrogenase production rate over time for different batch shake flask cell culture runs performed using CD-CHO liquid medium containing a 0% antifoam-c to poloxamer-188 ratio (filled circles), a 5.6% antifoam-c to poloxamer-188 ratio (open circles), a 11.1% antifoam-c to poloxamer-188 ratio (filled squares), a 27.8% antifoam-c to poloxamer-188 ratio (open squares), or a 55.6% antifoam-c to poloxamer-188 ratio (filled triangles).

DETAILED DESCRIPTION

Provided herein are methods of culturing a mammalian cell that include culturing a mammalian cell including a recombinant protein-encoding nucleic acid under conditions sufficient to produce the recombinant protein, where the culturing includes culturing in a liquid medium including poloxamer-188 at a concentration of 1.8 g/L or at a greater concentration than 1.8 g·L and where the poloxamer-188 is present in the medium and/or added to the medium prior to the culturing step and/or is added to the medium during the culturing step. Also provided are methods of culturing a mammalian cell that include providing a culture system including a vessel, a liquid medium disposed within the vessel, and a sparger disposed within the vessel including a plurality of pores configured to dispense gas through the sparger into the liquid medium, and culturing a mammalian cell including a recombinant protein-encoding nucleic acid in the culturing system under conditions and a gas flow rate sufficient to produce the recombinant protein in the system, where the medium includes a poloxmer-188 concentration that is selected based on one or more factors selected from the group of: pore size, pore type, gas flow rate, viable cell density in the medium, and markers related to cell stress. Exemplary non-limiting aspects of these methods are described below.

In some embodiments, the methods provided herein can achieve a cell culture having a viable cell density of greater than $20\times10^6$ cells/mL, greater than $25\times10^6$ cells/mL, greater than $30\times10^6$ cells/mL, greater than $35\times10^6$ cells/mL, greater than $40\times10^6$ cells/mL, greater than $45\times10^6$ cells/mL, greater than $50\times10^6$ cells/mL, greater than $55\times10^6$ cells/mL, greater than $60\times10^6$ cells/mL, greater than $65\times10^6$ cells/mL, greater than $70\times10^6$ cells/mL, greater than $75\times10^6$ cells/mL, greater than $80\times10^6$ cells/mL, greater than $85\times10^6$ cells/mL, greater than $90\times10^6$ cells/mL, greater than $95\times10^6$ cells/mL, greater than $100\times10^6$ cells/mL, greater than $105\times10^6$ cells/mL, greater than $110\times10^6$ cells/mL, greater than $115\times10^6$ cells/mL, greater than $120\times10^6$ cells/mL, greater than $125\times10^6$ cells/mL, greater than $130\times10^6$ cells/mL, greater than $135\times10^6$ cells/mL, greater than $140\times10^6$ cells/mL, greater than $145\times10^6$ cells/mL, greater than $150\times10^6$ cells/mL, greater than $155\times10^6$ cells/mL, greater than $160\times10^6$ cells/mL, greater than $165\times10^6$ cells/mL, greater than $170\times10^6$ cells/mL, greater than $175\times10^6$ cells/mL, greater than $180\times10^6$ cells/mL, greater than $185\times10^6$ cells/mL, greater than $190\times10^6$ cells/mL, greater than $195\times10^6$ cells/mL, greater than $200\times10^6$ cells/mL, greater than $205\times10^6$ cells/mL, greater than $210\times10^6$ cells/mL, greater than $215\times10^6$ cells/mL, greater than $220\times10^6$ cells/mL, greater than $225\times10^6$ cells/mL, greater than $230\times10^6$ cells/mL, greater than $235\times10^6$ cells/mL, greater than $240\times10^6$ cells/mL, greater than $245\times10^6$ cells/mL, or greater than $250\times10^6$ cells/mL. Methods for determining the viable cell density of a cell culture are well known in the art.

In some embodiments, the methods provided herein provide for a cell culture having a percentage cell viability that is greater than 75% (e.g., greater than 80%, greater than 85%, or greater than 90%) over a culturing period of at least 5 days (e.g., at least 10 days, at least 15 days, at least 20 days, at least 25 days, at least 30 days, at least 35 days, at least 40 days, at least 45 days, at least 50 days, at least 55 days, at least 60 days, at least 65 days, or at least 70 days). In some embodiments, the method provided herein can achieve a culture having a volumetric productivity rate (VPR) of at least 1.5 g/L/d (e.g., at least 1.6 g/L/d, at least 1.7 g/L/d, at least 1.8 g/L/d, at least 1.9 g/L/d, at least 2.0 g/L/d, at least 2.1 g/L/d, at least 2.2 g/L/day, at least 2.3 g/L/d, at least 2.4 g/L/d, at least 2.5 g/L/d, at least 2.6 g/L/d, at least 2.7 g/L/d, at least 2.8 g/L/d, at least 2.9 g/L/d, at least 3.0 g/L/d, at least 3.1 g/L/d, at least 3.2 g/L/d, at least 3.3 g/L/d, at least 3.4 g/L/d, at least 3.5 g/L/d, at least 3.6 g/L/d, at least 3.7 g/L/d, at least 3.8 g/L/d, at least 3.9 g/L/d, at least 4.0 g/L/d, at least 4.1 g/L/d, at least 4.2 g/L/d, at least 4.3 g/L/d, at least 4.4 g/L/d, or at least 4.5 g/L/d) over at least 5 days (e.g., at least 10 days, at least 15 days, at least 20 days, at least 25 days, at least 30 days, at least 35 days, at least 40 days, at least 45 days, at least 50 days, at least 55 days, at least 60 days, at least 65 days, or at least 70 days) starting at any time during the culturing period.

In some embodiments, the methods provided herein result in the production of a recombinant protein that when collected has a decreased level (e.g., a decrease of about or less than 5%, a decrease of about or less than 10%, a decrease of about or less than 15%, a decrease of about or less than 20%, a decrease of about or less than 25%, a decrease of about or less than 30%, a decrease of about or less than 35%, a decrease of about or less than 40%, a decrease of about or less than 45%, a decrease of about or less than 50%, a decrease of about or less than 55%, a decrease of about or less than 60%, a decrease of about or less than 65%, a decrease of about or less than 70%, a decrease of about or less than 75%, a decrease of about or less than 80%, a decrease of about or less than 80%, a decrease of about or less than 85%, or a decrease of about or less than 90%) of degradation (as compared to a recombinant protein produced in a similar method that does not include culturing in a liquid medium including 1.8 g/L or more poloxamer-188). The level of degradation of a recombinant protein collected from a cell culture can be detected, e.g., using gel electrophoresis and/or immunoblotting.

In some embodiments, the methods result in a cell culture that has a specific lactate dehydrogenase production of less than 60 nU/cell/day (e.g., less than 55 nU/cell/day, less than 50 nU/cell/day, less than 45 nU/cell/day, less than 40 nU/cell/day, less than 35 nU/cell/day, less than 30 nU/cell/day, less than 25 nU/cell/day, or less than 20 nU/cell/day) over at least about 5 (e.g., at least 10, at least 15, at least 20, at least 25, at least 30, at least 35, at least 40, at least 45, at least 50, at least 55, at least 60, at least 65, or at least 70) continuous days starting at any time within the culturing period.

In some embodiments, the methods result in the maintenance of the cells in a steady state (stationary phase) for at least 5 days (e.g., at least 10 days, at least 15 days, at least 20 days, at least 25 days, at least 30 days, at least 35 days, at least 40 days, at least 45 days, or at least 50 days), e.g., at a viable cell density about or greater than $30\times10^6$ cells/mL, about or greater than $35\times10^6$ cells/mL, about or greater than $40\times10^6$ cells/mL, about or greater than $45\times10^6$ cells/mL, about or greater than $50\times10^6$ cells/mL, about or greater than $55\times10^6$ cells/mL, about or greater than $60\times10^6$ cells/mL, about or greater than $65\times10^6$ cells/mL, about or greater than $70\times10^6$ cells/mL, about or greater than $75\times10^6$ cells/mL, about or greater than $80\times10^6$ cells/mL, about or greater than $85\times10^6$ cells/mL, about or greater than $90\times10^6$ cells/mL, about or greater than $95\times10^6$ cells/mL, about or greater than $100\times10^6$ cells/mL, about or greater than $105\times10^6$ cells/mL, about or greater than $110\times10^6$ cells/mL, about or greater than $115\times10^6$ cells/mL, about or greater than $120\times10^6$ cells/mL, about or greater than $125\times10^6$ cells/mL, about or greater than $130\times10^6$ cells/mL, about or greater than $135\times10^6$ cells/mL, about or greater than $140\times10^6$ cells/mL, about or greater than $145\times10^6$ cells/mL, about or greater than $150\times10^6$ cells/mL, about or greater than $155\times10^6$ cells/mL, about or greater than $160\times10^6$ cells/mL, about or greater than $165\times10^6$ cells/mL, about or greater than $170\times10^6$ cells/mL, about or greater than $175\times10^6$ cells/mL, about or greater than $180\times10^6$ cells/mL, about or greater than $185\times10^6$ cells/mL, about or greater than $190\times10^6$ cells/mL, about or greater than $195\times10^6$ cells/mL, or about or greater than $200\times10^6$ cell s/mL.

Culture Volumes

The culturing step (e.g., perfusion culturing step) in any of the methods described can include incubating a cell culture having a volume of between 20 L and about 8,000 L (e.g., between about 20 L and about 7,000 L, between about 20 L and about 6,000 L, between about 20 L an about 5,000 L, between about 20 L and about 4,000 L, between about 20 L and about 3,000 L, between about 20 L and about 2,500 L, between about 20 L and about 2,000 L, between about 20 L and about 1,500 L, between about 20 L and about 1,000 L, between about 20 L and about 500 L, between about 20 L and about 200 L, between about 20 L and about 100 L, between about 100 L and about 8,000 L, between about 100 L and about 7,000 L, between about 100 L and about 6,000 L, between about 100 L and about 5,000 L, between about 100 L and about 4,000 L, between about 100 L and about 3,000 L, between about 100 L and about 2,000 L, between about 100 L and about 1,500 L, between about 100 L and about 1,000 L, between about 100 L and about 800 L, between about 100 L and about 700 L, between about 100 L and about 600 L, between about 100 L and about 500 L, between about 100 L and about 400 L, between about 100 L and about 300 L, between about 100 L and about 200 L, between about 500 L and about 8,000 L, between about 500 L and about 7,000 L, between about 500 L and about 6,000 L, between about 500 L and about 5,000 L, between about 500 L and about 4,000 L, between about 500 L and about 3,000 L, between about 500 L and about 2,000 L, between about 500 L and about 1,500 L, between about 500 L and about 1,000 L, between about 500 L and about 750 L, between about 1,000 L and about 8,000 L, between about 1,000 L and about 7,000 L, between about 1,000 L and about 6,000 L, between about 1,000 L and about 5,000 L, between about 1,000 L and about 4,000 L, between about 1,000 L and about 3,000 L, between about 1,000 L and about 2,000 L, between about 1,000 L and about 1,500 L, between about 2,000 L and about 8,000 L, between about 2,000 L and about 7,000 L, between about 2,000 L and about 6,000 L, between about 2,000 L and about 5,000 L, between about 2,000 L and about 4,000 L, between about 2,000 L and about 3,000 L, between about 3,000 L and about 8,000 L, between about 3,000 L and about 7,000 L, between about 3,000 L and about 6,000 L, between about 3,000 L and about 5,000 L, between about 3,000 L and about 4,000 L, between about 4,000 L and about 8,000 L, between about 4,000 L and about 7,000 L, between about 4,000 L and about 6,000 L, between about 4,000 L and about 5,000 L, between about 5,000 L and about 8,000 L, between about 5,000 L and about 7,000 L, between about 5,000 L and about 6,000 L, between about 6,000 L and about 8,000 L, between about 6,000 L and about 7,000 L, or between about 7,000 L or about 8,000 L) under conditions that allow for cell maintenance and proliferation in the culture.

As is known in the art, the volume of a cell culture can remain substantially the same or can increase over time during the culturing period (e.g., as described below).

Culturing Period

Culturing (e.g., perfusion culturing) in any of the methods described herein can be performed over a period of time of between about 3 days to about 100 days (e.g., between about 3 days and about 95 days, between about 3 days and about 90 days, between about 3 days and about 85 days, between about 3 days and about 80 days, between about 3 days and about 75 days, between about 3 days and about 70 days, between about 3 days and about 65 days, between about 3 days and about 60 days, between about 3 days and about 55 days, between about 3 days and about 50 days, between about 3 days and about 45 days, between about 3 days and about 40 days, between about 3 days and about 35 days, between about 3 days and about 30 days, between about 3 days and about 25 days, between about 3 days and about 20 days, between about 3 days and about 15 days, between about 3 days and about 10 days, between about 5 days and about 100 days, between about 5 days and about 95 days, between about 5 days and about 90 days, between about 5 days and about 85 days, between about 5 days and about 80 days, between about 5 days and about 75 days, between about 5 days and about 70 days, between about 5 days and about 65 days, between about 5 days and about 60 days, between about 5 days and about 55 days, between about 5 days and about 50 days, between about 5 days and about 45 days, between about 5 days and about 40 days, between about 5 days and about 35 days, between about 5 days and about 30 days, between about 5 days and about 25 days, between about 5 days and about 20 days, between about 5 days and about 15 days, between about 5 days and about 10 days, between about 10 days and about 100 days, between about 10 days and about 95 days, between about 10 days and about 90 days, between about 10 days and about 85 days, between about 10 days and about 80 days, between about 10 days and about 75 days, between about 10 days and about 70 days, between about 10 days and about 65 days, between about 10 days and about 60 days, between about 10 days and about 55 days, between about 10 days and about 50 days, between about 10 days and about 45 days, between about 10 days and about 40 days, between about 10 days and about 35 days, between about 10 days and about 30 days, between about 10 days and about 25 days, between about 10 days and about 20 days, between about 10 days and about 15 days, between about 15 days and about 100 days, between about 15 days and about 95 days, between about 15 days and about 90 days, between about 15 days and about 85 days, between about 15 days and about 80 days, between about 15 days and about 75 days, between about 15 days and about 70 days, between about 15 days and about 65 days, between about 15 days and about 60 days, between about 15 days and about 55 days, between about 15 days and about 50 days, between about 15 days and about 45 days, between about 15 days and about 40 days, between about 15 days and about 35 days, between about 15 days and about 30 days, between about 15 days and about 25 days, between about 15 days and about 20 days, between about 20 days and about 100 days, between about 20 days and about 95 days, between about 20 days and about 90 days, between about 20 days and about 85 days, between about 20 days and about 80 days, between about 20 days and about 75 days, between about 20 days and about 70 days, between about 20 days and about 65 days, between about 20 days and about 60 days, between about 20 days and about 55 days, between about 20 days and about 50 days, between about 20 days and about 45 days, between about 20 days and about 40 days, between about 20 days and about 35 days, between about 20 days and about 30 days, between about 20 days and about 25 days, between about 25 days and about 100 days, between about 25 days and about 95 days, between about 25 days and about 90 days, between about 25 days and about 85 days, between about 25 days and about 80 days, between about 25 days and about 75 days, between about 25 days and about 70 days, between about 25 days and about 65 days, between about 25 days and about 60 days, between about 25 days and about 55 days, between about 25 days and about 50 days, between about 25 days and about 45 days, between about 25 days and about 40 days, between about 25 days and about 35 days, between about 25 days and about 30 days, between about 30 days and about 100 days, between about 30 days and about 90 days, between about 30 days and about 80 days, between about 30 days and about 70 days, between about 30 days and about 60 days, between about 30 days and about 50 days, between about 30 days and about 40 days, between about 40 days and about 100 days, between about 40 days and about 90 days, between about 40 days and about 80 days, between about 40 days and about 70 days, between about 40 days and about 60 days, between about 40 days and about 50 days, between about 50 days and about 100 days, between about 50 days and about 90 days, between about 50 days and about 80 days, between about 50 days and about 70 days, between about 50 days and about 60 days, between about 60 days and about 100 days, between about 60 days and about 90 days, between about 60 days and about 80 days, between about 60 days and about 70 days, between about 70 days and about 100 days, between about 70 days and about 90 days, between about 70 days and about 80 days, between about 80 days and about 100 days, between about 80 days and about 90 days, or between about 90 days and about 100 days).

Mammalian Cells

The mammalian cell cultured (e.g., perfusion cultured) in the methods provided herein can be a cell that grows in suspension or an adherent cell. Non-limiting examples of mammalian cells that can be cultured in any of the methods described herein include: Chinese hamster ovary (CHO) cells (e.g., CHO DG44 cells or CHO-K 1 s cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, an NSO cell, a baby hamster kidney (BHK) cell, a PerC6 cell, a Vero cells, a HT-1080 cell, and Madin-Darby Canine (Cocker Spaniel) kidney epithelial cells (MDCK) cells. In some examples where an adherent cell is cultured, the culture can also contain a plurality of microcarriers (e.g., microcarriers that contain one or more pores). Additional mammalian cells that can be cultured in any of the methods described herein are known in the art.

The mammalian cell can contain a recombinant nucleic acid (e.g., a nucleic acid stably integrated in the mammalian cell's genome) that encodes a recombinant protein. Non-limiting examples of recombinant nucleic acids that encode exemplary recombinant proteins are described below, as are recombinant proteins that can be produced using the methods described herein. In some instances, the mammalian cell that is cultured in a bioreactor (e.g., any of the bioreactors described herein) was derived from a larger culture.

A nucleic acid encoding a recombinant protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the mammalian cell (transient transfection), while in others the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a (3-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the recombinant protein is a secreted protein and is released by the mammalian cell into the extracellular medium (e.g., the first and/or second liquid medium in perfusion culturing or the first liquid medium and/or feed liquid medium in feed batch culturing). For example, a nucleic acid sequence encoding a soluble recombinant protein can contain a sequence that encodes a secretion signal peptide at the N- or C-terminus of the recombinant protein, which is cleaved by an enzyme present in the mammalian cell, and subsequently released into the extracellular medium (e.g., the first and/or second liquid medium).

Bioreactors

The culturing step in any of the methods described herein can be performed using a bioreactor (e.g., a perfusion bioreactor or a fed batch bioreactor). A bioreactor (e.g., a perfusion bioreactor or a fed batch bioreactor) used to perform the culturing step can have an internal volume (capacity) of between about 24 L to about 25,000 L (e.g., between about 24 L and about 20,000 L, between about 24 L and about 15,000 L, between about 24 L and about 10,000 L, between about 24 L and about 9,500 L, between about 24 L and about 9,000 L, between about 24 L and about 8,500 L, between about 24 L and about 8,000 L, between about 24 L and about 7,500 L, between about 24 L and about 7,000 L, between about 24 L and about 6,500 L, between about 24 L and about 6,000 L, between about 24 L and about 5,500 L, between about 24 L and about 5,000 L, between about 24 L and about 4,500 L, between about 24 L and about 4,000 L, between about 24 L and about 3,500 L, between about 24 L and about 3,000 L, between about 24 L and about 2,500 L, between about 24 L and about 2,000 L, between about 24 L and about 1,500 L, between about 24 L and about 1,000 L, between about 24 L and about 900 L, between about 24 L and about 800 L, between about 24 L and about 700 L, between about 24 L and about 600 L, between about 24 L and about 500 L, between about 24 L and about 400 L, between about 24 L and about 300 L, between about 24 L and about 200 L, between about 24 L and about 100 L, between about 100 L and about 25,000 L, between about 100 L and about 20,000 L, between about 100 L and about 15,000, between about 100 L and about 10,000 L, between about 100 L and about 9,500 L, between about 100 L and about 9,000 L, between about 100 L and about 8,500 L, between about 100 L and about 8,000 L, between about 100 L and about 7,500 L, between about 100 L and about 7,000 L, between about 100 L and about 6,500 L, between about 100 L and about 6,000 L, between about 100 L and about 5,500 L, between about 100 L and about 5,000 L, between about 100 L and about 4,500 L, between about 100 L and about 4,000 L, between about 100 L and about 3,500 L, between about 100 L and about 3,000 L, between about 100 L and about 2,500 L, between about 100 L and about 2,000 L, between about 100 L and about 1,500 L, between about 100 L and about 1,000 L, between about 100 L and about 900 L, between about 100 L and about 800 L, between about 100 L and about 700 L, between about 100 L and about 600 L, between about 100 L and about 500 L, between about 100 L and about 400 L, between about 100 L and about 300 L, between about 100 L and about 200 L, between about 200 L and about 25,000 L, between about 200 L and about 20,000 L, between about 200 L and about 15,000 L, between about 200 L and about 10,000 L, between about 200 L and about 9,500 L, between about 200 L and about 9,000 L, between about 200 L and about 8,500 L, between about 200 L and about 8,000 L, between about 200 L and about 7,500 L, between about 200 L and about 7,000 L, between about 200 L and about 6,500 L, between about 200 L and about 6,000 L, between about 200 L and about 5,500 L, between about 200 L and about 5,000 L, between about 200 L and about 4,500 L, between about 200 L and about 4,000 L, between about 200 L and about 3,500 L, between about 200 L and about 3,000 L, between about 200 L and about 2,500 L, between about 200 L and about 2,000 L, between about 200 L and about 1,500 L, between about 200 L and about 1,000 L, between about 200 L and about 900 L, between about 200 L and about 800 L, between about 200 L and about 700 L, between about 200 L and about 600 L, between about 200 L and about 500 L, between about 200 L and about 400 L, between about 200 L and about 300 L, between about 500 L and about 25,000 L, between about 500 L and about 20,000 L, between about 500 L and about 15,000 L, between about 500 L and about 10,000 L, between about 500 L and about 9,500 L, between about 500 L and about 9,000 L, between about 500 L and about 8,500 L, between about 500 L and about 8,000 L, between about 500 L and about 7,500 L, between about 500 L and about 7,000 L, between about 500 L and about 6,500 L, between about 500 L and about 6,000 L, between about 500 L and about 5,500 L, between about 500 L and about 5,000 L, between about 500 L and about 4,500 L, between about 500 L and about 4,000 L, between about 500 L and about 3,500 L, between about 500 L and about 3,000 L, between about 500 L and about 2,500 L, between about 500 L and about 2,000 L, between about 500 L and about 1,500 L, between about 500 L and about 1,000 L, between about 500 L and about 900 L, between about 500 L and about 800 L, between about 500 L and about 700 L, between about 500 L and about 600 L, between about 1,000 L and about 25,000 L, between about 1,000 L and about 20,000 L, between about 1,000 L and about 15,000 L, between about 1,000 L and about 10,000 L, between about 1,000 L and about 9,500 L, between about 1,000 L and about 9,000 L, between about 1,000 L and about 8,500 L, between about 1,000 L and about 8,000 L, between about 1,000 L and about 7,500 L, between about 1,000 L and about 7,000 L, between about 1,000 L and about 6,500 L, between about 1,000 L and about 6,000 L, between about 1,000 L and about 5,500 L, between about 1,000 L and about 5,000 L, between about 1,000 L and about 4,500 L, between about 1,000 L and about 4,000 L, between about 1,000 L and about 3,500 L, between about 1,000 L and about 3,000 L, between about 1,000 L and about 2,500 L, between about 1,000 L and about 2,000 L, between about 1,000 L and about 1,500 L, between about 2,000 L and about 25,000 L, between about 2,000 L and about 20,000 L, between about 2,000 L and about 15,000 L, between about 2,000 L and about 10,000 L, between about 2,000 L and about 9,500 L, between about 2,000 L and about 9,000 L, between about 2,000 L and about 8,500 L, between about 2,000 L and about 8,000 L, between about 2,000 L and about 7,500 L, between about 2,000 L and about 7,000 L, between about 2,000 L and about 6,500 L, between about 2,000 L and about 6,000 L, between about 2,000 L and about 5,500 L, between about 2,000 L and about 5,000 L, between about 2,000 L and about 4,500 L, between about 2,000 L and about 4,000 L, between about 2,000 L and about 3,500 L, between about 2,000 L and about 3,000 L, between about 2,000 L and about 2,500 L, between about 3,000 L and about 25,000 L, between about 3,000 L and about 20,000 L, between about 3,000 L and about 15,000 L, between about 3,000 L and about 10,000 L, between about 3,000 L and about 9,500 L, between about 3,000 L and about 9,000 L, between about 3,000 L and about 8,500 L, between about 3,000 L and about 8,000 L, between about 3,000 L and about 7,500 L, between about 3,000 L and about 7,000 L, between about 3,000 L and about 6,500 L, between about 3,000 L and about 6,000 L, between about 3,000 L and about 5,500 L, between about 3,000 L and about 5,000 L, between about 3,000 L and about 4,500 L, between about 3,000 L and about 4,000 L, between about 3,000 L and about 3,500 L, between about 4,000 L and about 9,000 L, between about 4,000 L and about 25,000 L, between about 4,000 L and about 20,000 L, between about 4,000 L and about 15,000 L, between about 4,000 L and about 10,000 L, between about 4,000 L and about 9,500 L, between about 4,000 L and about 9,000 L, between about 4,000 L and about 8,500 L, between about 4,000 L and about 8,000 L, between about 4,000 L and about 7,500 L, between about 4,000 L and about 7,000 L, between about 4,000 L and about 6,500 L, between about 4,000 L and about 6,000 L, between about 4,000 L and about 5,500 L, between about 4,000 L and about 5,000 L, between about 4,000 L and about 4,500 L, between about 5,000 L and about 25,000 L, between about 5,000 L and about 20,000 L, between about 5,000 L and about 15,000 L, between about 5,000 L and about 10,000 L, between about 5,000 L and about 9,500 L, between about 5,000 L and about 9,000 L, between about 5,000 L and about 8,500 L, between about 5,000 L and about 8,000 L, between about 5,000 L and about 7,500 L, between about 5,000 L and about 7,000 L, between about 5,000 L and about 6,500 L, between about 5,000 L and about 6,000 L, between about 5,000 L and about 5,500 L, between about 6,000 L and about 25,000 L, between about 6,000 L and about 20,000 L, between about 6,000 L and about 15,000 L, between about 6.000 L and about 10,000 L, between about 6,000 L and about 9,500 L, between about 6,000 L and about 9,000 L, between about 6,000 L and about 8,500 L, between about 6,000 L and about 8,000 L, between about 6,000 L and about 7,500 L, between about 6,000 L and about 7,000 L, between about 6,000 L and about 6,500 L, between 7,000 L and about 25,000 L, between about 7,000 L and about 20,000 L, between about 7,000 L and about 15,000 L, between about 7,000 L and about 10,000 L, between about 7,000 L and about 9,500 L, between about 7,000 L and about 9,000 L, between about 7,000 L and about 8,500 L, between about 7,000 L and about 8,000 L, between about 7,000 L and about 7,500 L, between about 8,000 L and about 25,000 L, between about 8,000 L and about 20,000 L, between about 8,000 L and about 15,000 L, between about 8,000 L and about 10,000 L, between about 8,000 L and about 9,500 L, between about 8,000 L and about 9,000 L, between about 8,000 L and about 8,500 L, between about 9,000 L and about 25,000 L, between about 9,000 L and about 20,000 L, between about 9,000 L and about 15,000 L, between about 9,000 L and about 10,000 L, between about 9,000 L and about 9,500 L, between about 10,000 L and about 25,000 L, between about 10,000 L and about 20,000 L, between about 10,000 L and about 15,000 L, between about 15,000 L and about 25,000 L, between about 15,000 L and about 20,000 L, or between about 20,000 L and about 25,000 L).

Culture Systems

Some of the methods described herein use a culturing system (e.g., a perfusion culturing system) that includes a vessel, a liquid medium disposed within the vessel (e.g., any of the culture media described herein), and a sparger disposed within the vessel including a plurality of pores configured to dispense gas through the sparger into the liquid medium. The vessel can have an internal volume (capacity) of between about 24 L to about 20,000 L (e.g., between about 24 L and about 15,000 L, between about 24 L and about 10,000 L, between about 24 L and about 9,500 L, between about 24 L and about 9,000 L, between about 24 L and about 8,500 L, between about 24 L and about 8,000 L, between about 24 L and about 7,500 L, between about 24 L and about 7,000 L, between about 24 L and about 6,500 L, between about 24 L and about 6,000 L, between about 24 L and about 5,500 L, between about 24 L and about 5,000 L, between about 24 L and about 4,500 L, between about 24 L and about 4,000 L, between about 24 L and about 3,500 L, between about 24 L and about 3,000 L, between about 24 L and about 2,500 L, between about 24 L and about 2,000 L, between about 24 L and about 1,500 L, between about 24 L and about 1,000 L, between about 24 L and about 900 L, between about 24 L and about 800 L, between about 24 L and about 700 L, between about 24 L and about 600 L, between about 24 L and about 500 L, between about 24 L and about 400 L, between about 24 L and about 300 L, between about 24 L and about 200 L, between about 24 L and about 100 L, between about 100 L and about 20,000 L, between about 100 L and about 15,000 L, between about 100 L and about 10,000 L, between about 100 L and about 9,500 L, between about 100 L and about 9,000 L, between about 100 L and about 8,500 L, between about 100 L and about 8,000 L, between about 100 L and about 7,500 L, between about 100 L and about 7,000 L, between about 100 L and about 6,500

L, between about 100 L and about 6,000 L, between about 100 L and about 5,500 L, between about 100 L and about 5,000 L, between about 100 L and about 4,500 L, between about 100 L and about 4,000 L, between about 100 L and about 3,500 L, between about 100 L and about 3,000 L, between about 100 L and about 2,500 L, between about 100 L and about 2,000 L, between about 100 L and about 1,500 L, between about 100 L and about 1,000 L, between about 100 L and about 900 L, between about 100 L and about 800 L, between about 100 L and about 700 L, between about 100 L and about 600 L, between about 100 L and about 500 L, between about 100 L and about 400 L, between about 100 L and about 300 L, between about 100 L and about 200 L, between about 200 L and about 20,000 L, between about 200 L and about 15,000 L, between about 200 L and about 10,000 L, between about 200 L and about 9,500 L, between about 200 L and about 9,000 L, between about 200 L and about 8,500 L, between about 200 L and about 8,000 L, between about 200 L and about 7,500 L, between about 200 L and about 7,000 L, between about 200 L and about 6,500 L, between about 200 L and about 6,000 L, between about 200 L and about 5,500 L, between about 200 L and about 5,000 L, between about 200 L and about 4,500 L, between about 200 L and about 4,000 L, between about 200 L and about 3,500 L, between about 200 L and about 3,000 L, between about 200 L and about 2,500 L, between about 200 L and about 2,000 L, between about 200 L and about 1,500 L, between about 200 L and about 1,000 L, between about 200 L and about 900 L, between about 200 L and about 800 L, between about 200 L and about 700 L, between about 200 L and about 600 L, between about 200 L and about 500 L, between about 200 L and about 400 L, between about 200 L and about 300 L, between about 500 L and about 20,000 L, between about 500 L and about 15,000 L, between about 500 L and about 10,000 L, between about 500 L and about 9,500 L, between about 500 L and about 9,000 L, between about 500 L and about 8,500 L, between about 500 L and about 8,000 L, between about 500 L and about 7,500 L, between about 500 L and about 7,000 L, between about 500 L and about 6,500 L, between about 500 L and about 6,000 L, between about 500 L and about 5,500 L, between about 500 L and about 5,000 L, between about 500 L and about 4,500 L, between about 500 L and about 4,000 L, between about 500 L and about 3,500 L, between about 500 L and about 3,000 L, between about 500 L and about 2,500 L, between about 500 L and about 2,000 L, between about 500

L and about 1,500 L, between about 500 L and about 1,000 L, between about 500 L and about 900 L, between about 500 L and about 800 L, between about 500 L and about 700 L, between about 500 L and about 600 L, between about 1,000 L and about 25,000 L, between about 1,000 L and about 20,000 L, between about 1,000 L and about 15,000 L, between about 1,000 L and about 10,000 L, between about 1,000 L and about 9,500 L, between about 1,000 L and about 9,000 L, between about 1,000 L and about 8,500 L, between about 1,000 L and about 8,000 L, between about 1,000 L and about 7,500 L, between about 1,000 L and about 7,000 L, between about 1,000 L and about 6,500 L, between about 1,000 L and about 6,000 L, between about 1,000 L and about 5,500 L, between about 1,000 L and about 5,000 L, between about 1,000 L and about 4,500 L, between about 1,000 L and about 4,000 L, between about 1,000 L and about 3,500 L, between about 1,000 L and about 3,000 L, between about 1,000 L and about 2,500 L, between about 1,000 L and about 2,000 L, between about 1,000 L and about 1,500 L, between about 2,000 L and about 20,000 L, between about 2,000 L and about 15,000 L, between about 2,000 L and about 10,000 L, between about 2,000 L and about 9,500 L, between about 2,000 L and about 9,000 L, between about 2,000 L and about 8,500 L, between about 2,000 L and about 8,000 L, between about 2,000 L and about 7,500 L, between about 2,000 L and about 7,000 L, between about 2,000 L and about 6,500 L, between about 2,000 L and about 6,000 L, between about 2,000 L and about 5,500 L, between about 2,000 L and about 5,000 L, between about 2,000 L and about 4,500 L, between about 2,000 L and about 4,000 L, between about 2,000 L and about 3,500 L, between about 2,000 L and about 3,000 L, between about 2,000 L and about 2,500 L, between about 3,000 L and about 20,000 L, between about 3,000 L and about 15,000 L, between about 3,000 L and about 10,000 L, between about 3,000 L and about 9,500 L, between about 3,000 L and about 9,000 L, between about 3,000 L and about 8,500 L, between about 3,000 L and about 8,000 L, between about 3,000 L and about 7,500 L, between about 3,000 L and about 7,000 L, between about 3,000 L and about 6,500 L, between about 3,000 L and about 6,000 L, between about 3,000 L and about 5,500 L, between about 3,000 L and about 5,000 L, between about 3,000 L and about 4,500 L, between about 3,000 L and about 4,000 L, between about 3,000 L and about 3,500 L, between about 4,000 L and about 20,000 L, between about 4,000 L and about 15,000 L, between about 4,000 L and about 10,000 L, between about 4,000 L and about 9,500 L, between about 4,000 L and about 9,000 L, between about 4,000 L and about 8,500 L, between about 4,000 L and about 8,000 L, between about 4,000 L and about 7,500 L, between about 4,000 L and about 7,000 L, between about 4,000 L and about 6,500 L, between about 4,000 L and about 6,000 L, between about 4,000 L and about 5,500 L, between about 4,000 L and about 5,000 L, between about 4,000 L and about 4,500 L, between about 5,000 L and about 20,000 L, between about 5,000 L and about 15,000 L, between about 5,000 L and about 10,000 L, between about 5,000 L and about 9,500 L, between about 5,000 L and about 9,000 L, between about 5,000 L and about 8,500 L, between about 5,000 L and about 8,000 L, between about 5,000 L and about 7,500 L, between about 5,000 L and about 7,000 L, between about 5,000 L and about 6,500 L, between about 5,000 L and about 6,000 L, between about 5,000 L and about 5,500 L, between about 6,000 L and about 20,000 L, between about 6,000 L and about 10,000 L, between about 6,000 L and about 9,500 L, between about 6,000 L and about 9,000 L, between about 6,000 L and about 8,500 L, between about 6,000 L and about 8,000 L, between about 6,000 L and about 7,500 L, between about 6,000 L and about 7,000 L, between about 6,000 L and about 6,500 L, between about 7,000 L and about 20,000 L, between about 7,000 L and about 15,000 L, between about 7,000 L and about 10,000 L, between about 7,000 L and about 9,500 L, between about 7,000 L and about 9,000 L, between about 7,000 L and about 8,500 L, between about 7,000 L and about 8,000 L, between about 7,000 L and about 7,500 L, between about 8,000 L and about 20,000 L, between about 8,000 L and about 15,000 L, between about 8,000 L and about 10,000 L, between about 8,000 L and about 9,500 L, between about 8,000 L and about 9,000 L, between about 8,000 L and about 8,500 L, between about 9,000 L and about 20,000 L, between about 9,000 L and about 15,000 L, between about 9,000 L and about 10,000 L, between about 9,000 L and about 9,500 L, between about 10,000 L and about 20,000 L, between about 10,000 L and about 15,000 L, or between about 15,000 L and about 20,000 L). The vessel can be made from metal (e.g., stainless steel), plastic, or glass, or any combination thereof.

In some embodiments, the one or more pores of the sparger can have a pore size of between about 750 μm and about 1.5 mm (e.g., between about 750 μm and about 1.45 mm, between about 750 μm and about 1.4 mm, between about 750 μm and about 1.35 mm, between about 750 μm and about 1.3 mm, between about 750 μm and about 1.25 mm, between about 750 μm and about 1.2 mm, between about 750 μm and about 1.15 mm, between about 750 μm and about 1.1 mm, between about 750 μm and about 1.05 mm, between about 750 μm and about 1.0 mm, between about 750 μm and about 950 μm, between about 750 μm and about 900 μm, between about 750 μm and about 850 μm, between about 750 μm and about 800 μm, between about 800 μm and about 1.5 mm, between about 800 μm and about 1.45 mm, between about 800 μm and about 1.4 mm, between about 800 μm and about 1.35 mm, between about 800 μm and about 1.3 mm, between about 800 μm and about 1.25 mm, between about 800 μm and about 1.2 mm, between about 800 μm and about 1.15 mm, between about 800 μm and about 1.1 mm, between about 800 μm and about 1.05 mm, between about 800 μm and about 1.0 mm, between about 800 μm and about 950 μm, between about 800 μm and about 900 μm, between about 800 μm and about 850 μm, between about 850 μm and about 1.5 mm, between about 850 μm and about 1.45 mm, between about 850 μm and about 1.4 mm, between about 850 μm and about 1.35 mm, between about 850 μm and about 1.3 mm, between about 850 μm and about 1.25 mm, between about 850 μm and about 1.2 mm, between about 850 μm and about 1.15 mm, between about 850 μm and about 1.1 mm, between about 850 μm and about 1.05 mm, between about 850 μm and about 1.0 mm, between about 850 μm and about 950 μm, between about 850 μm and about 900 μm, between about 900 μm and about 1.5 mm, between about 900 μm and about 1.45 mm, between about 900 μm and about 1.4 mm, between about 900 μm and about 1.35 mm, between about 900 μm and about 1.3 mm, between about 900 μm and about 1.25 mm, between about 900 μm and about 1.2 mm, between about 900 μm and about 1.15 mm, between about 900 μm and about 1.1 mm, between about 900 μm and about 1.05 mm, between about 900 μm and about 1.0 mm, between about 900 μm and about 950 μm, between about 950 μm and about 1.5 mm, between about 950 μm and about 1.45 mm, between about 950 μm and about 1.4 mm, between about 950 μm and about 1.35 mm, between about 950 μm and about 1.3 mm, between about 950 μm and about 1.25 mm, between about 950 μm and about 1.2 mm, between about 950 μm and about 1.15 mm, between about 950 μm and about 1.1 mm, between about 950 μm and about 1.05 mm, between about 950 μm and about 1.0 mm, between about 1.0 mm and about 1.5 mm, between about 1.0 mm and about 1.45 mm, between about 1.0 mm and about 1.4 mm, between about 1.0 mm and about 1.35 mm, between about 1.0 mm and about 1.3 mm, between about 1.0 mm and about 1.25 mm, between about 1.0 mm and about 1.2 mm, between about 1.0 mm and about 1.15 mm, between about 1.0 mm and about 1.1 mm, between about 1.0 mm and about 1.05 mm, between about 1.05 mm and about 1.5 mm, between about 1.05 mm and about 1.45 mm, between about 1.05 mm and about 1.4 mm, between about 1.05 mm and about 1.35 mm, between about 1.05 mm and about 1.3 mm, between about 1.05 mm and about 1.25 mm, between about 1.05 mm and about 1.2 mm, between about 1.05 mm and about 1.15 mm, between about 1.05 mm and about 1.1 mm, between about 1.1 mm and about 1.5 mm, between about 1.1 mm and about 1.45 mm, between about 1.1 mm and about 1.4 mm, between about 1.1 mm and about 1.35 mm, between about 1.1 mm and about 1.3 mm, between about 1.1 mm and about 1.25 mm, between about 1.1 mm and about 1.2 mm, between about 1.1 mm and about 1.15 mm, between about 1.15 mm and about 1.5 mm, between about 1.15 mm and about 1.45 mm, between about 1.15 mm and about 1.4 mm, between about 1.15 mm and about 1.35 mm, between about 1.15 mm and about 1.3 mm, between about 1.15 mm and about 1.25 mm, between about 1.15 mm and about 1.2 mm, between about 1.2 mm and about 1.5 mm, between about 1.2 mm and about 1.45 mm, between about 1.2 mm and about 1.4 mm, between about 1.2 mm and about 1.35 mm, between about 1.2 mm and about 1.3 mm, between about 1.2 mm and about 1.25 mm, between about 1.25 mm and about 1.5 mm, between about 1.25 mm and about 1.45 mm, between about 1.25 mm and about 1.4 mm, between about 1.25 mm and about 1.35 mm, between about 1.25 mm and about 1.3 mm, between about 1.3 mm and about 1.5 mm, between about 1.3 mm and about 1.45 mm, between about 1.3 mm and about 1.4 mm, between about 1.3 mm and about 1.35 mm, between about 1.35 mm and about 1.5 mm, between about 1.35 mm and about 1.45 mm, between about 1.35 mm and about 1.4 mm, between about 1.4 mm and about 1.5 mm, between about 1.4 mm and about 1.45 mm, or between about 1.45 mm and about 1.5 mm).

In some embodiments, the one or more pores of the sparger can have a pore size of between about 250 μm and about 750 μm (e.g., between about 250 μm and about 700 μm, between about 250 μm and about 650 μm, between about 250 μm and about 600 μm, between about 250 μm and about 550 μm, between about 250 μm and about 500 μm, between about 250 μm and about 450 μm, between about 250 μm and about 400 μm, between about 250 μm and about 350 μm, between about 250 μm and about 300 μm, between about 300 μm and about 750 μm, between about 300 μm and about 650 μm, between about 300 μm and about 600 μm, between about 300 μm and about 550 μm, between about 300 μm and about 500 μm, between about 300 μm and about 450 μm, between about 300 μm and about 400 μm, between about 300 μm and about 350 μm, between about 350 μm and about 750 μm, between about 350 μm and about 700 μm, between about 350 μm and about 650 μm, between about 350 μm and about 600 μm, between about 350 μm and about 550 μm, between about 350 μm and about 500 μm, between about 350 μm and about 450 μm, between about 350 μm and about 400 μm, between about 400 μm and about 750 μm, between about 400 μm and about 700 μm, between about 400 μm and about 650 μm, between about 400 μm and about 600 μm, between about 400 μm and about 550 μm, between about 400 μm and about 500 μm, between about 400 μm and about 450 μm, between about 450 μm and about 750 μm, between about 450 μm and about 700 μm, between about 450 μm and about 650 μm, between about 450 μm and about 600 μm, between about 450 μm and about 550 μm, between about 450 μm and about 500 μm, between about 500 μm and about 750 μm, between about 500 μm and about 700 μm, between about 500 μm and about 650 μm, between about 500 μm and about 600 μm, between about 500 μm and about 550 μm, between about 550 μm and about 750 μm, between about 550 μm and about 700 μm, between about 550 μm and about 650 μm, between about 550 μm and about 600 μm, between about 600 μm and about 750 μm, between about 600 μm and about 700 μm, between about 600 μm and about 650 μm, between about 650 μm and about 750 μm, between about 650 μm and about 700 μm, or between about 700 μm and about 750 μm).

In some embodiments, the one or more pores of the sparger can have a pore size of between about 1 μm and about 250 μm (e.g., between about 1 μm and about 240 μm, between about 1 μm and about 230 μm, between about 1 μm and about 220 μm, between about 1 μm and about 210 μm, between about 1 μm and about 200 μm, between about 1 μm and about 190 μm, between about 1 μm and about 180 μm, between about 1 μm and about 170 μm, between about 1 μm and about 160 μm, between about 1 μm and about 150 μm, between about 1 μm and about 140 μm, between about 1 μm and about 130 μm, between about 1 μm and about 125 μm, between about 1 μm and about 120 μm, between about 1 μm and about 115 μm, between about 1 μm and about 110 μm, between about 1 μm and about 105 μm, between about 1 μm and about 100 μm, between about 1 μm and about 95 μm, between about 1 μm and about 90 μm, between about 1 μm and about 85 μm, between about 1 μm and about 80 μm, between about 1 μm and about 75 μm, between about 1 μm and about 70 μm, between about 1 μm and about 65 μm, between about 1 μm and about 60 μm, between about 1 μm and about 55 μm, between about 1 μm and about 50 μm, between about 1 μm and about 45 μm, between about 1 μm and about 40 μm, between about 1 μm and about 35 μm, between about 1 μm and about 30 μm, between about 1 μm and about 25 μm, between about 1 μm and about 20 μm, between about 1 μm and about 15 μm, between about 1 μm and about 10 μm, between 1 μm and about 5 μm, between 10 μm and about 250 μm, between about 10 μm and about 240 μm, between about 10 μm and about 230 μm, between 10 μm and about 220 μm, between about 10 μm and about 210 μm, between about 10 μm and about 200 μm, between about 10 μm and about 190 μm, between 10 μm and about 180 μm, between about 10 μm and about 170 μm, between about 10 μm and about 160 μm, between about 10 μm and about 150 μm, between about 10 μm and about 140 μm, between about 10 μm and about 130 μm, between about 10 μm and about 120 μm, between about 10 μm and about 110 μm, between about 10 μm and about 100 μm, between about 10 μm and about 90 μm, between about 10 μm and about 80 μm, between about 10 μm and about 70 μm, between about 10 μm and about 60 μm, between about 10 μm and about 50 μm, between about 10 μm and about 40 μm, between about 10 μm and about 30 μm, between about 10 μm and about 20 μm, between about 20 μm and about 250 μm, between about 20 μm and about 240 μm, between about 20 μm and about 230 μm, between about 20 μm and about 220 μm, between about 20 μm and about 210 μm, between about 20 μm and about 200 μm, between about 20 μm and about 190 μm, between about 20 μm and about 180 μm, between about 20 μm and about 170 μm, between about 20 μm and about 160 μm, between about 20 μm and about 150 μm, between about 20 μm and about 140 μm, between about 20 μm and about 130 μm, between about 20 μm and about 120 μm, between about 20 μm and about 110 μm, between about 20 μm and about 100 μm, between about 20 μm and about 90 μm, between about 20 μm and about 80 μm, between about 20 μm and about 70 μm, between about 20 μm and about 60 μm, between about 20 μm and about 50 μm, between about 20 μm and about 40 μm, between about 20 μm and about 30 μm, between about 30 μm and about 250 μm, between about 30 μm and about 240 μm, between about 30 μm and about 230 μm, between about 30 μm and about 220 μm, between about 30 μm and about 210 μm, between about 30 μm and about 200 μm, between about 30 μm and about 190 μm, between about 30 μm and about 180 μm, between about 30 μm and about 170 μm, between about 30 μm and about 160 μm, between about 30 μm and about 150 μm, between about 30 μm and about 140 μm, between about 30 μm and about 130 μm, between about 30 μm and about 120 μm, between about 30 μm and about 110 μm, between about 30 μm and about 110 μm, between about 30 μm and about 100 μm, between about 30 μm and about 90 μm, between about 30 μm and about 80 μm, between about 30 μm and about 70 μm, between about 30 μm and about 60 μm, between about 30 μm and about 50 μm, between about 30 μm and about 40 μm, between about 40 μm and about 250 μm, between about 40 μm and about 240 μm, between about 40 μm and about 230 μm, between about 40 μm and about 220 μm, between about 40 μm and about 210 μm, between about 40 μm and about 200 μm, between about 40 μm and about 190 μm, between about 40 μm and about 180 μm, between about 40 μm and about 170 μm, between about 40 μm and about 160 μm, between about 40 μm and about 150 μm, between about 40 μm and about 140 μm, between about 40 μm and about 130 μm, between about 40 μm and about 120 μm, between about 40 μm and about 110 μm, between about 40 μm and about 100 μm, between about 40 μm and about 90 μm, between about 40 μm and about 80 μm, between about 40 μm and about 70 μm, between about 40 μm and about 60 μm, between about 40 μm and about 50 μm, between about 50 μm and about 250 μm, between about 50 μm and about 240 μm, between about 50 μm and about 230 μm, between about 50 μm and about 220 μm, between about 50 μm and about 210 μm, between about 50 μm and about 200 μm, between about 50 μm and about 190 μm, between about 50 μm and about 180 μm, between about 50 μm and about 170 μm, between about 50 μm and about 160 μm, between about 50 μm and about 150 μm, between about 50 μm and about 140 μm, between about 50 μm and about 130 μm, between about 50 μm and about 120 μm, between about 50 μm and about 110 μm, between about 50 μm and about 100 μm, between about 50 μm and about 90 μm, between about 50 μm and about 80 μm, between about 50 μm and about 70 μm, between about 50 μm and about 60 μm, between about 60 μm and about 250 μm, between about 60 μm and about 240 μm, between about 60 μm and about 230 μm, between about 60 μm and about 220 μm, between about 60 μm and about 210 μm, between about 60 μm and about 200 μm, between about 60 μm and about 190 μm, between about 60 μm and about 180 μm, between about 60 μm and about 170 μm, between about 60 μm and about 160 μm, between about 60 μm and about 150 μm, between about 60 μm and about 140 μm, between about 60 μm and about 130 μm, between about 60 μm and about 120 μm, between about 60 μm and about 110 μm, between about 60 μm and about 100 μm, between about 60 μm and about 90 μm, between about 60 μm and about 80 μm, between about 60 μm and about 70 μm, between about 70 μm and about 250 μm, between about 70 μm and about 240 μm, between about 70 μm and about 230 μm, between about 70 μm and about 220 μm, between about 70 μm and about 210 μm, between about 70 μm and about 200 μm, between about 70 μm and about 190 μm, between about 70 μm and about 180 μm, between about 70 μm and about 170 μm, between about 70 μm and about 160 μm, between about 70 μm and about 150 μm, between about 70 μm and about 140 μm, between about 70 μm and about 130 μm, between about 70 μm and about 120 μm, between about 70 μm and about 110 μm, between about 70 μm and about 100 μm, between about 70 μm and about 90 μm, between about 70 μm and about 80 μm, between about 80 μm and about 250 μm, between about 80 μm and about 240 μm, between about 80 μm and about 230 μm, between about 80 μm and about 220 μm, between about 80 μm and about 210 μm, between about 80 μm and about 200 μm, between about 80 μm and about 190 μm, between about 80 μm and about 180 μm, between about 80 μm and about 170 μm, between about 80 μm and about 160 μm, between about 80 μm and about 150 μm, between about 80 μm and about 140 μm, between about 80 μm and about 130 μm, between about 80 μm and about 120 μm, between about 80 μm and about 110 μm, between about 80 μm and about 100 μm, between about 80 μm and about 90 μm, between about 90 μm and about 250 μm, between about 90 μm and about 240 μm, between about 90 μm and about 230 μm, between about 90 μm and about 220 μm, between about 90 μm and about 210 μm, between about 90 μm and about 200 μm, between about 90 μm and about 190 μm, between about 90 μm and about 180 μm, between about 90 μm and about 170 μm, between about 90 μm and about 160 μm, between about 90 μm and about 150 μm, between about 90 μm and about 140 μm, between about 90 μm and about 130 μm, between about 90 μm and about 120 μm, between about 90 μm and about 110 μm, between about 90 μm and about 100 μm, between about 100 μm and about 250 μm, between about 100 μm and about 240 μm, between about 100 μm and about 230 μm, between about 100 μm and about 220 μm, between about 100 μm and about 210 μm, between about 100 μm and about 200 μm, between about 100 μm and about 190 μm, between about 100 μm and about 180 μm, between about 100 μm and about 170 μm, between about 100 μm and about 160 μm, between about 100 μm and about 150 μm, between about 100 μm and about 140 μm, between about 100 μm and about 130 μm, between about 100 μm and about 120 μm, between about 100 μm and about 110 μm, between about 110 μm and about 250 μm, between about 110 μm and about 240 μm, between about 110 μm and about 230 μm, between about 110 μm and about 220 μm, between about 110 μm and about 210 μm, between about 110 μm and about 200 μm, between about 100 μm and about 190 μm, between about 100 μm and about 180 μm, between about 100 μm and about 170 μm, between about 100 μm and about 160 μm, between about 100 μm and about 150 μm, between about 100 μm and about 140 μm, between about 100 μm and about 130 μm, between about 100 μm and about 120 μm, between about 100 μm and about 110 μm, between about 110 μm and about 250 μm, between about 110 μm and about 240 μm, between about 110 μm and about 230 μm, between about 110 μm and about 220 μm, between about 110 μm and about 210 μm, between about 110 μm and about 200 μm, between about 110 μm and about 190 μm, between about 110 μm and about 180 μm, between about 110 μm and about 170 μm, between about 110 μm and about 160 μm, between about 110 μm and about 150 μm, between about 110 μm and about 140 μm, between about 110 μm and about 130 μm, between about 110 μm and about 120 μm, between about 120 μm and about 250 μm, between about 120 μm and about 240 μm, between about 120 μm and about 230 μm, between about 120 μm and about 220 μm, between about 120 μm and about 210 μm, between about 120 μm and about 200 μm, between about 120 μm and about 190 μm, between about 120 μm and about 180 μm, between about 120 μm and about 170 μm, between about 120 μm and about 160 μm, between about 120 μm and about 150 μm, between about 120 μm and about 140 μm, between about 120 μm and about 130 μm, between about 130 μm and about 250 μm, between about 130 μm and about 240 μm, between about 130 μm and about 230 μm, between about 130 μm and about 220 μm, between about 130 μm and about 210 μm, between about 130 μm and about 200 μm, between about 130 μm and about 190 μm, between about 130 μm and about 180 μm, between about 130 μm and about 170 μm, between about 130 μm and about 160 μm, between about 130 μm and about 150 μm, between about 130 μm and about 140 μm, between about 140 μm and about 250 μm, between about 140 μm and about 240 μm, between about 140 μm and about 230 μm, between about 140 μm and about 220 μm, between about 140 μm and about 210 μm, between about 140 μm and about 200 μm, between about 140 μm and about 190 μm, between about 140 μm and about 180 μm, between about 140 μm and about 170 μm, between about 140 μm and about 160 μm, between about 140 μm and about 150 μm, between about 150 μm and about 250 μm, between about 150 μm and about 240 μm, between about 150 μm and about 230 μm, between about 150 μm and about 220 μm, between about 150 μm and about 210 μm, between about 150 μm and about 200 μm, between about 150 μm and about 190 μm, between about 150 μm and about 180 μm, between about 150 μm and about 170 μm, between about 150 μm and about 160 μm, between about 160 μm and about 250 μm, between about 160 μm and about 240 μm, between about 160 μm and about 230 μm, between about 160 μm and about 220 μm, between about 160 μm and about 210 μm, between about 160 μm and about 200 μm, between about 160 μm and about 190 μm, between about 160 μm and about 180 μm, between about 160 μm and about 170 μm, between about 170 μm and about 250 μm, between about 170 μm and about 240 μm, between about 170 μm and about 230 μm, between about 170 μm and about 220 μm, between about 170 μm and about 210 μm, between about 170 μm and about 200 μm, between about 170 μm and about 190 μm, between about 170 μm and about 180 μm, between about 180 μm and about 250 μm, between about 180 μm and about 240 μm, between about 180 μm and about 230 μm, between about 180 μm and about 220 μm, between about 180 μm and about 210 μm, between about 180 μm and about 200 μm, between about 180 μm and about 190 μm, between about 190 μm and about 250 μm, between about 190 μm and about 240 μm, between about 190 μm and about 230 μm, between about 190 μm and about 220 μm, between about 190 μm and about 210 μm, between about 190 μm and about 200 μm, between about 200 μm and about 250 μm, between about 200 μm and about 240 μm, between about 200 μm and about 230 μm, between about 200 μm and about 220 μm, between about 200 μm and about 210 μm, between about 210 μm and about 250 μm, between about 210 μm and about 240 μm, between about 210 μm and about 230 μm, between about 210 μm and about 220 μm, between about 220 μm and about 250 μm, between about 220 μm and about 240 μm, between about 220 μm and about 230 μm, between about 230 μm and about 250 μm, between about 230 μm and about 240 μm, or between about 240 μm and about 250 μm).

The one or more pores of the sparger can have a pore type of, e.g., a drilled pore or a sintered pore. The culturing system can include a device for agitating the liquid medium disposed within the vessel (e.g., an impellor and a motor that rotates the impellor). The vessel can include one or more ports (and optionally pumps) that allow for the addition of a material (e.g., a liquid medium, poloxamer-188, base or acid (as needed to regulate pH), and/or antifoam) to the liquid medium disposed in the vessel and/or the removal of liquid medium (e.g., a clarified liquid medium or a sample of cell culture). The culturing system can also include one or more sensors for monitoring the pH, $dO_2$, temperature, and $dCO_2$ in the liquid medium during a culturing period. The culturing system can include a filtration device (e.g., a device that performs alternating tangential filtration or tangential flow filtration) that processes a volume of cell culture to provide a clarified liquid medium that is substantially free of cells. The culturing system can include a heating/cooling device that allows for regulation of the temperature of the liquid medium disposed in the vessel. Additional features of cell culture systems are well known in the art.

Perfusion Culturing

In any of the methods described herein, the culturing step can be perfusion culturing. As is known in the art, perfusion culturing includes removing from a bioreactor a first volume of a first liquid medium, and adding to the bioreactor a second volume of a second liquid medium, wherein the first volume and the second volume are about equal. The mammalian cells are retained in the bioreactor by some cell retention device or through techniques, such as cell settling in a settling cone.

As is known in the art, perfusion culturing is different than feed batch culturing, and the culture media and/or the culturing conditions used in perfusion culturing are often different than those used in feed batch culturing.

The removal and addition of media in perfusion culturing can be performed simultaneously or sequentially, or some combination of the two. Further, removal and addition can be performed continuously, such as at a rate that removes and replaces a volume of between 0.1% to 800%, between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, or between 4% and 30% of the volume of the bioreactor.

The first volume of the first liquid medium removed and the second volume of the second liquid medium added can in some instances be held approximately the same over each 24-hour period. As is known in the art, the rate at which the first volume of the first liquid medium is removed (volume/unit of time) and the rate at which the second volume of the second liquid medium is added (volume/unit of time) can be varied and depends on the conditions of the particular cell culture system. The rate at which the first volume of the first liquid medium is removed (volume/unit of time) and the rate at which the second volume of the second liquid medium is added (volume/unit of time) can be about the same or can be different.

Alternatively, the volume removed and added can change by gradually increasing over each 24-hour period. For example, the volume of the first liquid medium removed and the volume of the second liquid medium added within each 24-hour period can be increased over the culturing period. The volume can be increased over the culturing period from a volume that is between 0.5% to about 20% of the bioreactor volume. The volume can be increased over the culturing period to about 25% to about 150% of the bioreactor capacity or the volume of the cell culture at the start of the culturing period.

In some examples of the methods described herein, after the first 48 to 96 hours of the culturing period, in each 24-hour period (within the culturing period), the first volume of the first liquid medium removed and the second volume of the second liquid medium added is about 10% to about 95%, about 10% to about 20%, about 20% to about 30%, about 30% to about 40%, about 40% to about 50%, about 50% to about 60%, about 60% to about 70%, about 70% to about 80%, about 80% to about 90%, about 85% to about 95%, about 60% to about 80%, or about 70% of the volume of the cell culture at the start of the culturing period.

Skilled practitioners will appreciate that the first liquid medium and the second liquid medium can be the same type of media. In other instances, the first liquid medium and the second liquid medium can be different. The second liquid medium may be more concentrated with respect to one or more media components.

The first volume of the first liquid medium can be removed by using any automated system. For example alternating tangential flow filtration may be used. Alternatively, the first volume of the first liquid medium can be removed by seeping or gravity flow of the first volume of the first liquid medium through a sterile membrane with a molecular weight cut-off that excludes the mammalian cell. Alternatively, the first volume of the first liquid medium can be removed by stopping or significantly decreasing the rate of agitation for a period of at least 1 minute, at least 2 minutes, 3 minutes, 4 minutes, 5 minutes, 10 minutes, 15 minutes, 20 minutes, 25 minutes, 30 minutes, 40 minutes, 50 minutes, or 1 hour, and removing or aspirating the first volume of the first liquid medium from the top of the bioreactor.

The second volume of the second liquid medium can be added to the first liquid medium by a pump. The second liquid medium can be added to the first liquid medium manually, such as by pipetting or injecting the second volume of the second liquid medium directly onto the first liquid medium or in an automated fashion.

In some embodiments of the methods described herein include (optionally providing a vessel containing mammalian cells disposed in a first liquid medium and) incubating the vessel with agitation and for a culturing period of at least about 7 days at a temperature between about 32° C. to about 40° C.; and continuously or periodically after the first 48 to 96 hours of the culturing period removing a first volume of the first liquid medium and adding to the first liquid medium a second volume of a second liquid medium, where the first and second volumes are about equal. In some embodiments, after about the first 48 to 96 hours of the culturing period, in each 24-hour period, the first volume of the first liquid medium removed and the second volume of the second liquid medium added is about 0.3× to about 10× of the volume of the first liquid medium or the volume of the vessel.

Some examples of perfusion culturing include incubating a culturing system containing a first liquid medium with agitation and for a culturing period of at least about 7 days at a temperature between about 32° C. to about 40° C.; and continuously or periodically after the first 48 to 96 hours of the culturing period removing a first volume of the first liquid medium and adding to the first liquid medium a second volume of a second liquid medium.

Fed Batch Culturing

The culturing step in the methods described herein can include fed batch culturing. As is known in the art, fed batch culturing includes the incremental or continuous addition of a feed liquid medium to an initial cell culture without substantial or significant removal of the first liquid medium from the cell culture. In some instances, the feed liquid medium is the same as the first liquid medium. The feed medium may be either in a liquid form (a feed liquid medium) or a dry powder. In other instances, the feed liquid medium is a concentrated form of the first liquid medium and/or is added as a dry powder.

The feed liquid medium can be added to the initial cell culture at a specific time point or at multiple time points during the culturing period. For example, the feed liquid medium can be added to the initial cell culture at a time point that is between 6 hours and 7 days, between about 6 hours and about 6 days, between about 6 hours and about 5 days, between about 6 hours and about 4 days, between about 6 hours and about 3 days, between about 6 hours and about 2 days, between about 6 hours and about 1 day, between about 12 hours and about 7 days, between about 12 hours and about 6 days, between about 12 hours and about 5 days, between about 12 hours and about 4 days, between about 12 hours and about 3 days, between about 12 hours and about 2 days, between about 1 day and about 7 days, between about 1 day and about 6 days, between about 1 day and about 5 days, between about 1 day and about 4 days, between about 1 day and about 3 days, between about 1 day and about 2 days, between about 2 days and about 7 days, between about 2 days and about 6 days, between about 2 days and about 5 days, between about 2 days and about 4 days, between about 2 days and about 3 days, between about 3 days and about 7 days, between about 3 days and about 6 days, between about 3 days and about 5 days, between about 3 days and about 4 days, between about 4 days and about 7 days, between about 4 days and about 6 days, between about 4 days and about 5 days, between about 5 days and about 7 days, or between about 5 days and about 6 days, after the start of culturing period.

The feed liquid medium can be continuously added to the initial cell culture, or can be added periodically (e.g., daily) to the initial cell culture during the culturing period. In some examples when the feed liquid medium is added periodically to the initial cell culture, the feed liquid medium can be added once, twice, three times, four times, or five times. The volume of a feed liquid medium or the amount of a feed solid medium added to the initial cell culture can change (e.g., increase) during the culturing period. The volume of a feed liquid medium added to the initial cell culture over any 24 hour period during the culturing period can be some fraction of the capacity of the bioreactor. The volume of a feed liquid medium added to the initial cell culture over any 24 hour period during the culturing period can be between 0.01× and about 0.3× (e.g., between about 0.01× and about 0.28×, between about 0.01× and about 0.26×, between about 0.01× and about 0.24×, between about 0.01× and about 0.22×, between about 0.01× and about 0.20×, between about 0.01× and about 0.18×, between about 0.01× and about 0.16×, between about 0.01× and about 0.14×, between about 0.01× and about 0.12×, between about 0.01× and about 0.10×, between about 0.01× and about 0.08×, between about 0.01× and about 0.06×, between about 0.01× and about 0.04×, between about 0.025× and about 0.3×, between about 0.025× and about 0.28×, between about 0.025× and about 0.26×, between about 0.025× and about 0.24×, between about 0.025× and about 0.22×, between about 0.025× and about 0.20×, between about 0.025× and about 0.18×, between about 0.025× and about 0.16×, between about 0.025× and about 0.14×, between about 0.025× and about 0.12×, between about 0.025× and about 0.10×, between about 0.025× and about 0.08×, between about 0.025× and about 0.06×, between about 0.025× and about 0.04×, between about 0.05× and about 0.3×, between about 0.05× and about 0.28×, between about 0.05× and about 0.26×, between about 0.05× and about 0.24×, between about 0.05× and about 0.22×, between about 0.05× and about 0.20×, between about 0.05× and about 0.18×, between about 0.05× and about 0.16×, between about 0.05× and about 0.14×, between about 0.05× and about 0.12×, between about 0.05× and about 0.10×, between about 0.1× and about 0.3×, between about 0.1× and about 0.28×, between about 0.1× and about 0.26×, between about 0.1× and about 0.24×, between about 0.1× and about 0.22×, between about 0.1× and about 0.20×, between about 0.1× and about 0.18×, between about 0.1× and about 0.16× between about 0.1× and about 0.14×, between about 0.1×, between about 0.15× and about 0.3×, between about 0.15× and about 0.2×, between about 0.2× and about 0.3×, or between about 0.25× and about 0.3×) of the capacity of a bioreactor containing the culture.

In other embodiments, the volume of a feed liquid medium added to the initial cell culture over any 24 hour period in the culturing period can be between 0.02× and about 1.0× (e.g., between about 0.02× and about 0.9×, between about 0.02× and about 0.8×, between about 0.02× and about 0.7×, between about 0.02× and about 0.6×, between about 0.02× and about 0.5×, between about 0.02× and about 0.4×, between about 0.02× and about 0.3×, between about 0.02× and about 0.2×, between about 0.02× and about 0.1×, between about 0.05× and about 1.0×, between about 0.05× and about 0.8×, between about 0.05× and about 0.7×, between about 0.05× and about 0.6×, between about 0.05× and about 0.5×, between about 0.05× and about 0.4×, between about 0.05× and about 0.3×, between about 0.05× and about 0.2×, between about 0.05× and about 0.1×, between about 0.1× and about 1.0×, between about 0.1× and about 0.9×, between about 0.1× and about 0.8×, between about 0.1× and about 0.7×, between about 0.1× and about 0.6×, between about 0.1× and about 0.5×, between about 0.1× and about 0.4×, between about 0.1× and about 0.3×, between about 0.1× and about 0.2×, between about 0.2× and about 1.0×, between about 0.2× and about 0.9×, between about 0.2× and about 0.8×, between about 0.2× and about 0.7×, between about 0.2× and about 0.6×, between about 0.2× and about 0.5×, or between about 0.2× and about 0.4×) of the volume of the cell culture at the start of the culturing period.

Poloxamer-188

Poloxamer-188 is a molecule known in the art. Poloxamer-188 is a non-ionic synthetic block copolymer of ethylene oxide and propylene oxide. Poloxamer-188 has an average molecular weight of between about 7680 to about 9510, and about 81.8%±1.9% of its composition by weight is represented by oxyethylene. For example, poloxamer-188 has the structure shown in Formula I below, where a is 80 and b is 27. Poloxamer-188 has a CAS number of 9003-11-6.

(Formula I)

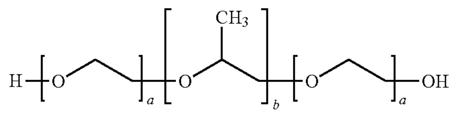

Poloxamer-188 is commercially available from a number of different vendors including, e.g., Sigma-Aldrich (St. Louis, MO), Mediatech, Inc. (Manassas, VA), MAST Therapeutics, Inc. (San Diego, CA), EMD Millipore (Billerica, MA), BASF (Ludwigshafen, Germany), Pluronic® F-68 Life Technologies (Carlsbad, CA), and PhytoTechnology Laboratories, LLC (Shawnee Mission, KS).

The methods provided herein include culturing a mammalian cell (e.g., a mammalian cell including a recombinant protein-encoding nucleic acid) in a liquid medium that includes poloxamer-188 at a concentration of about 1.8 g/L or at a greater concentration than 1.8 g/L (e.g., a concentration of about 1.9 g/L or a greater concentration than 1.9 g/L, a concentration of about 2.0 g/L or a greater concentration than 2.0 g/L, a concentration of about 2.1 g/L or a greater concentration than 2.1 g/L, a concentration of about 2.2 g/L or a greater concentration than 2.2 g/L, a concentration of about 2.3 g/L or a greater concentration than 2.3 g/L, a concentration of about 2.4 g/L or a greater concentration than 2.4 g/L, a concentration of about 2.5 g/L or a greater concentration than 2.5 g/L, a concentration of about 2.6 g/L or a greater concentration than 2.6 g/L, a concentration of about 2.7 g/L or a greater concentration than 2.7 g/L, a concentration of about 2.8 g/L or a greater concentration than 2.8 g/L, a concentration of about 2.9 g/L or a greater concentration than 2.9 g/L, a concentration of about 3.0 g/L or a greater concentration than 3.0 g/L, a concentration of about 3.1 g/L or a greater concentration than 3.1 g/L, a concentration of about 3.2 g/L or a greater concentration than 3.2 g/L, a concentration of about 3.3 g/L or a greater concentration than 3.3 g/L, a concentration of about 3.4 g/L or a greater concentration than 3.4 g/L, a concentration of about 3.5 g/L or a greater concentration than 3.5 g/L, a concentration of about 3.6 g/L or a greater concentration than 3.6 g/L, a concentration of about 3.7 g/L or a greater concentration than 3.7 g/L, a concentration of about 3.8 g/L or a greater concentration than 3.8 g/L, a concentration of about 3.9 g/L or a greater concentration than 3.9 g/L, a concentration of about 4.0 g/L or a greater concentration than 4.0 g/L, a concentration of about 4.1 g/L or a greater concentration than 4.1 g/L, a concentration of about 4.2 g/L or a greater concentration than 4.2 g/L, a concentration of about 4.3 g/L or a greater concentration than 4.3 g/L, a concentration of about 4.4 g/L or a greater concentration than 4.4 g/L, a concentration of about 4.5 g/L or a greater concentration than 4.5 g/L, a concentration of about 4.6 g/L or a greater concentration than 4.6 g/L, a concentration of about 4.7 g/L or a greater concentration than 4.7 g/L, a concentration of about 4.8 g/L or a greater concentration than 4.8 g/L, a concentration of about 4.9 g/L or a greater concentration than 4.9 g/L, a concentration of about 5.0 g/L or a greater concentration than 5.0 g/L, a concentration of about 5.1 g/L or a greater concentration than 5.1 g/L, a concentration of about 5.2 g/L or a greater concentration than 5.2 g/L, a concentration of about 5.3 g/L or a greater concentration than 5.3 g/L, a concentration of about 5.4 g/L or a greater concentration than 5.4 g/L, a concentration of about 5.5 g/L or a greater concentration than 5.5 g/L, a concentration of about 5.6 g/L or a greater concentration than 5.6 g/L, a concentration of about 5.7 g/L or a greater concentration than 5.7 g/L, a concentration of about 5.8 g/L or a greater concentration than 5.8 g/L, a concentration of about 5.9 g/L or a greater concentration than 5.9 g/L, a concentration of about 6.0 g/L or a greater concentration than 6.0 g/L, a concentration of about 6.1 g/L or a greater concentration than 6.1 g/L, a concentration of about 6.2 g/L or a greater concentration than 6.2 g/L, a concentration of about 6.3 g/L or a greater concentration than 6.3 g/L, a concentration of about 6.4 g/L or a greater concentration than 6.4 g/L, a concentration of about 6.5 g/L or a greater concentration than 6.5 g/L, a concentration of about 6.6 g/L or a greater concentration than 6.6 g/L, a concentration of about 6.7 g/L or a greater concentration than 6.7 g/L, a concentration of about 6.8 g/L or a greater concentration than 6.8 g/L, a concentration of about 6.9 g/L or a greater concentration than 6.9 g/L, a concentration of about 7.0 g/L or a greater concentration than 7.0 g/L, a concentration of about 7.1 g/L or a greater concentration than 7.1 g/L, a concentration of about 7.2 g/L or a greater concentration than 7.2 g/L, a concentration of about 7.3 g/L or a greater concentration than 7.3 g/L, a concentration of about 7.4 g/L or a greater concentration than 7.4 g/L, a concentration of about 7.5 g/L or a greater concentration than 7.5 g/L, a concentration of about 7.6 g/L or a greater concentration than 7.6 g/L, a concentration of about 7.7 g/L or a greater concentration than 7.7 g/L, a concentration of about 7.8 g/L or a greater concentration than 7.8 g/L, a concentration of about 7.9 g/L or a greater concentration than 7.9 g/L, a concentration of about 8.0 g/L or a greater concentration than 8.0 g/L, a concentration of about 8.1 g/L or a greater concentration than 8.1 g/L, a concentration of about 8.2 g/L or a greater concentration than 8.2 g/L, a concentration of about 8.3 g/L or a greater concentration than 8.3 g/L, a concentration of about 8.4 g/L or a greater concentration than 8.4 g/L, a concentration of about 8.5 g/L or a greater concentration than 8.5 g/L, a concentration of about 8.6 g/L or a greater concentration than 8.6 g/L, a concentration of about 8.7 g/L or a greater concentration than 8.7 g/L, a concentration of about 8.8 g/L or a greater concentration than 8.8 g/L, a concentration of about 8.9 g/L or a greater concentration than 8.9 g/L, a concentration of about 9.0 g/L or a greater concentration than 9.0 g/L, a concentration of about 9.1 g/L or a greater concentration than 9.1 g/L, a concentration of about 9.2 g/L or a greater concentration than 9.2 g/L, a concentration of about 9.3 g/L or a greater concentration than 9.3 g/L, a concentration of about 9.4 g/L or a greater concentration than 9.4 g/L, a concentration of about 9.5 g/L or a greater concentration than 9.5 g/L, a concentration of about 9.6 g/L or a greater concentration than 9.6 g/L, a concentration of about 9.7 g/L or a greater concentration than 9.7 g/L, a concentration of about 9.8 g/L or a greater concentration than 9.8 g/L, a concentration of about 9.9 g/L or a greater concentration than 9.9 g/L, a concentration of about 10.0 g/L or a greater concentration than 10.0 g/L, a concentration of about 10.1 g/L or a greater concentration than 10.1 g/L, a concentration of about 10.2 g/L or a greater concentration than 10.2 g/L, a concentration of about 10.3 g/L or a greater concentration than 10.3 g/L, a concentration of about 10.4 g/L or a greater concentration than 10.4 g/L, a concentration of about 10.5 g/L or a greater concentration than 10.5 g/L, a concentration of about 10.6 g/L or a greater concentration than 10.6 g/L, a concentration of about 10.7 g/L or a greater concentration than 10.7 g/L, a concentration of about 10.8 g/L or a greater concentration than 10.8 g/L, a concentration of about 10.9 g/L or a greater concentration than 10.9 g/L, a concentration of about 11.0 g/L or a greater concentration than 11.0 g/L, a concentration of about 11.1 g/L or a greater concentration than 11.1 g/L, a concentration of about 11.2 g/L or a greater concentration than 11.2 g/L, a concentration of about 11.3 g/L or a greater concentration than 11.3 g/L, a concentration of about 11.4 g/L or a greater concentration than 11.4 g/L, a concentration of about 11.5 g/L or a greater concentration than 11.5 g/L, a concentration of about 11.6 g/L or a greater concentration than 11.6 g/L, a concentration of about 11.7 g/L or a greater concentration than 11.7 g/L, a concentration of about 11.8 g/L or a greater concentration than 11.8 g/L, a concentration of about 11.9 g/L or a greater concentration than 11.9 g/L, a concentration of about 12.0 g/L or a greater concentration than 12.0 g/L, a concentration of about 12.1 g/L or a greater concentration than 12.1 g/L, a concentration of about 12.2 g/L or a greater concentration than 12.2 g/L, a concentration of about 12.3 g/L or a greater concentration than 12.3 g/L, a concentration of about 12.4 g/L or a greater concentration than 12.4 g/L, a concentration of about 12.5 g/L or a greater concentration than 12.5 g/L, a concentration of about 12.6 g/L or a greater concentration than 12.6 g/L, a concentration of about 12.7 g/L or a greater concentration than 12.7 g/L, a concentration of about 12.8 g/L or a greater concentration than 12.8 g/L, a concentration of about 12.9 g/L or a greater concentration than 12.9 g/L, a concentration of about 13.0 g/L or a greater concentration than 13.0 g/L, a concentration of about 13.1 g/L or a greater concentration than 13.1 g/L, a concentration of about 13.2 g/L or a greater concentration than 13.2 g/L, a concentration of about 13.3 g/L or a greater concentration than 13.3 g/L, a concentration of about 13.4 g/L or a greater concentration than 13.4 g/L, a concentration of about 13.5 g/L or a greater concentration than 13.5 g/L, a concentration of about 13.6 g/L or a greater concentration than 13.6 g/L, a concentration of about 13.7 g/L or a greater concentration than 13.7 g/L, a concentration of about 13.8 g/L or a greater concentration than 13.8 g/L, a concentration of about 13.9 g/L or a greater concentration than 13.9 g/L, a concentration of about 14.0 g/L or a greater concentration than 14.0 g/L, a concentration of about 14.1 g/L or a greater concentration than 14.1 g/L, a concentration of about 14.2 g/L or a greater concentration than 14.2 g/L, a concentration of about 14.3 g/L or a greater concentration than 14.3 g/L, a concentration of about 14.4 g/L or a greater concentration than 14.4 g/L, a concentration of about 14.5 g/L or a greater concentration than 14.5 g/L, a concentration of about 14.6 g/L or a greater concentration than 14.6 g/L, a concentration of about 14.7 g/L or a greater concentration than 14.7 g/L, a concentration of about 14.8 g/L or a greater concentration than 14.8 g/L, a concentration of about 14.9 g/L or a greater concentration than 14.9 g/L, or a concentration of about 15.0 g/L or a greater concentration than 15.0 g/L).

In some embodiments, the methods provided herein include culturing a mammalian cell (e.g., a mammalian cell including a recombinant protein-encoding nucleic acid) in a liquid medium that includes poloxamer-188 at a concentration of between about 1.8 g/L and about 16.0 g/L (e.g., between about 1.8 g/L and about 15.8 g/L, between about 1.8 g/L and about 15.6 g/L, between about 1.8 g/L and about 15.4 g/L, between about 1.8 g/L and about 15.2 g/L, between about 1.8 g/L and about 15.0 g/L, between about 1.8 g/L and about 14.8 g/L, between about 1.8 g/L and about 14.6 g/L, between about 1.8 g/L and about 14.4 g/L, between about 1.8 g/L and about 14.2 g/L, between about 1.8 g/L and about 14.0 g/L, between about 1.8 g/L and about 13.8 g/L, between about 1.8 g/L and about 13.6 g/L, between about 1.8 g/L and about 13.4 g/L, between about 1.8 g/L and about 13.2 g/L, between about 1.8 g/L and about 13.0 g/L, between about 1.8 g/L and about 12.8 g/L, between about 1.8 g/L and about 12.6 g/L, between about 1.8 g/L and about 12.4 g/L, between about 1.8 g/L and about 12.2 g/L, between about 1.8 g/L and about 12.0 g/L, between about 1.8 g/L and about 11.8 g/L, between about 1.8 g/L and about 11.6 g/L, between about 1.8 g/L and about 11.4 g/L, between about 1.8 g/L and about 11.2 g/L, between about 1.8 g/L and about 11.0 g/L, between about 1.8 g/L and about 10.8 g/L, between about 1.8 g/L and about 10.6 g/L, between about 1.8 g/L and about 10.4 g/L, between about 1.8 g/L and about 10.2 g/L, between about 1.8 g/L and about 10.0 g/L, between about 1.8 g/L and about 9.8 g/L, between about 1.8 g/L and about 9.6 g/L, between about 1.8 g/L and about 9.4 g/L, between about 1.8 g/L and about 9.2 g/L, between about 1.8 g/L and about 9.0 g/L, between about 1.8 g/L and about 8.8 g/L, between about 1.8 g/L and about 8.6 g/L, between about 1.8 g/L and about 8.4 g/L, between about 1.8 g/L and about 8.2 g/L, between about 1.8 g/L and about 8.0 g/L, between about 1.8 g/L and about 7.8 g/L, between about 1.8 g/L and about 7.6 g/L, between about 1.8 g/L and about 7.4 g/L, between about 1.8 g/L and about 7.2 g/L, between about 1.8 g/L and about 7.0 g/L, between about 1.8 g/L and about 6.8 g/L, between about 1.8 g/L and about 6.6 g/L, between about 1.8 g/L and about 6.4 g/L, between 1.8 g/L and about 6.2 g/L, between about 1.8 g/L and about 6.0 g/L, between about 1.8 g/L and about 5.8 g/L, between about 1.8 g/L and about 5.6 g/L, between about 1.8 g/L and about 5.4 g/L, between about 1.8 g/L and about 5.2 g/L, between about 1.8 g/L and about 5.0 g/L, between about 1.8 g/L and about 4.8 g/L, between about 1.8 g/L and about 4.6 g/L, between about 1.8 g/L and about 4.4 g/L, between about 1.8 g/L and about 4.2 g/L, between about 1.8 g/L and about 4.0 g/L, between about 1.8 g/L and about 3.8 g/L, between about 1.8 g/L and about 3.6 g/L, between about 1.8 g/L and about 3.4 g/L, between about 1.8 g/L and about 3.2 g/L, between about 1.8 g/L and about 3.0 g/L, between about 1.8 g/L and about 2.8 g/L, between about 2.0 g/L and about 16.0 g/L, between about 2.0 g/L and about 15.8 g/L, between about 2.0 g/L and about 15.6 g/L, between about 2.0 g/L and about 15.4 g/L, between about 2.0 g/L and about 15.2 g/L, between about 2.0 g/L and about 15.0 g/L, between about 2.0 g/L and about 14.8 g/L, between about 2.0 g/L and about 14.6 g/L, between about 2.0 g/L and about 14.4 g/L, between about 2.0 g/L and about 14.2 g/L, between about 2.0 g/L and about 14.0 g/L, between about 2.0 g/L and about 13.8 g/L, between about 2.0 g/L and about 13.6 g/L, between about 2.0 g/L and about 13.4 g/L, between about 2.0 g/L and about 13.2 g/L, between about 2.0 g/L and about 13.0 g/L, between about 2.0 g/L and about 12.8 g/L, between about 2.0 g/L and about 12.6 g/L, between about 2.0 g/L and about 12.4 g/L, between about 2.0 g/L and about 12.2 g/L, about 2.0 g/L and about 12.0 g/L, between about 2.0 g/L and about 11.8 g/L, between about 2.0 g/L and about 11.6 g/L, between about 2.0 g/L and about 11.4 g/L, between about 2.0 g/L and about 11.2 g/L, between about 2.0 g/L and about 11.0 g/L, between about 2.0 g/L and about 10.8 g/L, between about 2.0 g/L and about 10.6 g/L, between about 2.0 g/L and about 10.4 g/L, between about 2.0 g/L and about 10.2 g/L, between about 2.0 g/L and about 10.0 g/L, between about 2.0 g/L and about 9.8 g/L, between about 2.0 g/L and about 9.6 g/L, between about 2.0 g/L and about 9.4 g/L, between about 2.0 g/L and about 9.2 g/L, between about 2.0 g/L and about 9.0 g/L, between about 2.0 g/L and about 8.8 g/L, between about 2.0 g/L and about 8.6 g/L, between about 2.0 g/L and about 8.4 g/L, between about 2.0 g/L and about 8.2 g/L, between about 2.0 g/L and about 8.0 g/L, between about 2.0 g/L and about 7.8 g/L, between about 2.0 g/L and about 7.6 g/L, between about 2.0 g/L and about 7.4 g/L, between about 2.0 g/L and about 7.2 g/L, between about 2.0 g/L and about 7.0 g/L, between about 2.0 g/L and about 6.8 g/L, between about 2.0 g/L and about 6.6 g/L, between about 2.0 g/L and about 6.4 g/L, between about 2.0 g/L and about 6.2 g/L, between about 2.0 g/L and about 6.0 g/L, between about 2.0 g/L and about 5.8 g/L, between about 2.0 g/L and about 5.6 g/L, between about 2.0 g/L and about 5.4 g/L, between about 2.0 g/L and about 5.2 g/L, between about 2.0 g/L and about 5.0 g/L, between about 2.0 g/L and about 4.8 g/L, between about 2.0 g/L and about 4.6 g/L, between about 2.0 g/L and about 4.4 g/L, between about 2.0 g/L and about 4.2 g/L, between about 2.0 g/L and about 4.0 g/L, between about 2.0 g/L and about 3.8 g/L, between about 2.0 g/L and about 3.6 g/L, between about 2.0 g/L and about 3.4 g/L, between about 2.0 g/L and about 3.2 g/L, between about 2.0 g/L and about 3.0 g/L, between about 2.2 g/L and about 16.0 g/L, between about 2.2 g/L and about 15.8 g/L, between about 2.2 g/L and about 15.6 g/L, between about 2.2 g/L and about 15.4 g/L, between about 2.2 g/L and about 15.2 g/L, between about 2.2 g/L and about 15.0 g/L, between about 2.2 g/L and about 14.8 g/L, between about 2.2 g/L and about 14.6 g/L, between about 2.2 g/L and about 14.4 g/L, between about 2.2 g/L and about 14.2 g/L, between about 2.2 g/L and about 14.0 g/L, between about 2.2 g/L and about 13.8 g/L, between about 2.2 g/L and about 13.6 g/L, between about 2.2 g/L and about 13.4 g/L, between about 2.2 g/L and about 13.2 g/L, between about 2.2 g/L and about 13.0 g/L, between about 2.2 g/L and about 12.8 g/L, between about 2.2 g/L and about 12.6 g/L, between about 2.2 g/L and about 12.4 g/L, between about 2.2 g/L and about 12.2 g/L, between about 2.2 g/L and about 12.0 g/L, between about 2.2 g/L and about 11.8 g/L, between about 2.2 g/L and about 11.6 g/L, between about 2.2 g/L and about 11.4 g/L, between about 2.2 g/L and about 11.2 g/L, between about 2.2 g/L and about 11.0 g/L, between about 2.2 g/L and about 10.8 g/L, between about 2.2 g/L and about 10.6 g/L. between about 2.2 g/L and about 10.4 g/L, between about 2.2 g/L and about 10.2 g/L, between about 2.2 g/L and about 10.0 g/L, between about 2.2 g/L and about 9.8 g/L, between about 2.2 g/L and about 9.6 g/L, between about 2.2 g/L and about 9.4 g/L, between about 2.2 g/L and about 9.2 g/L, between about 2.2 g/L and about 9.0 g/L, between about 2.2 g/L and about 8.8 g/L, between about 2.2 g/L and about 8.6 g/L, between about 2.2 g/L and about 8.4 g/L, between about 2.2 g/L and about 8.2 g/L, between about 2.2 g/L and about 8.0 g/L, between about 2.2 g/L and about 7.8 g/L, between about 2.2 g/L and about 7.6 g/L, between about 2.2 g/L and about 7.4 g/L, between about 2.2 g/L and about 7.2 g/L, between about 2.2 g/L and about 7.0 g/L, between about 2.2 g/L and about 6.9 g/L, between about 2.2 g/L and about 6.8 g/L, between about 2.2 g/L and about 6.6 g/L, between about 2.2 g/L and about 6.4 g/L, between about 2.2 g/L and about 6.2 g/L, between about 2.2 g/L and about 6.0 g/L, between about 2.2 g/L and about 5.8 g/L, between about 2.2 g/L and about 5.6 g/L, between about 2.2 g/L and about 5.4 g/L, between about 2.2 g/L and about 5.2 g/L, between about 2.2 g/L and about 5.0 g/L, between about 2.2 g/L and about 4.8 g/L, between about 2.2 g/L and about 4.6 g/L, between about 2.2 g/L and about 4.4 g/L, between about 2.2 g/L and about 4.2 g/L, between about 2.2 g/L and about 4.0 g/L, between about 2.2 g/L and about 3.8 g/L, between about 2.2 g/L and about 3.6 g/L, between about 2.2 g/L and about 3.4 g/L, between about 2.2 g/L and about 3.2 g/L, between about 2.4 g/L and about 16.0 g/L, between about 2.4 g/L and about 15.8 g/L, between about 2.4 g/L and about 15.6 g/L, between about 2.4 g/L and about 15.4 g/L, between about 2.4 g/L and about 15.2 g/L, between about 2.4 g/L and about 15.0 g/L, between about 2.4 g/L and about 14.8 g/L, between about 2.4 g/L and about 14.6 g/L, between about 2.4 g/L and about 14.4 g/L, between about 2.4 g/L and about 14.2 g/L, between about 2.4 g/L and about 14.0 g/L, between about 2.4 g/L and about 13.8 g/L, between about 2.4 g/L and about 13.6 g/L, between about 2.4 g/L and about 13.4 g/L, between about 2.4 g/L and about 13.2 g/L, between about 2.4 g/L and about 13.0 g/L, between about 2.4 g/L and about 12.8 g/L, between about 2.4 g/L and about 12.6 g/L, between about 2.4 g/L and about 12.4 g/L, between about 2.4 g/L and about 12.2 g/L, between about 2.4 g/L and about 12.0 g/L, between about 2.4 g/L and about 11.8 g/L, between about 2.4 g/L and about 11.6 g/L, between about 2.4 g/L and about 11.4 g/L, between about 2.4 g/L and about 11.2 g/L, between about 2.4 g/L and about 11.0 g/L, between about 2.4 g/L and about 10.8 g/L, between about 2.4 g/L and about 10.6 g/L. between about 2.4 g/L and about 10.4 g/L, between about 2.4 g/L and about 10.2 g/L, between about 2.4 g/L and about 10.0 g/L, between about 2.4 g/L and about 9.8 g/L, between about 2.4 g/L and about 9.6 g/L, between about 2.4 g/L and about 9.4 g/L, between about 2.4 g/L and about 9.2 g/L, between about 2.4 g/L and about 9.0 g/L, between about 2.4 g/L and about 8.8 g/L, between about 2.4 g/L and about 8.6 g/L, between about 2.4 g/L and about 8.4 g/L, between about 2.4 g/L and about 8.2 g/L, between about 2.4 g/L and about 8.0 g/L, between about 2.4 g/L and about 7.8 g/L, between about 2.4 g/L and about 7.6 g/L, between about 2.4 g/L and about 7.4 g/L, between about 2.4 g/L and about 7.2 g/L, between about 2.4 g/L and about 7.0 g/L, between about 2.4 g/L and about 6.9 g/L, between about 2.4 g/L and about 6.8 g/L, between about 2.4 g/L and about 6.6 g/L, between about 2.4 g/L and about 6.4 g/L, between about 2.4 g/L and about 6.2 g/L, between about 2.4 g/L and about 6.0 g/L, between about 2.4 g/L and about 5.8 g/L, between about 2.4 g/L and about 5.6 g/L, between about 2.4 g/L and about 5.4 g/L, between about 2.4 g/L and about 5.2 g/L, between about 2.4 g/L and about 5.0 g/L, between about 2.4 g/L and about 4.8 g/L, between about 2.4 g/L and about 4.6 g/L, between about 2.4 g/L and about 4.4 g/L, between about 2.4 g/L and about 4.2 g/L, between about 2.4 g/L and about 4.0 g/L, between about 2.4 g/L and about 3.8 g/L, between about 2.4 g/L and about 3.6 g/L, between about 2.4 g/L and about 3.4 g/L, between about 2.6 g/L and about 16.0 g/L, between about 2.6 g/L and about 15.8 g/L, between about 2.6 g/L and about 15.6 g/L, between about 2.6 g/L and about 15.4 g/L, between about 2.6 g/L and about 15.2 g/L, between about 2.6 g/L and about 15.0 g/L, between about 2.6 g/L and about 14.8 g/L, between about 2.6 g/L and about 14.6 g/L, between about 2.6 g/L and about 14.4 g/L, between about 2.6 g/L and about 14.2 g/L, between about 2.6 g/L and about 14.0 g/L, between about 2.6 g/L and about 13.8 g/L, between about 2.6 g/L and about 13.6 g/L, between about 2.6 g/L and about 13.4 g/L, between about 2.6 g/L and about 13.2 g/L, between about 2.6 g/L and about 13.0 g/L, between about 2.6 g/L and about 12.8 g/L, between about 2.6 g/L and about 12.6 g/L, between about 2.6 g/L and about 12.4 g/L, between about 2.6 g/L and about 12.2 g/L, between about 2.6 g/L and about 12.0 g/L, between about 2.6 g/L and about 11.8 g/L, between about 2.6 g/L and about 11.6 g/L, between about 2.6 g/L and about 11.4 g/L, between about 2.6 g/L and about 11.2 g/L, between about 2.6 g/L and about 11.0 g/L, between about 2.6 g/L and about 10.8 g/L, between about 2.6 g/L and about 10.6 g/L. between about 2.6 g/L and about 10.4 g/L, between about 2.6 g/L and about 10.2 g/L, between about 2.6 g/L and about 10.0 g/L, between about 2.6 g/L and about 9.8 g/L, between about 2.6 g/L and about 9.6 g/L, between about 2.6 g/L and about 9.4 g/L, between about 2.6 g/L and about 9.2 g/L, between about 2.6 g/L and about 9.0 g/L, between about 2.6 g/L and about 8.8 g/L, between about 2.6 g/L and about 8.6 g/L, between about 2.6 g/L and about 8.4 g/L, between about 2.6 g/L and about 8.2 g/L, between about 2.6 g/L and about 8.0 g/L, between about 2.6 g/L and about 7.8 g/L, between about 2.6 g/L and about 7.6 g/L, between about 2.6 g/L and about 7.4 g/L, between about 2.6 g/L and about 7.2 g/L, between about 2.6 g/L and about 7.0 g/L, between about 2.6 g/L and about 6.9 g/L, between about 2.6 g/L and about 6.8 g/L, between about 2.6 g/L and about 6.6 g/L, between about 2.6 g/L and about 6.4 g/L, between about 2.6 g/L and about 6.2 g/L, between about 2.6 g/L and about 6.0 g/L, between about 2.6 g/L and about 5.8 g/L, between about 2.6 g/L and about 5.6 g/L, between about 2.6 g/L and about 5.4 g/L, between about 2.6 g/L and about 5.2 g/L, between about 2.6 g/L and about 5.0 g/L, between about 2.6 g/L and about 4.8 g/L, between about 2.6 g/L and about 4.6 g/L, between about 2.6 g/L and about 4.4 g/L, between about 2.6 g/L and about 4.2 g/L, between about 2.6 g/L and about 4.0 g/L, between about 2.6 g/L and about 3.8 g/L, between about 2.6 g/L and about 3.6 g/L, between about 2.8 g/L and about 16.0 g/L, between about 2.8 g/L and about 15.8 g/L, between about 2.8 g/L and about 15.6 g/L, between about 2.8 g/L and about 15.4 g/L, between about 2.8 g/L and about 15.2 g/L, between about 2.8 g/L and about 15.0 g/L, between about 2.8 g/L and about 14.8 g/L, between about 2.8 g/L and about 14.6 g/L, between about 2.8 g/L and about 14.4 g/L, between about 2.8 g/L and about 14.2 g/L, between about 2.8 g/L and about 14.0 g/L, between about 2.8 g/L and about 13.8 g/L, between about 2.8 g/L and about 13.6 g/L, between about 2.8 g/L and about 13.4 g/L, between about 2.8 g/L and about 13.2 g/L, between about 2.8 g/L and about 13.0 g/L, between about 2.8 g/L and about 12.8 g/L, between about 2.8 g/L and about 12.6 g/L, between about 2.8 g/L and about 12.4 g/L, between about 2.8 g/L and about 12.2 g/L, between about 2.8 g/L and about 12.0 g/L, between about 2.8 g/L and about 11.8 g/L, between about 2.8 g/L and about 11.6 g/L, between about 2.8 g/L and about 11.4 g/L, between about 2.8 g/L and about 11.2 g/L, between about 2.8 g/L and about 11.0 g/L, between about 2.8 g/L and about 10.8 g/L, between about 2.8 g/L and about 10.6 g/L. between about 2.8 g/L and about 10.4 g/L, between about 2.8 g/L and about 10.2 g/L, between about 2.8 g/L and about 10.0 g/L, between about 2.8 g/L and about 9.8 g/L, between about 2.8 g/L and about 9.6 g/L, between about 2.8 g/L and about 9.4 g/L, between about 2.8 g/L and about 9.2 g/L, between about 2.8 g/L and about 9.0 g/L, between about 2.8 g/L and about 8.8 g/L, between about 2.8 g/L and about 8.6 g/L, between about 2.8 g/L and about 8.4 g/L, between about 2.8 g/L and about 8.2 g/L, between about 2.8 g/L and about 8.0 g/L, between about 2.8 g/L and about 7.8 g/L, between about 2.8 g/L and about 7.6 g/L, between about 2.8 g/L and about 7.4 g/L, between about 2.8 g/L and about 7.2 g/L, between about 2.8 g/L and about 7.0 g/L, between about 2.8 g/L and about 6.9 g/L, between about 2.8 g/L and about 6.8 g/L, between about 2.8 g/L and about 6.6 g/L, between about 2.8 g/L and about 6.4 g/L, between about 2.8 g/L and about 6.2 g/L, between about 2.8 g/L and about 6.0 g/L, between about 2.8 g/L and about 5.8 g/L, between about 2.8 g/L and about 5.6 g/L, between about 2.8 g/L and about 5.4 g/L, between about 2.8 g/L and about 5.2 g/L, between about 2.8 g/L and about 5.0 g/L, between about 2.8 g/L and about 4.8 g/L, between about 2.8 g/L and about 4.6 g/L, between about 2.8 g/L and about 4.4 g/L, between about 2.8 g/L and about 4.2 g/L, between about 2.8 g/L and about 4.0 g/L, between about 2.8 g/L and about 3.8 g/L, between about 3.0 g/L and about 16.0 g/L, between about 3.0 g/L and about 15.8 g/L, between about 3.0 g/L and about 15.6 g/L, between about 3.0 g/L and about 15.4 g/L, between about 3.0 g/L and about 15.2 g/L, between about 3.0 g/L and about 15.0 g/L, between about 3.0 g/L and about 14.8 g/L, between about 3.0 g/L and about 14.6 g/L, between about 3.0 g/L and about 14.4 g/L, between about 3.0 g/L and about 14.2 g/L, between about 3.0 g/L and about 14.0 g/L, between about 3.0 g/L and about 13.8 g/L, between about 3.0 g/L and about 13.6 g/L, between about 3.0 g/L and about 13.4 g/L, between about 3.0 g/L and about 13.2 g/L, between about 3.0 g/L and about 13.0 g/L, between about 3.0 g/L and about 12.8 g/L, between about 3.0 g/L and about 12.6 g/L, between about 3.0 g/L and about 12.4 g/L, between about 3.0 g/L and about 12.2 g/L, between about 3.0 g/L and about 12.0 g/L, between about 3.0 g/L and about 11.8 g/L, between about 3.0 g/L and about 11.6 g/L, between about 3.0 g/L and about 11.4 g/L, between about 3.0 g/L and about 11.2 g/L, between about 3.0 g/L and about 11.0 g/L, between about 3.0 g/L and about 10.8 g/L, between about 3.0 g/L and about 10.6 g/L. between about 3.0 g/L and about 10.4 g/L, between about 3.0 g/L and about 10.2 g/L, between about 3.0 g/L and about 10.0 g/L, between about 3.0 g/L and about 9.8 g/L, between about 3.0 g/L and about 9.6 g/L, between about 3.0 g/L and about 9.4 g/L, between about 3.0 g/L and about 9.2 g/L, between about 3.0 g/L and about 9.0 g/L, between about 3.0 g/L and about 8.8 g/L, between about 3.0 g/L and about 8.6 g/L, between about 3.0 g/L and about 8.4 g/L, between about 3.0 g/L and about 8.2 g/L, between about 3.0 g/L and about 8.0 g/L, between about 3.0 g/L and about 7.8 g/L, between about 3.0 g/L and about 7.6 g/L, between about 3.0 g/L and about 7.4 g/L, between about 3.0 g/L and about 7.2 g/L, between about 3.0 g/L and about 7.0 g/L, between about 3.0 g/L and about 6.9 g/L, between about 3.0 g/L and about 6.8 g/L, between about 3.0 g/L and about 6.6 g/L, between about 3.0 g/L and about 6.4 g/L, between about 3.0 g/L and about 6.2 g/L, between about 3.0 g/L and about 6.0 g/L, between about 3.0 g/L and about 5.8 g/L, between about 3.0 g/L and about 5.6 g/L, between about 3.0 g/L and about 5.4 g/L, between about 3.0 g/L and about 5.2 g/L, between about 3.0 g/L and about 5.0 g/L, between about 3.0 g/L and about 4.8 g/L, between about 3.0 g/L and about 4.6 g/L, between about 3.0 g/L and about 4.4 g/L, between about 3.0 g/L and about 4.2 g/L, between about 3.0 g/L and about 4.0 g/L, between about 3.2 g/L and about 16.0 g/L, between about 3.2 g/L and about 15.8 g/L, between about 3.2 g/L and about 15.6 g/L, between about 3.2 g/L and about 15.4 g/L, between about 3.2 g/L and about 15.2 g/L, between about 3.2 g/L and about 15.0 g/L, between about 3.2 g/L and about 14.8 g/L, between about 3.2 g/L and about 14.6 g/L, between about 3.2 g/L and about 14.4 g/L, between about 3.2 g/L and about 14.2 g/L, between about 3.2 g/L and about 14.0 g/L, between about 3.2 g/L and about 13.8 g/L, between about 3.2 g/L and about 13.6 g/L, between about 3.2 g/L and about 13.4 g/L, between about 3.2 g/L and about 13.2 g/L, between about 3.2 g/L and about 13.0 g/L, between about 3.2 g/L and about 12.8 g/L, between about 3.2 g/L and about 12.6 g/L, between about 3.2 g/L and about 12.4 g/L, between about 3.2 g/L and about 12.2 g/L, between about 3.2 g/L and about 12.0 g/L, between about 3.2 g/L and about 11.8 g/L, between about 3.2 g/L and about 11.6 g/L, between about 3.2 g/L and about 11.4 g/L, between about 3.2 g/L and about 11.2 g/L, between about 3.2 g/L and about 11.0 g/L, between about 3.2 g/L and about 10.8 g/L, between about 3.2 g/L and about 10.6 g/L. between about 3.2 g/L and about 10.4 g/L, between about 3.2 g/L and about 10.2 g/L, between about 3.2 g/L and about 10.0 g/L, between about 3.2 g/L and about 9.8 g/L, between about 3.2 g/L and about 9.6 g/L, between about 3.2 g/L and about 9.4 g/L, between about 3.2 g/L and about 9.2 g/L, between about 3.2 g/L and about 9.0 g/L, between about 3.2 g/L and about 8.8 g/L, between about 3.2 g/L and about 8.6 g/L, between about 3.2 g/L and about 8.4 g/L, between about 3.2 g/L and about 8.2 g/L, between about 3.2 g/L and about 8.0 g/L, between about 3.2 g/L and about 7.8 g/L, between about 3.2 g/L and about 7.6 g/L, between about 3.2 g/L and about 7.4 g/L, between about 3.2 g/L and about 7.2 g/L, between about 3.2 g/L and about 7.0 g/L, between about 3.2 g/L and about 6.9 g/L, between about 3.2 g/L and about 6.8 g/L, between about 3.2 g/L and about 6.6 g/L, between about 3.2 g/L and about 6.4 g/L, between about 3.2 g/L and about 6.2 g/L, between about 3.2 g/L and about 6.0 g/L, between about 3.2 g/L and about 5.8 g/L, between about 3.2 g/L and about 5.6 g/L, between about 3.2 g/L and about 5.4 g/L, between about 3.2 g/L and about 5.2 g/L, between about 3.2 g/L and about 5.0 g/L, between about 3.2 g/L and about 4.8 g/L, between about 3.2 g/L and about 4.6 g/L, between about 3.2 g/L and about 4.4 g/L, between about 3.2 g/L and about 4.2 g/L, between about 3.4 g/L and about 16.0 g/L, between about 3.4 g/L and about 15.8 g/L, between about 3.4 g/L and about 15.6 g/L, between about 3.4 g/L and about 15.4 g/L, between about 3.4 g/L and about 15.2 g/L, between about 3.4 g/L and about 15.0 g/L, between about 3.4 g/L and about 14.8 g/L, between about 3.4 g/L and about 14.6 g/L, between about 3.4 g/L and about 14.4 g/L, between about 3.4 g/L and about 14.2 g/L, between about 3.4 g/L and about 14.0 g/L, between about 3.4 g/L and about 13.8 g/L, between about 3.4 g/L and about 13.6 g/L, between about 3.4 g/L and about 13.4 g/L, between about 3.4 g/L and about 13.2 g/L, between about 3.4 g/L and about 13.0 g/L, between about 3.4 g/L and about 12.8 g/L, between about 3.4 g/L and about 12.6 g/L, between about 3.4 g/L and about 12.4 g/L, between about 3.4 g/L and about 12.2 g/L, between about 3.4 g/L and about 12.0 g/L, between about 3.4 g/L and about 11.8 g/L, between about 3.4 g/L and about 11.6 g/L, between about 3.4 g/L and about 11.4 g/L, between about 3.4 g/L and about 11.2 g/L, between about 3.4 g/L and about 11.0 g/L, between about 3.4 g/L and about 10.8 g/L, between about 3.4 g/L and about 10.6 g/L. between about 3.4 g/L and about 10.4 g/L, between about 3.4 g/L and about 10.2 g/L, between about 3.4 g/L and about 10.0 g/L, between about 3.4 g/L and about 9.8 g/L, between about 3.4 g/L and about 9.6 g/L, between about 3.4 g/L and about 9.4 g/L, between about 3.4 g/L and about 9.2 g/L, between about 3.4 g/L and about 9.0 g/L, between about 3.4 g/L and about 8.8 g/L, between about 3.4 g/L and about 8.6 g/L, between about 3.4 g/L and about 8.4 g/L, between about 3.4 g/L and about 8.2 g/L, between about 3.4 g/L and about 8.0 g/L, between about 3.4 g/L and about 7.8 g/L, between about 3.4 g/L and about 7.6 g/L, between about 3.4 g/L and about 7.4 g/L, between about 3.4 g/L and about 7.2 g/L, between about 3.4 g/L and about 7.0 g/L, between about 3.4 g/L and about 6.9 g/L, between about 3.4 g/L and about 6.8 g/L, between about 3.4 g/L and about 6.6 g/L, between about 3.4 g/L and about 6.4 g/L, between about 3.4 g/L and about 6.2 g/L, between about 3.4 g/L and about 6.0 g/L, between about 3.4 g/L and about 5.8 g/L, between about 3.4 g/L and about 5.6 g/L, between about 3.4 g/L and about 5.4 g/L, between about 3.4 g/L and about 5.2 g/L, between about 3.4 g/L and about 5.0 g/L, between about 3.4 g/L and about 4.8 g/L, between about 3.4 g/L and about 4.6 g/L, between about 3.4 g/L and about 4.4 g/L, between about 3.6 g/L and about 16.0 g/L, between about 3.6 g/L and about 15.8 g/L, between about 3.6 g/L and about 15.6 g/L, between about 3.6 g/L and about 15.4 g/L, between about 3.6 g/L and about 15.2 g/L, between about 3.6 g/L and about 15.0 g/L, between about 3.6 g/L and about 14.8 g/L, between about 3.6 g/L and about 14.6 g/L, between about 3.6 g/L and about 14.4 g/L, between about 3.6 g/L and about 14.2 g/L, between about 3.6 g/L and about 14.0 g/L, between about 3.6 g/L and about 13.8 g/L, between about 3.6 g/L and about 13.6 g/L, between about 3.6 g/L and about 13.4 g/L, between about 3.6 g/L and about 13.2 g/L, between about 3.6 g/L and about 13.0 g/L, between about 3.6 g/L and about 12.8 g/L, between about 3.6 g/L and about 12.6 g/L, between about 3.6 g/L and about 12.4 g/L, between about 3.6 g/L and about 12.2 g/L, between about 3.6 g/L and about 12.0 g/L, between about 3.6 g/L and about 11.8 g/L, between about 3.6 g/L and about 11.6 g/L, between about 3.6 g/L and about 11.4 g/L, between about 3.6 g/L and about 11.2 g/L, between about 3.6 g/L and about 11.0 g/L, between about 3.6 g/L and about 10.8 g/L, between about 3.6 g/L and about 10.6 g/L. between about 3.6 g/L and about 10.4 g/L, between about 3.6 g/L and about 10.2 g/L, between about 3.6 g/L and about 10.0 g/L, between about 3.6 g/L and about 9.8 g/L, between about 3.6 g/L and about 9.6 g/L, between about 3.6 g/L and about 9.4 g/L, between about 3.6 g/L and about 9.2 g/L, between about 3.6 g/L and about 9.0 g/L, between about 3.6 g/L and about 8.8 g/L, between about 3.6 g/L and about 8.6 g/L, between about 3.6 g/L and about 8.4 g/L, between about 3.6 g/L and about 8.2 g/L, between about 3.6 g/L and about 8.0 g/L, between about 3.6 g/L and about 7.8 g/L, between about 3.6 g/L and about 7.6 g/L, between about 3.6 g/L and about 7.4 g/L, between about 3.6 g/L and about 7.2 g/L, between about 3.6 g/L and about 7.0 g/L, between about 3.6 g/L and about 6.9 g/L, between about 3.6 g/L and about 6.8 g/L, between about 3.6 g/L and about 6.6 g/L, between about 3.6 g/L and about 6.4 g/L, between about 3.6 g/L and about 6.2 g/L, between about 3.6 g/L and about 6.0 g/L, between about 3.6 g/L and about 5.8 g/L, between about 3.6 g/L and about 5.6 g/L, between about 3.6 g/L and about 5.4 g/L, between about 3.6 g/L and about 5.2 g/L, between about 3.6 g/L and about 5.0 g/L, between about 3.6 g/L and about 4.8 g/L, between about 3.6 g/L and about 4.6 g/L, between about 3.8 g/L and about 16.0 g/L, between about 3.8 g/L and about 15.8 g/L, between about 3.8 g/L and about 15.6 g/L, between about 3.8 g/L and about 15.4 g/L, between about 3.8 g/L and about 15.2 g/L, between about 3.8 g/L and about 15.0 g/L, between about 3.8 g/L and about 14.8 g/L, between about 3.8 g/L and about 14.6 g/L, between about 3.8 g/L and about 14.4 g/L, between about 3.8 g/L and about 14.2 g/L, between about 3.8 g/L and about 14.0 g/L, between about 3.8 g/L and about 13.8 g/L, between about 3.8 g/L and about 13.6 g/L, between about 3.8 g/L and about 13.4 g/L, between about 3.8 g/L and about 13.2 g/L, between about 3.8 g/L and about 13.0 g/L, between about 3.8 g/L and about 12.8 g/L, between about 3.8 g/L and about 12.6 g/L, between about 3.8 g/L and about 12.4 g/L, between about 3.8 g/L and about 12.2 g/L, between about 3.8 g/L and about 12.0 g/L, between about 3.8 g/L and about 11.8 g/L, between about 3.8 g/L and about 11.6 g/L, between about 3.8 g/L and about 11.4 g/L, between about 3.8 g/L and about 11.2 g/L, between about 3.8 g/L and about 11.0 g/L, between about 3.8 g/L and about 10.8 g/L, between about 3.8 g/L and about 10.6 g/L. between about 3.8 g/L and about 10.4 g/L, between about 3.8 g/L and about 10.2 g/L, between about 3.8 g/L and about 10.0 g/L, between about 3.8 g/L and about 9.8 g/L, between about 3.8 g/L and about 9.6 g/L, between about 3.8 g/L and about 9.4 g/L, between about 3.8 g/L and about 9.2 g/L, between about 3.8 g/L and about 9.0 g/L, between about 3.8 g/L and about 8.8 g/L, between about 3.8 g/L and about 8.6 g/L, between about 3.8 g/L and about 8.4 g/L, between about 3.8 g/L and about 8.2 g/L, between about 3.8 g/L and about 8.0 g/L, between about 3.8 g/L and about 7.8 g/L, between about 3.8 g/L and about 7.6 g/L, between about 3.8 g/L and about 7.4 g/L, between about 3.8 g/L and about 7.2 g/L, between about 3.8 g/L and about 7.0 g/L, between about 3.8 g/L and about 6.9 g/L, between about 3.8 g/L and about 6.8 g/L, between about 3.8 g/L and about 6.6 g/L, between about 3.8 g/L and about 6.4 g/L, between about 3.8 g/L and about 6.2 g/L, between about 3.8 g/L and about 6.0 g/L, between about 3.8 g/L and about 5.8 g/L, between about 3.8 g/L and about 5.6 g/L, between about 3.8 g/L and about 5.4 g/L, between about 3.8 g/L and about 5.2 g/L, between about 3.8 g/L and about 5.0 g/L, between about 3.8 g/L and about 4.8 g/L, between about 4.0 g/L and about 16.0 g/L, between about 4.0 g/L and about 15.8 g/L, between about 4.0 g/L and about 15.6 g/L, between about 4.0 g/L and about 15.4 g/L, between about 4.0 g/L and about 15.2 g/L, between about 4.0 g/L and about 15.0 g/L, between about 4.0 g/L and about 14.8 g/L, between about 4.0 g/L and about 14.6 g/L, between about 4.0 g/L and about 14.4 g/L, between about 4.0 g/L and about 14.2 g/L, between about 4.0 g/L and about 14.0 g/L, between about 4.0 g/L and about 13.8 g/L, between about 4.0 g/L and about 13.6 g/L, between about 4.0 g/L and about 13.4 g/L, between about 4.0 g/L and about 13.2 g/L, between about 4.0 g/L and about 13.0 g/L, between about 4.0 g/L and about 12.8 g/L, between about 4.0 g/L and about 12.6 g/L, between about 4.0 g/L and about 12.4 g/L, between about 4.0 g/L and about 12.2 g/L, between about 4.0 g/L and about 12.0 g/L, between about 4.0 g/L and about 11.8 g/L, between about 4.0 g/L and about 11.6 g/L, between about 4.0 g/L and about 11.4 g/L, between about 4.0 g/L and about 11.2 g/L, between about 4.0 g/L and about 11.0 g/L, between about 4.0 g/L and about 10.8 g/L, between about 4.0 g/L and about 10.6 g/L. between about 4.0 g/L and about 10.4 g/L, between about 4.0 g/L and about 10.2 g/L, between about 4.0 g/L and about 10.0 g/L, between about 4.0 g/L and about 9.8 g/L, between about 4.0 g/L and about 9.6 g/L, between about 4.0 g/L and about 9.4 g/L, between about 4.0 g/L and about 9.2 g/L, between about 4.0 g/L and about 9.0 g/L, between about 4.0 g/L and about 8.8 g/L, between about 4.0 g/L and about 8.6 g/L, between about 4.0 g/L and about 8.4 g/L, between about 4.0 g/L and about 8.2 g/L, between about 4.0 g/L and about 8.0 g/L, between about 4.0 g/L and about 7.8 g/L, between about 4.0 g/L and about 7.6 g/L, between about 4.0 g/L and about 7.4 g/L, between about 4.0 g/L and about 7.2 g/L, between about 4.0 g/L and about 7.0 g/L, between about 4.0 g/L and about 6.9 g/L, between about 4.0 g/L and about 6.8 g/L, between about 4.0 g/L and about 6.6 g/L, between about 4.0 g/L and about 6.4 g/L, between about 4.0 g/L and about 6.2 g/L, between about 4.0 g/L and about 6.0 g/L, between about 4.0 g/L and about 5.8 g/L, between about 4.0 g/L and about 5.6 g/L, between about 4.0 g/L and about 5.4 g/L, between about 4.0 g/L and about 5.2 g/L, between about 4.0 g/L and about 5.0 g/L, between about 4.2 g/L and about 16.0 g/L, between about 4.2 g/L and about 15.8 g/L, between about 4.2 g/L and about 15.6 g/L, between about 4.2 g/L and about 15.4 g/L, between about 4.2 g/L and about 15.2 g/L, between about 4.2 g/L and about 15.0 g/L, between about 4.2 g/L and about 14.8 g/L, between about 4.2 g/L and about 14.6 g/L, between about 4.2 g/L and about 14.4 g/L, between about 4.2 g/L and about 14.2 g/L, between about 4.2 g/L and about 14.0 g/L, between about 4.2 g/L and about 13.8 g/L, between about 4.2 g/L and about 13.6 g/L, between about 4.2 g/L and about 13.4 g/L, between about 4.2 g/L and about 13.2 g/L, between about 4.2 g/L and about 13.0 g/L, between about 4.2 g/L and about 12.8 g/L, between about 4.2 g/L and about 12.6 g/L, between about 4.2 g/L and about 12.4 g/L, between about 4.2 g/L and about 12.2 g/L, between about 4.2 g/L and about 12.0 g/L, between about 4.2 g/L and about 11.8 g/L, between about 4.2 g/L and about 11.6 g/L, between about 4.2 g/L and about 11.4 g/L, between about 4.2 g/L and about 11.2 g/L, between about 4.2 g/L and about 11.0 g/L, between about 4.2 g/L and about 10.8 g/L, between about 4.2 g/L and about 10.6 g/L. between about 4.2 g/L and about 10.4 g/L, between about 4.2 g/L and about 10.2 g/L, between about 4.2 g/L and about 10.0 g/L, between about 4.2 g/L and about 9.8 g/L, between about 4.2 g/L and about 9.6 g/L, between about 4.2 g/L and about 9.4 g/L, between about 4.2 g/L and about 9.2 g/L, between about 4.2 g/L and about 9.0 g/L, between about 4.2 g/L and about 8.8 g/L, between about 4.2 g/L and about 8.6 g/L, between about 4.2 g/L and about 8.4 g/L, between about 4.2 g/L and about 8.2 g/L, between about 4.2 g/L and about 8.0 g/L, between about 4.2 g/L and about 7.8 g/L, between about 4.2 g/L and about 7.6 g/L, between about 4.2 g/L and about 7.4 g/L, between about 4.2 g/L and about 7.2 g/L, between about 4.2 g/L and about 7.0 g/L, between about 4.2 g/L and about 6.9 g/L, between about 4.2 g/L and about 6.8 g/L, between about 4.2 g/L and about 6.6 g/L, between about 4.2 g/L and about 6.4 g/L, between about 4.2 g/L and about 6.2 g/L, between about 4.2 g/L and about 6.0 g/L, between about 4.2 g/L and about 5.8 g/L, between about 4.2 g/L and about 5.6 g/L, between about 4.2 g/L and about 5.4 g/L, between about 4.2 g/L and about 5.2 g/L, between about 4.4 g/L and about 16.0 g/L, between about 4.4 g/L and about 15.8 g/L, between about 4.4 g/L and about 15.6 g/L, between about 4.4 g/L and about 15.4 g/L, between about 4.4 g/L and about 15.2 g/L, between about 4.4 g/L and about 15.0 g/L, between about 4.4 g/L and about 14.8 g/L, between about 4.4 g/L and about 14.6 g/L, between about 4.4 g/L and about 14.4 g/L, between about 4.4 g/L and about 14.2 g/L, between about 4.4 g/L and about 14.0 g/L, between about 4.4 g/L and about 13.8 g/L, between about 4.4 g/L and about 13.6 g/L, between about 4.4 g/L and about 13.4 g/L, between about 4.4 g/L and about 13.2 g/L, between about 4.4 g/L and about 13.0 g/L, between about 4.4 g/L and about 12.8 g/L, between about 4.4 g/L and about 12.6 g/L, between about 4.4 g/L and about 12.4 g/L, between about 4.4 g/L and about 12.2 g/L, between about 4.4 g/L and about 12.0 g/L, between about 4.4 g/L and about 11.8 g/L, between about 4.4 g/L and about 11.6 g/L, between about 4.4 g/L and about 11.4 g/L, between about 4.4 g/L and about 11.2 g/L, between about 4.4 g/L and about 11.0 g/L, between about 4.4 g/L and about 10.8 g/L, between about 4.4 g/L and about 10.6 g/L. between about 4.4 g/L and about 10.4 g/L, between about 4.4 g/L and about 10.2 g/L, between about 4.4 g/L and about 10.0 g/L, between about 4.4 g/L and about 9.8 g/L, between about 4.4 g/L and about 9.6 g/L, between about 4.4 g/L and about 9.4 g/L, between about 4.4 g/L and about 9.2 g/L, between about 4.4 g/L and about 9.0 g/L, between about 4.4 g/L and about 8.8 g/L, between about 4.4 g/L and about 8.6 g/L, between about 4.4 g/L and about 8.4 g/L, between about 4.4 g/L and about 8.2 g/L, between about 4.4 g/L and about 8.0 g/L, between about 4.4 g/L and about 7.8 g/L, between about 4.4 g/L and about 7.6 g/L, between about 4.4 g/L and about 7.4 g/L, between about 4.4 g/L and about 7.2 g/L, between about 4.4 g/L and about 7.0 g/L, between about 4.4 g/L and about 6.9 g/L, between about 4.4 g/L and about 6.8 g/L, between about 4.4 g/L and about 6.6 g/L, between about 4.4 g/L and about 6.4 g/L, between about 4.4 g/L and about 6.2 g/L, between about 4.4 g/L and about 6.0 g/L, between about 4.4 g/L and about 5.8 g/L, between about 4.4 g/L and about 5.6 g/L, between about 4.4 g/L and about 5.4 g/L, between about 4.6 g/L and about 16.0 g/L, between about 4.6 g/L and about 15.8 g/L, between about 4.6 g/L and about 15.6 g/L, between about 4.6 g/L and about 15.4 g/L, between about 4.6 g/L and about 15.2 g/L, between about 4.6 g/L and about 15.0 g/L, between about 4.6 g/L and about 14.8 g/L, between about 4.6 g/L and about 14.6 g/L, between about 4.6 g/L and about 14.4 g/L, between about 4.6 g/L and about 14.2 g/L, between about 4.6 g/L and about 14.0 g/L, between about 4.6 g/L and about 13.8 g/L, between about 4.6 g/L and about 13.6 g/L, between about 4.6 g/L and about 13.4 g/L, between about 4.6 g/L and about 13.2 g/L, between about 4.6 g/L and about 13.0 g/L, between about 4.6 g/L and about 12.8 g/L, between about 4.6 g/L and about 12.6 g/L, between about 4.6 g/L and about 12.4 g/L, between about 4.6 g/L and about 12.2 g/L, between about 4.6 g/L and about 12.0 g/L, between about 4.6 g/L and about 11.8 g/L, between about 4.6 g/L and about 11.6 g/L, between about 4.6 g/L and about 11.4 g/L, between about 4.6 g/L and about 11.2 g/L, between about 4.6 g/L and about 11.0 g/L, between about 4.6 g/L and about 10.8 g/L, between about 4.6 g/L and about 10.6 g/L. between about 4.6 g/L and about 10.4 g/L, between about 4.6 g/L and about 10.2 g/L, between about 4.6 g/L and about 10.0 g/L, between about 4.6 g/L and about 9.8 g/L, between about 4.6 g/L and about 9.6 g/L, between about 4.6 g/L and about 9.4 g/L, between about 4.6 g/L and about 9.2 g/L, between about 4.6 g/L and about 9.0 g/L, between about 4.6 g/L and about 8.8 g/L, between about 4.6 g/L and about 8.6 g/L, between about 4.6 g/L and about 8.4 g/L, between about 4.6 g/L and about 8.2 g/L, between about 4.6 g/L and about 8.0 g/L, between about 4.6 g/L and about 7.8 g/L, between about 4.6 g/L and about 7.6 g/L, between about 4.6 g/L and about 7.4 g/L, between about 4.6 g/L and about 7.2 g/L, between about 4.6 g/L and about 7.0 g/L, between about 4.6 g/L and about 6.9 g/L, between about 4.6 g/L and about 6.8 g/L, between about 4.6 g/L and about 6.6 g/L, between about 4.6 g/L and about 6.4 g/L, between about 4.6 g/L and about 6.2 g/L, between about 4.6 g/L and about 6.0 g/L, between about 4.6 g/L and about 5.8 g/L, between about 4.6 g/L and about 5.6 g/L, between about 4.8 g/L and about 16.0 g/L, between about 4.8 g/L and about 15.8 g/L, between about 4.8 g/L and about 15.6 g/L, between about 4.8 g/L and about 15.4 g/L, between about 4.8 g/L and about 15.2 g/L, between about 4.8 g/L and about 15.0 g/L, between about 4.8 g/L and about 14.8 g/L, between about 4.8 g/L and about 14.6 g/L, between about 4.8 g/L and about 14.4 g/L, between about 4.8 g/L and about 14.2 g/L, between about 4.8 g/L and about 14.0 g/L, between about 4.8 g/L and about 13.8 g/L, between about 4.8 g/L and about 13.6 g/L, between about 4.8 g/L and about 13.4 g/L, between about 4.8 g/L and about 13.2 g/L, between about 4.8 g/L and about 13.0 g/L, between about 4.8 g/L and about 12.8 g/L, between about 4.8 g/L and about 12.6 g/L, between about 4.8 g/L and about 12.4 g/L, between about 4.8 g/L and about 12.2 g/L, between about 4.8 g/L and about 12.0 g/L, between about 4.8 g/L and about 11.8 g/L, between about 4.8 g/L and about 11.6 g/L, between about 4.8 g/L and about 11.4 g/L, between about 4.8 g/L and about 11.2 g/L, between about 4.8 g/L and about 11.0 g/L, between about 4.8 g/L and about 10.8 g/L, between about 4.8 g/L and about 10.6 g/L. between about 4.8 g/L and about 10.4 g/L, between about 4.8 g/L and about 10.2 g/L, between about 4.8 g/L and about 10.0 g/L, between about 4.8 g/L and about 9.8 g/L, between about 4.8 g/L and about 9.6 g/L, between about 4.8 g/L and about 9.4 g/L, between about 4.8 g/L and about 9.2 g/L, between about 4.8 g/L and about 9.0 g/L, between about 4.8 g/L and about 8.8 g/L, between about 4.8 g/L and about 8.6 g/L, between about 4.8 g/L and about 8.4 g/L, between about 4.8 g/L and about 8.2 g/L, between about 4.8 g/L and about 8.0 g/L, between about 4.8 g/L and about 7.8 g/L, between about 4.8 g/L and about 7.6 g/L, between about 4.8 g/L and about 7.4 g/L, between about 4.8 g/L and about 7.2 g/L, between about 4.8 g/L and about 7.0 g/L, between about 4.8 g/L and about 6.9 g/L, between about 4.8 g/L and about 6.8 g/L, between about 4.8 g/L and about 6.6 g/L, between about 4.8 g/L and about 6.4 g/L, between about 4.8 g/L and about 6.2 g/L, between about 4.8 g/L and about 6.0 g/L, between about 4.8 g/L and about 5.8 g/L, between about 5.0 g/L and about 16.0 g/L, between about 5.0 g/L and about 15.8 g/L, between about 5.0 g/L and about 15.6 g/L, between about 5.0 g/L and about 15.4 g/L, between about 5.0 g/L and about 15.2 g/L, between about 5.0 g/L and about 15.0 g/L, between about 5.0 g/L and about 14.8 g/L, between about 5.0 g/L and about 14.6 g/L, between about 5.0 g/L and about 14.4 g/L, between about 5.0 g/L and about 14.2 g/L, between about 5.0 g/L and about 14.0 g/L, between about 5.0 g/L and about 13.8 g/L, between about 5.0 g/L and about 13.6 g/L, between about 5.0 g/L and about 13.4 g/L, between about 5.0 g/L and about 13.2 g/L, between about 5.0 g/L and about 13.0 g/L, between about 5.0 g/L and about 12.8 g/L, between about 5.0 g/L and about 12.6 g/L, between about 5.0 g/L and about 12.4 g/L, between about 5.0 g/L and about 12.2 g/L, between about 5.0 g/L and about 12.0 g/L, between about 5.0 g/L and about 11.8 g/L, between about 5.0 g/L and about 11.6 g/L, between about 5.0 g/L and about 11.4 g/L, between about 5.0 g/L and about 11.2 g/L, between about 5.0 g/L and about 11.0 g/L, between about 5.0 g/L and about 10.8 g/L, between about 5.0 g/L and about 10.6 g/L. between about 5.0 g/L and about 10.4 g/L, between about 5.0 g/L and about 10.2 g/L, between about 5.0 g/L and about 10.0 g/L, between about 5.0 g/L and about 9.8 g/L, between about 5.0 g/L and about 9.6 g/L, between about 5.0 g/L and about 9.4 g/L, between about 5.0 g/L and about 9.2 g/L, between about 5.0 g/L and about 9.0 g/L, between about 5.0 g/L and about 8.8 g/L, between about 5.0 g/L and about 8.6 g/L, between about 5.0 g/L and about 8.4 g/L, between about 5.0 g/L and about 8.2 g/L, between about 5.0 g/L and about 8.0 g/L, between about 5.0 g/L and about 7.8 g/L, between about 5.0 g/L and about 7.6 g/L, between about 5.0 g/L and about 7.4 g/L, between about 5.0 g/L and about 7.2 g/L, between about 5.0 g/L and about 7.0 g/L, between about 5.0 g/L and about 6.9 g/L, between about 5.0 g/L and about 6.8 g/L, between about 5.0 g/L and about 6.6 g/L, between about 5.0 g/L and about 6.4 g/L, between about 5.0 g/L and about 6.2 g/L, between about 5.0 g/L and about 6.0 g/L, between about 5.1 g/L and about 16.0 g/L, between about 5.1 g/L and about 15.8 g/L, between about 5.1 g/L and about 15.6 g/L, between about 5.1 g/L and about 15.4 g/L, between about 5.1 g/L and about 15.2 g/L, between about 5.1 g/L and about 15.0 g/L, between about 5.1 g/L and about 14.8 g/L, between about 5.1 g/L and about 14.6 g/L, between about 5.1 g/L and about 14.4 g/L, between about 5.1 g/L and about 14.2 g/L, between about 5.1 g/L and about 14.0 g/L, between about 5.1 g/L and about 13.8 g/L, between about 5.1 g/L and about 13.6 g/L, between about 5.1 g/L and about 13.4 g/L, between about 5.1 g/L and about 13.2 g/L, between about 5.1 g/L and about 13.0 g/L, between about 5.1 g/L and about 12.8 g/L, between about 5.1 g/L and about 12.6 g/L, between about 5.1 g/L and about 12.4 g/L, between about 5.1 g/L and about 12.2 g/L, between about 5.1 g/L and about 12.0 g/L, between about 5.1 g/L and about 11.8 g/L, between about 5.1 g/L and about 11.6 g/L, between about 5.1 g/L and about 11.4 g/L, between about 5.1 g/L and about 11.2 g/L, between about 5.1 g/L and about 11.0 g/L, between about 5.1 g/L and about 10.8 g/L, between about 5.1 g/L and about 10.6 g/L. between about 5.1 g/L and about 10.4 g/L, between about 5.1 g/L and about 10.2 g/L, between about 5.1 g/L and about 10.0 g/L, between about 5.1 g/L and about 9.8 g/L, between about 5.1 g/L and about 9.6 g/L, between about 5.1 g/L and about 9.4 g/L, between about 5.1 g/L and about 9.2 g/L, between about 5.1 g/L and about 9.0 g/L, between about 5.1 g/L and about 8.8 g/L, between about 5.1 g/L and about 8.6 g/L, between about 5.1 g/L and about 8.4 g/L, between about 5.1 g/L and about 8.2 g/L, between about 5.1 g/L and about 8.0 g/L, between about 5.1 g/L and about 7.8 g/L, between about 5.1 g/L and about 7.6 g/L, between about 5.1 g/L and about 7.4 g/L, between about 5.1 g/L and about 7.2 g/L, between about 5.1 g/L and about 7.0 g/L, between about 5.1 g/L and about 6.9 g/L, between about 5.1 g/L and about 6.8 g/L, between about 5.1 g/L and about 6.6 g/L, between about 5.1 g/L and about 6.4 g/L, between about 5.1 g/L and about 6.2 g/L, between about 5.1 g/L and about 6.1 g/L, between about 5.2 g/L and about 16.0 g/L, between about 5.2 g/L and about 15.8 g/L, between about 5.2 g/L and about 15.6 g/L, between about 5.2 g/L and about 15.4 g/L, between about 5.2 g/L and about 15.2 g/L, between about 5.2 g/L and about 15.0 g/L, between about 5.2 g/L and about 14.8 g/L, between about 5.2 g/L and about 14.6 g/L, between about 5.2 g/L and about 14.4 g/L, between about 5.2 g/L and about 14.2 g/L, between about 5.2 g/L and about 14.0 g/L, between about 5.2 g/L and about 13.8 g/L, between about 5.2 g/L and about 13.6 g/L, between about 5.2 g/L and about 13.4 g/L, between about 5.2 g/L and about 13.2 g/L, between about 5.2 g/L and about 13.0 g/L, between about 5.2 g/L and about 12.8 g/L, between about 5.2 g/L and about 12.6 g/L, between about 5.2 g/L and about 12.4 g/L, between about 5.2 g/L and about 12.2 g/L, between about 5.2 g/L and about 12.0 g/L, between about 5.2 g/L and about 11.8 g/L, between about 5.2 g/L and about 11.6 g/L, between about 5.2 g/L and about 11.4 g/L, between about 5.2 g/L and about 11.2 g/L, between about 5.2 g/L and about 11.0 g/L, between about 5.2 g/L and about 10.8 g/L, between about 5.2 g/L and about 10.6 g/L. between about 5.2 g/L and about 10.4 g/L, between about 5.2 g/L and about 10.2 g/L, between about 5.2 g/L and about 10.0 g/L, between about 5.2 g/L and about 9.8 g/L, between about 5.2 g/L and about 9.6 g/L, between about 5.2 g/L and about 9.4 g/L, between about 5.2 g/L and about 9.2 g/L, between about 5.2 g/L and about 9.0 g/L, between about 5.2 g/L and about 8.8 g/L, between about 5.2 g/L and about 8.6 g/L, between about 5.2 g/L and about 8.4 g/L, between about 5.2 g/L and about 8.2 g/L, between about 5.2 g/L and about 8.0 g/L, between about 5.2 g/L and about 7.8 g/L, between about 5.2 g/L and about 7.6 g/L, between about 5.2 g/L and about 7.4 g/L, between about 5.2 g/L and about 7.2 g/L, between about 5.2 g/L and about 7.0 g/L, between about 5.2 g/L and about 6.9 g/L, between about 5.2 g/L and about 6.8 g/L, between about 5.2 g/L and about 6.6 g/L, between about 5.2 g/L and about 6.4 g/L, between about 5.2 g/L and about 6.2 g/L, between about 5.4 g/L and about 16.0 g/L, between about 5.4 g/L and about 15.8 g/L, between about 5.4 g/L and about 15.6 g/L, between about 5.4 g/L and about 15.4 g/L, between about 5.4 g/L and about 15.2 g/L, between about 5.4 g/L and about 15.0 g/L, between about 5.4 g/L and about 14.8 g/L, between about 5.4 g/L and about 14.6 g/L, between about 5.4 g/L and about 14.4 g/L, between about 5.4 g/L and about 14.2 g/L, between about 5.4 g/L and about 14.0 g/L, between about 5.4 g/L and about 13.8 g/L, between about 5.4 g/L and about 13.6 g/L, between about 5.4 g/L and about 13.4 g/L, between about 5.4 g/L and about 13.2 g/L, between about 5.4 g/L and about 13.0 g/L, between about 5.4 g/L and about 12.8 g/L, between about 5.4 g/L and about 12.6 g/L, between about 5.4 g/L and about 12.4 g/L, between about 5.4 g/L and about 12.2 g/L, between about 5.4 g/L and about 12.0 g/L, between about 5.4 g/L and about 11.8 g/L, between about 5.4 g/L and about 11.6 g/L, between about 5.4 g/L and about 11.4 g/L, between about 5.4 g/L and about 11.2 g/L, between about 5.4 g/L and about 11.0 g/L, between about 5.4 g/L and about 10.8 g/L, between about 5.4 g/L and about 10.6 g/L. between about 5.4 g/L and about 10.4 g/L, between about 5.4 g/L and about 10.2 g/L, between about 5.4 g/L and about 10.0 g/L, between about 5.4 g/L and about 9.8 g/L, between about 5.4 g/L and about 9.6 g/L, between about 5.4 g/L and about 9.4 g/L, between about 5.4 g/L and about 9.2 g/L, between about 5.4 g/L and about 9.0 g/L, between about 5.4 g/L and about 8.8 g/L, between about 5.4 g/L and about 8.6 g/L, between about 5.4 g/L and about 8.4 g/L, between about 5.4 g/L and about 8.2 g/L, between about 5.4 g/L and about 8.0 g/L, between about 5.4 g/L and about 7.8 g/L, between about 5.4 g/L and about 7.6 g/L, between about 5.4 g/L and about 7.4 g/L, between about 5.4 g/L and about 7.2 g/L, between about 5.4 g/L and about 7.0 g/L, between about 5.4 g/L and about 6.9 g/L, between about 5.4 g/L and about 6.8 g/L, between about 5.4 g/L and about 6.6 g/L, between about 5.4 g/L and about 6.4 g/L, between about 5.6 g/L and about 16.0 g/L, between about 5.6 g/L and about 15.8 g/L, between about 5.6 g/L and about 15.6 g/L, between about 5.6 g/L and about 15.4 g/L, between about 5.6 g/L and about 15.2 g/L, between about 5.6 g/L and about 15.0 g/L, between about 5.6 g/L and about 14.8 g/L, between about 5.6 g/L and about 14.6 g/L, between about 5.6 g/L and about 14.4 g/L, between about 5.6 g/L and about 14.2 g/L, between about 5.6 g/L and about 14.0 g/L, between about 5.6 g/L and about 13.8 g/L, between about 5.6 g/L and about 13.6 g/L, between about 5.6 g/L and about 13.4 g/L, between about 5.6 g/L and about 13.2 g/L, between about 5.6 g/L and about 13.0 g/L, between about 5.6 g/L and about 12.8 g/L, between about 5.6 g/L and about 12.6 g/L, between about 5.6 g/L and about 12.4 g/L, between about 5.6 g/L and about 12.2 g/L, between about 5.6 g/L and about 12.0 g/L, between about 5.6 g/L and about 11.8 g/L, between about 5.6 g/L and about 11.6 g/L, between about 5.6 g/L and about 11.4 g/L, between about 5.6 g/L and about 11.2 g/L, between about 5.6 g/L and about 11.0 g/L, between about 5.6 g/L and about 10.8 g/L, between about 5.6 g/L and about 10.6 g/L. between about 5.6 g/L and about 10.4 g/L, between about 5.6 g/L and about 10.2 g/L, between about 5.6 g/L and about 10.0 g/L, between about 5.6 g/L and about 9.8 g/L, between about 5.6 g/L and about 9.6 g/L, between about 5.6 g/L and about 9.4 g/L, between about 5.6 g/L and about 9.2 g/L, between about 5.6 g/L and about 9.0 g/L, between about 5.6 g/L and about 8.8 g/L, between about 5.6 g/L and about 8.6 g/L, between about 5.6 g/L and about 8.4 g/L, between about 5.6 g/L and about 8.2 g/L, between about 5.6 g/L and about 8.0 g/L, between about 5.6 g/L and about 7.8 g/L, between about 5.6 g/L and about 7.6 g/L, between about 5.6 g/L and about 7.4 g/L, between about 5.6 g/L and about 7.2 g/L, between about 5.6 g/L and about 7.0 g/L, between about 5.6 g/L and about 6.9 g/L, between about 5.6 g/L and about 6.8 g/L, between about 5.6 g/L and about 6.6 g/L, between about 5.8 g/L and about 16.0 g/L, between about 5.8 g/L and about 15.8 g/L, between about 5.8 g/L and about 15.6 g/L, between about 5.8 g/L and about 15.4 g/L, between about 5.8 g/L and about 15.2 g/L, between about 5.8 g/L and about 15.0 g/L, between about 5.8 g/L and about 14.8 g/L, between about 5.8 g/L and about 14.6 g/L, between about 5.8 g/L and about 14.4 g/L, between about 5.8 g/L and about 14.2 g/L, between about 5.8 g/L and about 14.0 g/L, between about 5.8 g/L and about 13.8 g/L, between about 5.8 g/L and about 13.6 g/L, between about 5.8 g/L and about 13.4 g/L, between about 5.8 g/L and about 13.2 g/L, between about 5.8 g/L and about 13.0 g/L, between about 5.8 g/L and about 12.8 g/L, between about 5.8 g/L and about 12.6 g/L, between about 5.8 g/L and about 12.4 g/L, between about 5.8 g/L and about 12.2 g/L, between about 5.8 g/L and about 12.0 g/L, between about 5.8 g/L and about 11.8 g/L, between about 5.8 g/L and about 11.6 g/L, between about 5.8 g/L and about 11.4 g/L, between about 5.8 g/L and about 11.2 g/L, between about 5.8 g/L and about 11.0 g/L, between about 5.8 g/L and about 10.8 g/L, between about 5.8 g/L and about 10.6 g/L. between about 5.8 g/L and about 10.4 g/L, between about 5.8 g/L and about 10.2 g/L, between about 5.8 g/L and about 10.0 g/L, between about 5.8 g/L and about 9.8 g/L, between about 5.8 g/L and about 9.6 g/L, between about 5.8 g/L and about 9.4 g/L, between about 5.8 g/L and about 9.2 g/L, between about 5.8 g/L and about 9.0 g/L, between about 5.8 g/L and about 8.8 g/L, between about 5.8 g/L and about 8.6 g/L, between about 5.8 g/L and about 8.4 g/L, between about 5.8 g/L and about 8.2 g/L, between about 5.8 g/L and about 8.0 g/L, between about 5.8 g/L and about 7.8 g/L, between about 5.8 g/L and about 7.6 g/L, between about 5.8 g/L and about 7.4 g/L, between about 5.8 g/L and about 7.2 g/L, between about 5.8 g/L and about 7.0 g/L, between about 5.8 g/L and about 6.9 g/L, between about 5.8 g/L and about 6.8 g/L, between about 6.0 g/L and about 16.0 g/L, between about 6.0 g/L and about 15.8 g/L, between about 6.0 g/L and about 15.6 g/L, between about 6.0 g/L and about 15.4 g/L, between about 6.0 g/L and about 15.2 g/L, between about 6.0 g/L and about 15.0 g/L, between about 6.0 g/L and about 14.8 g/L, between about 6.0 g/L and about 14.6 g/L, between about 6.0 g/L and about 14.4 g/L, between about 6.0 g/L and about 14.2 g/L, between about 6.0 g/L and about 14.0 g/L, between about 6.0 g/L and about 13.8 g/L, between about 6.0 g/L and about 13.6 g/L, between about 6.0 g/L and about 13.4 g/L, between about 6.0 g/L and about 13.2 g/L, between about 6.0 g/L and about 13.0 g/L, between about 6.0 g/L and about 12.8 g/L, between about 6.0 g/L and about 12.6 g/L, between about 6.0 g/L and about 12.4 g/L, between about 6.0 g/L and about 12.2 g/L, between about 6.0 g/L and about 12.0 g/L, between about 6.0 g/L and about 11.8 g/L, between about 6.0 g/L and about 11.6 g/L, between about 6.0 g/L and about 11.4 g/L, between about 6.0 g/L and about 11.2 g/L, between about 6.0 g/L and about 11.0 g/L, between about 6.0 g/L and about 10.8 g/L, between about 6.0 g/L and about 10.6 g/L. between about 6.0 g/L and about 10.4 g/L, between about 6.0 g/L and about 10.2 g/L, between about 6.0 g/L and about 10.0 g/L, between about 6.0 g/L and about 9.8 g/L, between about 6.0 g/L and about 9.6 g/L, between about 6.0 g/L and about 9.4 g/L, between about 6.0 g/L and about 9.2 g/L, between about 6.0 g/L and about 9.0 g/L, between about 6.0 g/L and about 8.8 g/L, between about 6.0 g/L and about 8.6 g/L, between about 6.0 g/L and about 8.4 g/L, between about 6.0 g/L and about 8.2 g/L, between about 6.0 g/L and about 8.0 g/L, between about 6.0 g/L and about 7.8 g/L, between about 6.0 g/L and about 7.6 g/L, between about 6.0 g/L and about 7.4 g/L, between about 6.0 g/L and about 7.2 g/L, between about 6.0 g/L and about 7.0 g/L, between about 6.2 g/L and about 16.0 g/L, between about 6.2 g/L and about 15.8 g/L, between about 6.2 g/L and about 15.6 g/L, between about 6.2 g/L and about 15.4 g/L, between about 6.2 g/L and about 15.2 g/L, between about 6.2 g/L and about 15.0 g/L, between about 6.2 g/L and about 14.8 g/L, between about 6.2 g/L and about 14.6 g/L, between about 6.2 g/L and about 14.4 g/L, between about 6.2 g/L and about 14.2 g/L, between about 6.2 g/L and about 14.0 g/L, between about 6.2 g/L and about 13.8 g/L, between about 6.2 g/L and about 13.6 g/L, between about 6.2 g/L and about 13.4 g/L, between about 6.2 g/L and about 13.2 g/L, between about 6.2 g/L and about 13.0 g/L, between about 6.2 g/L and about 12.8 g/L, between about 6.2 g/L and about 12.6 g/L, between about 6.2 g/L and about 12.4 g/L, between about 6.2 g/L and about 12.2 g/L, between about 6.2 g/L and about 12.0 g/L, between about 6.2 g/L and about 11.8 g/L, between about 6.2 g/L and about 11.6 g/L, between about 6.2 g/L and about 11.4 g/L, between about 6.2 g/L and about 11.2 g/L, between about 6.2 g/L and about 11.0 g/L, between about 6.2 g/L and about 10.8 g/L, between about 6.2 g/L and about 10.6 g/L. between about 6.2 g/L and about 10.4 g/L, between about 6.2 g/L and about 10.2 g/L, between about 6.2 g/L and about 10.0 g/L, between about 6.2 g/L and about 9.8 g/L, between about 6.2 g/L and about 9.6 g/L, between about 6.2 g/L and about 9.4 g/L, between about 6.2 g/L and about 9.2 g/L, between about 6.2 g/L and about 9.0 g/L, between about 6.2 g/L and about 8.8 g/L, between about 6.2 g/L and about 8.6 g/L, between about 6.2 g/L and about 8.4 g/L, between about 6.2 g/L and about 8.2 g/L, between about 6.2 g/L and about 8.0 g/L, between about 6.2 g/L and about 7.8 g/L, between about 6.2 g/L and about 7.6 g/L, between about 6.2 g/L and about 7.4 g/L, between about 6.2 g/L and about 7.2 g/L, between about 6.4 g/L and about 16.0 g/L, between about 6.4 g/L and about 15.8 g/L, between about 6.4 g/L and about 15.6 g/L, between about 6.4 g/L and about 15.4 g/L, between about 6.4 g/L and about 15.2 g/L, between about 6.4 g/L and about 15.0 g/L, between about 6.4 g/L and about 14.8 g/L, between about 6.4 g/L and about 14.6 g/L, between about 6.4 g/L and about 14.4 g/L, between about 6.4 g/L and about 14.2 g/L, between about 6.4 g/L and about 14.0 g/L, between about 6.4 g/L and about 13.8 g/L, between about 6.4 g/L and about 13.6 g/L, between about 6.4 g/L and about 13.4 g/L, between about 6.4 g/L and about 13.2 g/L, between about 6.4 g/L and about 13.0 g/L, between about 6.4 g/L and about 12.8 g/L, between about 6.4 g/L and about 12.6 g/L, between about 6.4 g/L and about 12.4 g/L, between about 6.4 g/L and about 12.2 g/L, between about 6.4 g/L and about 12.0 g/L, between about 6.4 g/L and about 11.8 g/L, between about 6.4 g/L and about 11.6 g/L, between about 6.4 g/L and about 11.4 g/L, between about 6.4 g/L and about 11.2 g/L, between about 6.4 g/L and about 11.0 g/L, between about 6.4 g/L and about 10.8 g/L, between about 6.4 g/L and about 10.6 g/L. between about 6.4 g/L and about 10.4 g/L, between about 6.4 g/L and about 10.2 g/L, between about 6.4 g/L and about 10.0 g/L, between about 6.4 g/L and about 9.8 g/L, between about 6.4 g/L and about 9.6 g/L, between about 6.4 g/L and about 9.4 g/L, between about 6.4 g/L and about 9.2 g/L, between about 6.4 g/L and about 9.0 g/L, between about 6.4 g/L and about 8.8 g/L, between about 6.4 g/L and about 8.6 g/L, between about 6.4 g/L and about 8.4 g/L, between about 6.4 g/L and about 8.2 g/L, between about 6.4 g/L and about 8.0 g/L, between about 6.4 g/L and about 7.8 g/L, between about 6.4 g/L and about 7.6 g/L, between about 6.4 g/L and about 7.4 g/L, between about 6.6 g/L and about 16.0 g/L, between about 6.6 g/L and about 15.8 g/L, between about 6.6 g/L and about 15.6 g/L, between about 6.6 g/L and about 15.4 g/L, between about 6.6 g/L and about 15.2 g/L, between about 6.6 g/L and about 15.0 g/L, between about 6.6 g/L and about 14.8 g/L, between about 6.6 g/L and about 14.6 g/L, between about 6.6 g/L and about 14.4 g/L, between about 6.6 g/L and about 14.2 g/L, between about 6.6 g/L and about 14.0 g/L, between about 6.6 g/L and about 13.8 g/L, between about 6.6 g/L and about 13.6 g/L, between about 6.6 g/L and about 13.4 g/L, between about 6.6 g/L and about 13.2 g/L, between about 6.6 g/L and about 13.0 g/L, between about 6.6 g/L and about 12.8 g/L, between about 6.6 g/L and about 12.6 g/L, between about 6.6 g/L and about 12.4 g/L, between about 6.6 g/L and about 12.2 g/L, between about 6.6 g/L and about 12.0 g/L, between about 6.6 g/L and about 11.8 g/L, between about 6.6 g/L and about 11.6 g/L, between about 6.6 g/L and about 11.4 g/L, between about 6.6 g/L and about 11.2 g/L, between about 6.6 g/L and about 11.0 g/L, between about 6.6 g/L and about 10.8 g/L, between about 6.6 g/L and about 10.6 g/L. between about 6.6 g/L and about 10.4 g/L, between about 6.6 g/L and about 10.2 g/L, between about 6.6 g/L and about 10.0 g/L, between about 6.6 g/L and about 9.8 g/L, between about 6.6 g/L and about 9.6 g/L, between about 6.6 g/L and about 9.4 g/L, between about 6.6 g/L and about 9.2 g/L, between about 6.6 g/L and about 9.0 g/L, between about 6.6 g/L and about 8.8 g/L, between about 6.6 g/L and about 8.6 g/L, between about 6.6 g/L and about 8.4 g/L, between about 6.6 g/L and about 8.2 g/L, between about 6.6 g/L and about 8.0 g/L, between about 6.6 g/L and about 7.8 g/L, between about 6.6 g/L and about 7.6 g/L, between about 6.8 g/L and about 16.0 g/L, between about 6.8 g/L and about 15.8 g/L, between about 6.8 g/L and about 15.6 g/L, between about 6.8 g/L and about 15.4 g/L, between about 6.8 g/L and about 15.2 g/L, between about 6.8 g/L and about 15.0 g/L, between about 6.8 g/L and about 14.8 g/L, between about 6.8 g/L and about 14.6 g/L, between about 6.8 g/L and about 14.4 g/L, between about 6.8 g/L and about 14.2 g/L, between about 6.8 g/L and about 14.0 g/L, between about 6.8 g/L and about 13.8 g/L, between about 6.8 g/L and about 13.6 g/L, between about 6.8 g/L and about 13.4 g/L, between about 6.8 g/L and about 13.2 g/L, between about 6.8 g/L and about 13.0 g/L, between about 6.8 g/L and about 12.8 g/L, between about 6.8 g/L and about 12.6 g/L, between about 6.8 g/L and about 12.4 g/L, between about 6.8 g/L and about 12.2 g/L, between about 6.8 g/L and about 12.0 g/L, between about 6.8 g/L and about 11.8 g/L, between about 6.8 g/L and about 11.6 g/L, between about 6.8 g/L and about 11.4 g/L, between about 6.8 g/L and about 11.2 g/L, between about 6.8 g/L and about 11.0 g/L, between about 6.8 g/L and about 10.8 g/L, between about 6.8 g/L and about 10.6 g/L. between about 6.8 g/L and about 10.4 g/L, between about 6.8 g/L and about 10.2 g/L, between about 6.8 g/L and about 10.0 g/L, between about 6.8 g/L and about 9.8 g/L, between about 6.8 g/L and about 9.6 g/L, between about 6.8 g/L and about 9.4 g/L, between about 6.8 g/L and about 9.2 g/L, between about 6.8 g/L and about 9.0 g/L, between about 6.8 g/L and about 8.8 g/L, between about 6.8 g/L and about 8.6 g/L, between about 6.8 g/L and about 8.4 g/L, between about 6.8 g/L and about 8.2 g/L, between about 6.8 g/L and about 8.0 g/L, between about 6.8 g/L and about 7.8 g/L, between about 7.0 g/L and about 16.0 g/L, between about 7.0 g/L and about 15.8 g/L, between about 7.0 g/L and about 15.6 g/L, between about 7.0 g/L and about 15.4 g/L, between about 7.0 g/L and about 15.2 g/L, between about 7.0 g/L and about 15.0 g/L, between about 7.0 g/L and about 14.8 g/L, between about 7.0 g/L and about 14.6 g/L, between about 7.0 g/L and about 14.4 g/L, between about 7.0 g/L and about 14.2 g/L, between about 7.0 g/L and about 14.0 g/L, between about 7.0 g/L and about 13.8 g/L, between about 7.0 g/L and about 13.6 g/L, between about 7.0 g/L and about 13.4 g/L, between about 7.0 g/L and about 13.2 g/L, between about 7.0 g/L and about 13.0 g/L, between about 7.0 g/L and about 12.8 g/L, between about 7.0 g/L and about 12.6 g/L, between about 7.0 g/L and about 12.4 g/L, between about 7.0 g/L and about 12.2 g/L, between about 7.0 g/L and about 12.0 g/L, between about 7.0 g/L and about 11.8 g/L, between about 7.0 g/L and about 11.6 g/L, between about 7.0 g/L and about 11.4 g/L, between about 7.0 g/L and about 11.2 g/L, between about 7.0 g/L and about 11.0 g/L, between about 7.0 g/L and about 10.8 g/L, between about 7.0 g/L and about 10.6 g/L. between about 7.0 g/L and about 10.4 g/L, between about 7.0 g/L and about 10.2 g/L, between about 7.0 g/L and about 10.0 g/L, between about 7.0 g/L and about 9.8 g/L, between about 7.0 g/L and about 9.6 g/L, between about 7.0 g/L and about 9.4 g/L, between about 7.0 g/L and about 9.2 g/L, between about 7.0 g/L and about 9.0 g/L, between about 7.0 g/L and about 8.8 g/L, between about 7.0 g/L and about 8.6 g/L, between about 7.0 g/L and about 8.4 g/L, between about 7.0 g/L and about 8.2 g/L, between about 7.0 g/L and about 8.0 g/L, between about 7.2 g/L and about 16.0 g/L, between about 7.2 g/L and about 15.8 g/L, between about 7.2 g/L and about 15.6 g/L, between about 7.2 g/L and about 15.4 g/L, between about 7.2 g/L and about 15.2 g/L, between about 7.2 g/L and about 15.0 g/L, between about 7.2 g/L and about 14.8 g/L, between about 7.2 g/L and about 14.6 g/L, between about 7.2 g/L and about 14.4 g/L, between about 7.2 g/L and about 14.2 g/L, between about 7.2 g/L and about 14.0 g/L, between about 7.2 g/L and about 13.8 g/L, between about 7.2 g/L and about 13.6 g/L, between about 7.2 g/L and about 13.4 g/L, between about 7.2 g/L and about 13.2 g/L, between about 7.2 g/L and about 13.0 g/L, between about 7.2 g/L and about 12.8 g/L, between about 7.2 g/L and about 12.6 g/L, between about 7.2 g/L and about 12.4 g/L, between about 7.2 g/L and about 12.2 g/L, between about 7.2 g/L and about 12.0 g/L, between about 7.2 g/L and about 11.8 g/L, between about 7.2 g/L and about 11.6 g/L, between about 7.2 g/L and about 11.4 g/L, between about 7.2 g/L and about 11.2 g/L, between about 7.2 g/L and about 11.0 g/L, between about 7.2 g/L and about 10.8 g/L, between about 7.2 g/L and about 10.6 g/L. between about 7.2 g/L and about 10.4 g/L, between about 7.2 g/L and about 10.2 g/L, between about 7.2 g/L and about 10.0 g/L, between about 7.2 g/L and about 9.8 g/L, between about 7.2 g/L and about 9.6 g/L, between about 7.2 g/L and about 9.4 g/L, between about 7.2 g/L and about 9.2 g/L, between about 7.2 g/L and about 9.0 g/L, between about 7.2 g/L and about 8.8 g/L, between about 7.2 g/L and about 8.6 g/L, between about 7.2 g/L and about 8.4 g/L, between about 7.2 g/L and about 8.2 g/L, between about 7.4 g/L and about 16.0 g/L, between about 7.4 g/L and about 15.8 g/L, between about 7.4 g/L and about 15.6 g/L, between about 7.4 g/L and about 15.4 g/L, between about 7.4 g/L and about 15.2 g/L, between about 7.4 g/L and about 15.0 g/L, between about 7.4 g/L and about 14.8 g/L, between about 7.4 g/L and about 14.6 g/L, between about 7.4 g/L and about 14.4 g/L, between about 7.4 g/L and about 14.2 g/L, between about 7.4 g/L and about 14.0 g/L, between about 7.4 g/L and about 13.8 g/L, between about 7.4 g/L and about 13.6 g/L, between about 7.4 g/L and about 13.4 g/L, between about 7.4 g/L and about 13.2 g/L, between about 7.4 g/L and about 13.0 g/L, between about 7.4 g/L and about 12.8 g/L, between about 7.4 g/L and about 12.6 g/L, between about 7.4 g/L and about 12.4 g/L, between about 7.4 g/L and about 12.2 g/L, between about 7.4 g/L and about 12.0 g/L, between about 7.4 g/L and about 11.8 g/L, between about 7.4 g/L and about 11.6 g/L, between about 7.4 g/L and about 11.4 g/L, between about 7.4 g/L and about 11.2 g/L, between about 7.4 g/L and about 11.0 g/L, between about 7.4 g/L and about 10.8 g/L, between about 7.4 g/L and about 10.6 g/L. between about 7.4 g/L and about 10.4 g/L, between about 7.4 g/L and about 10.2 g/L, between about 7.4 g/L and about 10.0 g/L, between about 7.4 g/L and about 9.8 g/L, between about 7.4 g/L and about 9.6 g/L, between about 7.4 g/L and about 9.4 g/L, between about 7.4 g/L and about 9.2 g/L, between about 7.4 g/L and about 9.0 g/L, between about 7.4 g/L and about 8.8 g/L, between about 7.4 g/L and about 8.6 g/L, between about 7.4 g/L and about 8.4 g/L, between about 7.6 g/L and about 16.0 g/L, between about 7.6 g/L and about 15.8 g/L, between about 7.6 g/L and about 15.6 g/L, between about 7.6 g/L and about 15.4 g/L, between about 7.6 g/L and about 15.2 g/L, between about 7.6 g/L and about 15.0 g/L, between about 7.6 g/L and about 14.8 g/L, between about 7.6 g/L and about 14.6 g/L, between about 7.6 g/L and about 14.4 g/L, between about 7.6 g/L and about 14.2 g/L, between about 7.6 g/L and about 14.0 g/L, between about 7.6 g/L and about 13.8 g/L, between about 7.6 g/L and about 13.6 g/L, between about 7.6 g/L and about 13.4 g/L, between about 7.6 g/L and about 13.2 g/L, between about 7.6 g/L and about 13.0 g/L, between about 7.6 g/L and about 12.8 g/L, between about 7.6 g/L and about 12.6 g/L, between about 7.6 g/L and about 12.4 g/L, between about 7.6 g/L and about 12.2 g/L, between about 7.6 g/L and about 12.0 g/L, between about 7.6 g/L and about 11.8 g/L, between about 7.6 g/L and about 11.6 g/L, between about 7.6 g/L and about 11.4 g/L, between about 7.6 g/L and about 11.2 g/L, between about 7.6 g/L and about 11.0 g/L, between about 7.6 g/L and about 10.8 g/L, between about 7.6 g/L and about 10.6 g/L. between about 7.6 g/L and about 10.4 g/L, between about 7.6 g/L and about 10.2 g/L, between about 7.6 g/L and about 10.0 g/L, between about 7.6 g/L and about 9.8 g/L, between about 7.6 g/L and about 9.6 g/L, between about 7.6 g/L and about 9.4 g/L, between about 7.6 g/L and about 9.2 g/L, between about 7.6 g/L and about 9.0 g/L, between about 7.6 g/L and about 8.8 g/L, between about 7.6 g/L and about 8.6 g/L, between about 7.8 g/L and about 16.0 g/L, between about 7.8 g/L and about 15.8 g/L, between about 7.8 g/L and about 15.6 g/L, between about 7.8 g/L and about 15.4 g/L, between about 7.8 g/L and about 15.2 g/L, between about 7.8 g/L and about 15.0 g/L, between about 7.8 g/L and about 14.8 g/L, between about 7.8 g/L and about 14.6 g/L, between about 7.8 g/L and about 14.4 g/L, between about 7.8 g/L and about 14.2 g/L, between about 7.8 g/L and about 14.0 g/L, between about 7.8 g/L and about 13.8 g/L, between about 7.8 g/L and about 13.6 g/L, between about 7.8 g/L and about 13.4 g/L, between about 7.8 g/L and about 13.2 g/L, between about 7.8 g/L and about 13.0 g/L, between about 7.8 g/L and about 12.8 g/L, between about 7.8 g/L and about 12.6 g/L, between about 7.8 g/L and about 12.4 g/L, between about 7.8 g/L and about 12.2 g/L, between about 7.8 g/L and about 12.0 g/L, between about 7.8 g/L and about 11.8 g/L, between about 7.8 g/L and about 11.6 g/L, between about 7.8 g/L and about 11.4 g/L, between about 7.8 g/L and about 11.2 g/L, between about 7.8 g/L and about 11.0 g/L, between about 7.8 g/L and about 10.8 g/L, between about 7.8 g/L and about 10.6 g/L. between about 7.8 g/L and about 10.4 g/L, between about 7.8 g/L and about 10.2 g/L, between about 7.8 g/L and about 10.0 g/L, between about 7.8 g/L and about 9.8 g/L, between about 7.8 g/L and about 9.6 g/L, between about 7.8 g/L and about 9.4 g/L, between about 7.8 g/L and about 9.2 g/L, between about 7.8 g/L and about 9.0 g/L, between about 7.8 g/L and about 8.8 g/L, between about 8.0 g/L and about 16.0 g/L, between about 8.0 g/L and about 15.8 g/L, between about 8.0 g/L and about 15.6 g/L, between about 8.0 g/L and about 15.4 g/L, between about 8.0 g/L and about 15.2 g/L, between about 8.0 g/L and about 15.0 g/L, between about 8.0 g/L and about 14.8 g/L, between about 8.0 g/L and about 14.6 g/L, between about 8.0 g/L and about 14.4 g/L, between about 8.0 g/L and about 14.2 g/L, between about 8.0 g/L and about 14.0 g/L, between about 8.0 g/L and about 13.8 g/L, between about 8.0 g/L and about 13.6 g/L, between about 8.0 g/L and about 13.4 g/L, between about 8.0 g/L and about 13.2 g/L, between about 8.0 g/L and about 13.0 g/L, between about 8.0 g/L and about 12.8 g/L, between about 8.0 g/L and about 12.6 g/L, between about 8.0 g/L and about 12.4 g/L, between about 8.0 g/L and about 12.2 g/L, between about 8.0 g/L and about 12.0 g/L, between about 8.0 g/L and about 11.8 g/L, between about 8.0 g/L and about 11.6 g/L, between about 8.0 g/L and about 11.4 g/L, between about 8.0 g/L and about 11.2 g/L, between about 8.0 g/L and about 11.0 g/L, between about 8.0 g/L and about 10.8 g/L, between about 8.0 g/L and about 10.6 g/L. between about 8.0 g/L and about 10.4 g/L, between about 8.0 g/L and about 10.2 g/L, between about 8.0 g/L and about 10.0 g/L, between about 8.0 g/L and about 9.8 g/L, between about 8.0 g/L and about 9.6 g/L, between about 8.0 g/L and about 9.4 g/L, between about 8.0 g/L and about 9.2 g/L, between about 8.0 g/L and about 9.0 g/L, between about 8.5 g/L and about 16.0 g/L, between about 8.5 g/L and about 15.5 g/L, between about 8.5 g/L and about 15.0 g/L, between about 8.5 g/L and about 14.5 g/L, between about 8.5 g/L and about 14.0 g/L, between about 8.5 g/L and about 13.5 g/L, between about 8.5 g/L and about 13.0 g/L, between about 8.5 g/L and about 12.5 g/L, between about 8.5 g/L and about 12.0 g/L, between about 8.5 g/L and about 11.5 g/L, between about 8.5 g/L and about 11.0 g/L, between about 8.5 g/L and about 10.5 g/L, between about 8.5 g/L and about 10.0 g/L, between about 8.5 g/L and about 9.5 g/L, between about 9.0 g/L and about 16.0 g/L, between about 9.0 g/L and about 15.5 g/L, between about 9.0 g/L and about 15.0 g/L, between about 9.0 g/L and about 14.5 g/L, between about 9.0 g/L and about 14.0 g/L, between about 9.0 g/L and about 13.5 g/L, between about 9.0 g/L and about 13.0 g/L, between about 9.0 g/L and about 12.5 g/L, between about 9.0 g/L and about 12.0 g/L, between about 9.0 g/L and about 11.5 g/L, between about 9.0 g/L and about 11.0 g/L, between about 9.0 g/L and about 10.5 g/L, between about 9.0 g/L and about 10.0 g/L, between about 9.5 g/L and about 16.0 g/L, between about 9.5 g/L and about 15.5 g/L, between about 9.5 g/L and about 15.0 g/L, between about 9.5 g/L and about 14.5 g/L, between about 9.5 g/L and about 14.0 g/L, between about 9.5 g/L and about 13.5 g/L, between about 9.5 g/L and about 13.0 g/L, between about 9.5 g/L and about 12.5 g/L, between about 9.5 g/L and about 12.0 g/L, between about 9.5 g/L and about 11.5 g/L, between about 9.5 g/L and about 11.0 g/L, between about 9.5 g/L and about 10.5 g/L, between about 10.0 g/L and about 16.0 g/L, between about 10.0 g/L and about 15.5 g/L, between about 10.0 g/L and about 15.0 g/L, between about 10.0 g/L and about 14.5 g/L, between about 10.0 g/L and about 14.0 g/L, between about 10.0 g/L and about 13.5 g/L, between about 10.0 g/L and about 13.0 g/L, between about 10.0 g/L and about 12.5 g/L, between about 10.0 g/L and about 12.0 g/L, between about 10.0 g/L and about 11.5 g/L, between about 10.0 g/L and about 11.0 g/L, between about 10.5 g/L and about 16.0 g/L, between about 10.5 g/L and about 15.5 g/L, between about 10.5 g/L and about 15.0 g/L, between about 10.5 g/L and about 14.5 g/L, between about 10.5 g/L and about 14.0 g/L, between about 10.5 g/L and about 13.5 g/L, between about 10.5 g/L and about 13.0 g/L, between about 10.5 g/L and about 12.5 g/L, between about 10.5 g/L and about 12.0 g/L, between about 10.5 g/L and about 11.5 g/L, between about 11.0 g/L and about 16.0 g/L, between about 11.0 g/L and about 15.5 g/L, between about 11.0 g/L and about 15.0 g/L, between about 11.0 g/L and about 14.5 g/L, between about 11.0 g/L and about 14.0 g/L, between about 11.0 g/L and about 13.5 g/L, between about 11.0 g/L and about 13.0 g/L, between about 11.0 g/L and about 12.5 g/L, between about 11.0 g/L and about 12.0 g/L, between about 11.5 g/L and about 16.0 g/L, between about 11.5 g/L and about 15.5 g/L, between about 11.5 g/L and about 15.0 g/L, between about 11.5 g/L and about 14.5 g/L, between about 11.5 g/L and about 14.0 g/L, between about 11.5 g/L and about 13.5 g/L, between about 11.5 g/L and about 13.0 g/L, between about 11.5 g/L and about 12.5 g/L, between about 12.0 g/L and about 16.0 g/L, between about 12.0 g/L and about 15.5 g/L, between about 12.0 g/L and about 15.0 g/L, between about 12.0 g/L and about 14.5 g/L, between about 12.0 g/L and about 14.0 g/L, between about 12.0 g/L and about 13.5 g/L, between about 12.0 g/L and about 13.0 g/L, between about 12.5 g/L and about 16.0 g/L, between about 12.5 g/L and about 15.5 g/L, between about 12.5 g/L and about 15.0 g/L, between about 12.5 g/L and about 14.5 g/L, between about 12.5 g/L and about 14.0 g/L, between about 12.5 g/L and about 13.5 g/L, between about 13.0 g/L and about 16.0 g/L, between about 13.0 g/L and about 15.5 g/L, between about 13.0 g/L and about 15.0 g/L, between about 13.0 g/L and about 14.5 g/L, between about 13.0 g/L and about 14.0 g/L, between about 13.5 g/L and about 16.0 g/L, between about 13.5 g/L and about 15.5 g/L, between about 13.5 g/L and about 15.0 g/L, between about 13.5 g/L and about 14.5 g/L, between about 14.0 g/L and about 16.0 g/L, between about 14.0 g/L and about 15.5 g/L, between about 14.0 g/L and about 15.0 g/L, between about 14.5 g/L and about 16.0 g/L, between about 14.5 g/L and about 15.5 g/L, or between about 15.0 g/L and about 16.0 g/L).

In some embodiments, the poloxamer-188 is present in the medium and/or added to the medium prior to the culturing step and/or is added to the medium during the culturing step. For example, the methods provided herein can further include adding poloxamer-188 prior to and/or during the culturing step to provide a concentration of 1.8 g/L or more (e.g., any of the exemplary concentrations of poloxamer-188 or ranges of poloxamer-188 described herein) in the medium. In some examples, additional poloxamer-188 is added to a liquid medium including some poloxamer-188 in order to provide a concentration of 1.8 g/L or more poloxamer-188 (e.g., any of the exemplary concentrations of poloxamer-188 or ranges of poloxamer-188 described herein). For example, poloxamer-188 can be added to a first liquid medium, a second liquid medium, and/or a feed liquid medium prior to and/or during the culturing step.

In some examples, the poloxamer-188 is added to a medium in one or more (e.g., two, three, four, or five) aliquots during the culturing step. The poloxamer-188 can be added to the medium in a continuous manner. In some examples, the first liquid medium can contain poloxamer-188, and additional poloxamer-188 is added to the medium during the culturing period. In some embodiments, the poloxamer-188 is present in the medium.

When the culturing step includes perfusion culturing, the second liquid medium can include poloxamer-188 at a greater concentration than that in the first liquid medium. For example, the first liquid medium can include poloxamer-188 at a concentration of 1.8 g/L or at a concentration or less than 1.8 g/L, and the second liquid medium includes poloxamer-188 at a greater concentration than 1.8 g/L (e.g., any of the concentrations or ranges of poloxamer-188 described herein, e.g., a greater concentration than 1.9 g/L, a greater concentration than 2.0 g/L, a greater concentration than 2.1 g/L, a greater concentration than 2.2 g/L, a greater concentration than 2.3 g/L, a greater concentration than 2.4 g/L, a greater concentration than 2.5 g/L, a greater concentration than 2.6 g/L, a greater concentration than 2.7 g/L, a greater concentration than 2.8 g/L, a greater concentration than 2.9 g/L, a greater concentration than 3.0 g/L, a greater concentration than 3.1 g/L, a greater concentration than 3.2 g/L, a greater concentration than 3.3 g/L, a greater concentration than 3.4 g/L, a greater concentration than 3.5 g/L, a greater concentration than 3.6 g/L, a greater concentration than 3.7 g/L, a greater concentration than 3.8 g/L, a greater concentration than 3.9 g/L, a greater concentration than 4.0 g/L, a greater concentration than 4.1 g/L, a greater concentration than 4.2 g/L, a greater concentration than 4.3 g/L, a greater concentration than 4.4 g/L, a greater concentration than 4.5 g/L, a greater concentration than 4.6 g/L, a greater concentration than 4.7 g/L, a greater concentration than 4.8 g/L, a greater concentration than 4.9 g/L, a greater concentration than 5.0 g/L, a greater concentration than 5.1 g/L, a greater concentration than 5.2 g/L, a greater concentration than 5.3 g/L, a greater concentration than 5.4 g/L, a greater concentration than 5.5 g/L, a greater concentration than 5.6 g/L, a greater concentration than 5.7 g/L, a greater concentration than 5.8 g/L, a greater concentration than 5.9 g/L, a greater concentration than 6.0 g/L, a greater concentration than 6.1 g/L, a greater concentration than 6.2 g/L, a greater concentration than 6.3 g/L, a greater concentration than 6.4 g/L, a greater concentration than 6.5 g/L, a greater concentration than 6.6 g/L, a greater concentration than 6.7 g/L, a greater concentration than 6.8 g/L, a greater concentration than 6.9 g/L, a greater concentration than 7.0 g/L, a greater concentration than 7.1 g/L, a greater concentration than 7.2 g/L, a greater concentration than 7.3 g/L, a greater concentration than 7.4 g/L, a greater concentration than 7.5 g/L, a greater concentration than 7.6 g/L, a greater concentration than 7.7 g/L, a greater concentration than 7.8 g/L, a greater concentration than 7.9 g/L, a greater concentration than 8.0 g/L, a greater concentration than 8.1 g/L, a greater concentration than 8.2 g/L, a greater concentration than 8.3 g/L, a greater concentration than 8.4 g/L, a greater concentration than 8.5 g/L, a greater concentration than 8.6 g/L, a greater concentration than 8.7 g/L, a greater concentration than 8.8 g/L, a greater concentration than 8.9 g/L, a greater concentration than 9.0 g/L, a greater concentration than 9.1 g/L, a greater concentration than 9.2 g/L, a greater concentration than 9.3 g/L, a greater concentration than 9.4 g/L, a greater concentration than 9.5 g/L, a greater concentration than 9.6 g/L, a greater concentration than 9.7 g/L, a greater concentration than 9.8 g/L, a greater concentration than 9.9 g/L, a greater concentration than 10.0 g/L, a greater concentration than 10.1 g/L, a greater concentration than 10.2 g/L, a greater concentration than 10.3 g/L, a greater concentration than 10.4 g/L, a greater concentration than 10.5 g/L, a greater concentration than 10.6 g/L, a greater concentration than 10.7 g/L, a greater concentration than 10.8 g/L, a greater concentration than 10.9 g/L, a greater concentration than 11.0 g/L, a greater concentration than 11.1 g/L. a greater concentration than 11.2 g/L, a greater concentration than 11.3 g/L, a greater concentration than 11.4 g/L, a greater concentration than 11.5 g/L, a greater concentration than 11.6 g/L, a greater concentration than 11.7 g/L, a greater concentration than 11.8 g/L, a greater concentration than 11.9 g/L, a greater concentration than 12.0 g/L, a greater concentration than 12.1 g/L, a greater concentration than 12.2 g/L, a greater concentration than 12.3 g/L, a greater concentration than 12.4 g/L, a greater concentration than 12.5 g/L, a greater concentration than 12.6 g/L, a greater concentration than 12.7 g/L, a greater concentration than 12.8 g/L, a greater concentration than 12.9 g/L, a greater concentration than 13.0 g/L, a greater concentration than 13.1 g/L, a greater concentration than 13.2 g/L, a greater concentration than 13.3 g/L, a greater concentration than 13.4 g/L, a greater concentration than 13.5 g/L, a greater concentration than 13.6 g/L, a greater concentration than 13.7 g/L, a greater concentration than 13.8 g/L, a greater concentration than 13.9 g/L, a greater concentration than 14.0 g/L, a greater concentration than 14.1 g/L, a greater concentration than 14.2 g/L, a greater concentration than 14.3 g/L, a greater concentration than 14.4 g/L, a greater concentration than 14.5 g/L, a greater concentration than 14.6 g/L, a greater concentration than 14.7 g/L, a greater concentration than 14.8 g/L, a greater concentration than 14.9 g/L, a greater concentration than 15.0 g/L, a greater concentration than 15.1 g/L, a greater concentration than 15.2 g/L, a greater concentration than 15.3 g/L, a greater concentration than 15.4 g/L, a greater concentration than 15.5 g/L, a greater concentration than 15.6 g/L, a greater concentration than 15.7 g/L, a greater concentration than 15.8 g/L, a greater concentration than 15.9 g/L, or a greater concentration than 16.0 g/L poloxamer-188).

When the culturing step includes feed batch culturing, the feed liquid medium can include poloxamer-188 at a greater concentration than that in the first liquid medium. For example, the first liquid medium can include poloxamer-188 at a concentration of 1.8 g/L or at a concentration of less than 1.8 g/L, and the feed liquid medium includes poloxamer-188 at a greater concentration than 1.8 g/L (e.g., a greater concentration than 2.0 g/L, a greater concentration than 2.5 g/L, a greater concentration than 3.0 g/L, a greater concentration than 3.5 g/L, a greater concentration than 4.0 g/L, a greater concentration than 4.5 g/L, a greater concentration than 5.0 g/L, a greater concentration than 5.5 g/L, a greater concentration than 6.0 g/L, a greater concentration than 6.5 g/L, a greater concentration than 7.0 g/L, a greater concentration than 7.5 g/L, a greater concentration than 8.0 g/L, a greater concentration than 8.5 g/L, a greater concentration than 9.0 g/L, a greater concentration than 9.5 g/L, a greater concentration than 10 g/L, a greater concentration than 10.5 g/L, a greater concentration than 11.0 g/L, a greater concentration than 11.5 g/L, a greater concentration than 12.0 g/L, a greater concentration than 12.5 g/L, a greater concentration than 13.0 g/L, a greater concentration than 13.5 g/L, a greater concentration than 14.0 g/L, a greater concentration than 14.5 g/L, a greater concentration than 15.0 g/L, a greater concentration than 15.5 g/L, a greater concentration than 16.0 g/L, a greater concentration than 16.5 g/L, a greater concentration than 17.0 g/L, a greater concentration than 17.5 g/L, a greater concentration than 18.0 g/L, a greater concentration than 18.5 g/L, a greater concentration than 19.0 g/L, a greater concentration than 19.5 g/L, a greater concentration than 20.0 g/L, a greater concentration than 20.5 g/L, a greater concentration than 21.0 g/L, a greater concentration than 21.5 g/L, a greater concentration than 22.0 g/L, a greater concentration than 22.5 g/L, a greater concentration than 23.0 g/L, a greater concentration than 23.5 g/L, a greater concentration than 24.0 g/L, a greater concentration than 24.5 g/L, a greater concentration than 25.0 g/L, a greater concentration than 25.5 g/L, a greater concentration than 26.0 g/L, a greater concentration than 26.5 g/L, a greater concentration than 27.0 g/L, a greater concentration than 28.0 g/L, a greater concentration than 28.5 g/L, a greater concentration than 29.0 g/L, a greater concentration than 29.5 g/L, a greater concentration than 30.0 g/L, a greater concentration than 30.5 g/L, a greater concentration than 31.0 g/L, a greater concentration than 31.5 g/L, a greater concentration than 32.0 g/L, a greater concentration than 32.5 g/L, a greater concentration than 33.0 g/L, a greater concentration than 33.5 g/L, a greater concentration than 34.0 g/L, a greater concentration than 34.5 g/L, a greater concentration than 35.0 g/L, a greater concentration than 35.5 g/L, a greater concentration than 36.0 g/L, a greater concentration than 36.5 g/L, a greater concentration than 37.0 g/L, a greater concentration than 37.5 g/L, a greater concentration than 38.0 g/L, a greater concentration than 38.5 g/L, a greater concentration than 39.0 g/L, a greater concentration than 39.5 g/L. or a greater concentration than 40.0 g/L).

Some embodiments of any of the methods provided herein include increasing the poloxamer-188 concentration in the culture over time. In some embodiments, the medium includes a poloxamer-188 concentration that is selected based on one or more factors selected from the group of: pore size, pore type, gas flow rate, viable cell density in the medium, and markers related to cell stress. In these methods, the selected poloxamer-188 concentration in the medium can be achieved by adding poloxamer-188 to the medium prior to the culturing step and/or by adding poloxamer-188 to the medium during the culturing step. The selected poloxmer-188 concentration can be any of the exemplary concentrations or ranges of poloxamer-188 described herein.

Selecting Concentration of Poloxamer-188 Based on One or More Factors

Some embodiments of the methods described herein include culturing a mammalian cell in a liquid medium including a poloxamer-188 concentration that is selected based on one or more factors selected from the group of: pore size, pore type, gas flow rate, viable cell density in the medium, and markers related to cell stress.

Different examples of pore types are known in the art. Non-limiting examples of pore types are sintered pores and drilled pores.

A variety of gas flow rates suitable for cell culturing are known in the art. Generally, a higher gas flow rate indicates that a higher poloxamer-188 concentration should be selected (as compared to a culturing step using a lower gas flow rate), and a lower gas flow rate indicates that a lower poloxamer-188 concentration should be selected (as compared to a culturing step using a higher gas flow rate).

A variety of non-limiting viable cell densities are described herein. Generally, a higher viable cell density indicates that a higher poloxamer-188 concentration should be selected (as compared to a medium containing a lower viable cell density), and a lower viable cell density indicates that a lower poloxamer-188 concentration should be selected (as compared to a medium containing a higher viable cell density).

Exemplary markers of cell stress that are released by a cell under physiological stress include proteases (e.g., activated caspases), lactate dehydrogenase, genomic DNA (e.g., nucleosomal DNA), cytochrome c, and activated PARP. Non-limiting examples of markers related to cell stress that are produced or have elevated levels in a cell under physiological stress include activated caspases, cytochrome c, activated PARP, and externalized phosphatidylserine. Elevated levels of one or more (e.g., two, three, four, five, six, or seven) of any of these markers of cell stress as compared to a control value(s) indicate that a higher poloxamer-188 concentration should be selected. Level(s) of the one or more markers of cell stress as compared to a control value(s) that are about the same or below a control value(s) indicate lower poloxamer-188 concentration should be selected. In any of the examples describe herein, the control level can be a level in a control cell that is not undergoing apoptosis or is not cultured under conditions that would trigger necrosis. Methods for detecting the level of one or more markers of cell stress are well known in the art. Commercially available kits are available to measure the one or more markers of cell stress.

In any of the embodiments described herein, the selected poloxamer-188 concentration is achieved by adding poloxamer-188 to the medium prior to the culturing step and/or by adding poloxamer-188 to the medium during the culturing step. In some embodiments, the methods include selecting based on pore type and pore size a poloxamer-188 concentration of between about 2.3 g/L and about 3.3 g/L (e.g., between about 2.3 g/L and about 3.2 g/L, between about 2.3 g/L and about 3.1 g/L, between about 2.3 g/L and about 3.0 g/L, between about 2.3 g/L and about 2.9 g/L, between about 2.3 g/L and about 2.8 g/L, between about 2.3 g/L and about 2.7 g/L, between about 2.3 g/L and about 2.6 g/L, between about 2.3 g/L and about 2.5 g/L, between about 2.4 g/L and about 3.3 g/L, between about 2.4 g/L and about 3.2 g/L, between about 2.4 g/L and about 3.1 g/L, between about 2.4 g/L and about 3.0 g/L, between about 2.4 g/L and about 2.9 g/L, between about 2.4 g/L and about 2.8 g/L, between about 2.4 g/L and about 2.7 g/L, between about 2.4 g/L and about 2.6 g/L, between about 2.5 g/L and about 3.3 g/L, between about 2.5 g/L and about 3.2 g/L, between about 2.5 g/L and about 3.1 g/L, between about 2.5 g/L and about 3.0 g/L, between about 2.5 g/L and about 2.9 g/L, between about 2.5 g/L and about 2.8 g/L, between about 2.5 g/L and about 2.7 g/L, between about 2.6 g/L and about 3.3 g/L, between about 2.6 g/L and about 3.2 g/L, between about 2.6 g/L and about 3.1 g/L, between about 2.6 g/L and about 3.0 g/L, between about 2.6 g/L and about 2.9 g/L, between about 2.6 g/L and about 2.8 g/L, between about 2.7 g/L and about 3.3 g/L, between about 2.7 g/L and about 3.2 g/L, between about 2.7 g/L and about 3.1 g/L, between about 2.7 g/L and about 3.0 g/L, between about 2.7 g/L and about 2.9 g/L, between about 2.8 g/L and about 3.3 g/L, between about 2.8 g/L and about 3.2 g/L, between about 2.8 g/L and about 3.1 g/L, between about 2.8 g/L and about 3.0 g/L, between about 2.9 g/L and about 3.3 g/L, between about 2.9 g/L and about 3.2 g/L, between about 2.9 g/L and about 3.1 g/L, between about 3.0 g/L and about 3.3 g/L, between about 3.0 g/L and about 3.2 g/L, or between about 3.1 g/L and about 3.3 g/L), when the pore type is a drilled pore and the pore size is between about 750 μm and about 1.5 mm (e.g., between about 750 μm to about 1.45 mm, between about 750 μm and about 1.40 mm, between about 750 μm and about 1.35 mm, between about 750 μm and about 1.30 mm, between about 750 μm and about 1.25 mm, between about 750 μm and about 1.20 mm, between about 750 μm and about 1.15 mm, between about 750 μm and about 1.10 mm, between about 750 μm and about 1.05 mm, between about 750 μm and about 1.00 mm, between about 750 μm and about 950 μm, between about 750 μm and about 900 μm, between about 750 μm and about 850 μm, between about 750 μm and about 800 μm, between about 800 μm and about 1.5 mm, between about 800 μm and about 1.45 mm, between about 800 μm and about 1.40 mm, between about 800 μm and about 1.35 mm, between about 800 μm and about 1.30 mm, between about 800 μm and about 1.25 mm, between about 800 μm and about 1.20 mm, between about 800 μm and about 1.15 mm, between about 800 μm and about 1.10 mm, between about 800 μm and about 1.05 mm, between about 800 μm and about 1.00 mm, between about 800 μm and about 950 μm, between about 800 μm and about 900 μm, between about 800 μm and about 850 μm, between about 850 μm and about 1.5 mm, between about 850 μm and about 1.45 mm, between about 850 μm and about 1.40 mm, between about 850 μm and about 1.35 mm, between about 850 μm and about 1.30 mm, between about 850 μm and about 1.25 mm, between about 850 μm and about 1.20 mm, between about 850 μm and about 1.15 mm, between about 850 μm and about 1.10 mm, between about 850 μm and about 1.05 mm, between about 850 μm and about 1.00 mm, between about 850 μm and about 950 μm, between about 850 μm and about 900 μm, between about 900 μm and about 1.5 mm, between about 900 μm and about 1.45 mm, between about 900 μm and about 1.40 mm, between about 900 μm and about 1.35 mm, between about 900 μm and about 1.30 mm, between about 900 μm and about 1.25 mm, between about 900 μm and about 1.20 mm, between about 900 μm and about 1.15 mm, between about 900 μm and about 1.10 mm, between about 900 μm and about 1.05 mm, between about 900 μm and about 1.00 mm, between about 900 μm and about 950 μm, between about 950 μm and about 1.5 mm, between about 950 μm and about 1.45 mm, between about 950 μm and about 1.40 mm, between about 950 μm and about 1.35 mm, between about 950 μm and about 1.30 mm, between about 950 μm and about 1.25 mm, between about 950 μm and about 1.20 mm, between about 950 μm and about 1.15 mm, between about 950 μm and about 1.10 mm, between about 950 μm and about 1.05 mm, between about 950 μm and about 1.00 mm, between about 1.0 mm and about 1.5 mm, between about 1.0 mm and about 1.45 mm, between about 1.0 mm and about 1.40 mm, between about 1.0 mm and about 1.35 mm, between about 1.0 mm and about 1.30 mm, between about 1.0 mm and about 1.25 mm, between about 1.0 mm and about 1.20 mm, between about 1.0 mm and about 1.15 mm, between about 1.0 mm and about 1.10 mm, between about 1.0 mm and about 1.05 mm, between about 1.05 mm and about 1.5 mm, between about 1.05 mm and about 1.45 mm, between about 1.05 mm and about 1.40 mm, between about 1.05 mm and about 1.35 mm, between about 1.05 mm and about 1.30 mm, between about 1.05 mm and about 1.25 mm, between about 1.05 mm and about 1.20 mm, between about 1.05 mm and about 1.15 mm, between about 1.05 mm and about 1.10 mm, between about 1.10 mm and about 1.5 mm, between about 1.10 mm and about 1.45 mm, between about 1.10 mm and about 1.40 mm, between about 1.10 mm and about 1.35 mm, between about 1.10 mm and about 1.30 mm, between about 1.10 mm and about 1.25 mm, between about 1.10 mm and about 1.20 mm, between about 1.10 mm and about 1.15 mm, between about 1.15 mm and about 1.5 mm, between about 1.15 mm and about 1.45 mm, between about 1.15 mm and about 1.40 mm, between about 1.15 mm and about 1.35 mm, between about 1.15 mm and about 1.30 mm, between about 1.15 mm and about 1.25 mm, between about 1.15 mm and about 1.20 mm, between about 1.20 mm and about 1.5 mm, between about 1.20 mm and about 1.45 mm, between about 1.20 mm and about 1.40 mm, between about 1.20 mm and about 1.35 mm, between about 1.20 mm and about 1.30 mm, between about 1.20 mm and about 1.25 mm, between about 1.25 mm and about 1.5 mm, between about 1.25 mm and about 1.45 mm, between about 1.25 mm and about 1.40 mm, between about 1.25 mm and about 1.35 mm, between about 1.25 mm and about 1.30 mm, between about 1.30 mm and about 1.5 mm, between about 1.30 mm and about 1.45 mm, between about 1.30 mm and about 1.40 mm, between about 1.30 mm and about 1.35 mm, between about 1.35 mm and about 1.5 mm, between about 1.35 mm and about 1.45 mm, between about 1.35 mm and about 1.40 mm, between about 1.40 mm and about 1.5 mm, between about 1.40 mm and about 1.45 mm, or between about 1.45 mm and about 1.50).

In some embodiments, the methods include selecting based on pore type and pore size a poloxamer-188 concentration of between about 3.3 g/L and about 4.3 g/L (e.g., between about 3.3 g/L and about 4.2 g/L, between about 3.3 g/L and about 4.1 g/L, between about 3.3 g/L and about 4.0 g/L, between about 3.3 g/L and about 3.9 g/L, between about 3.3 g/L and about 3.8 g/L, between about 3.3 g/L and about 3.7 g/L, between about 3.3 g/L and about 3.6 g/L, between about 3.3 g/L and about 3.5 g/L, between about 3.4 g/L and about 4.3 g/L, between about 3.4 g/L and about 4.2 g/L, between about 3.4 g/L and about 4.1 g/L, between about 3.4 g/L and about 4.0 g/L, between about 3.4 g/L and about 3.9 g/L, between about 3.4 g/L and about 3.8 g/L, between about 3.4 g/L and about 3.7 g/L, between about 3.4 g/L and about 3.6 g/L, between about 3.5 g/L and about 4.3 g/L, between about 3.5 g/L and about 4.2 g/L, between about 3.5 g/L and about 4.1 g/L, between about 3.5 g/L and about 4.0 g/L, between about 3.5 g/L and about 3.9 g/L, between about 3.5 g/L and about 3.8 g/L, between about 3.5 g/L and about 3.7 g/L, between about 3.6 g/L and about 4.3 g/L, between about 3.6 g/L and about 4.2 g/L, between about 3.6 g/L and about 4.1 g/L, between about 3.6 g/L and about 4.0 g/L, between about 3.6 g/L and about 3.9 g/L, between about 3.6 g/L and about 3.8 g/L, between about 3.7 g/L and about 4.3 g/L, between about 3.7 g/L and about 4.2 g/L, between about 3.7 g/L and about 4.1 g/L, between about 3.7 g/L and about 4.0 g/L, between about 3.7 g/L and about 3.9 g/L, between about 3.8 g/L and about 4.3 g/L, between about 3.8 g/L and about 4.2 g/L, between about 3.8 g/L and about 4.1 g/L, between about 3.8 g/L and about 4.0 g/L, between about 3.9 g/L and about 4.3 g/L, between about 3.9 g/L and about 4.2 g/L, between about 3.9 g/L and about 4.1 g/L, between about 4.0 g/L and about 4.3 g/L, between about 4.0 g/L and about 4.2 g/L, or between about 4.1 g/L and about 4.3 g/L), when the pore type is a drilled pore and the pore size is between about 250 μm and about 750 μm (e.g., between about 250 μm and about 700 μm, between about 250 μm and about 650 μm, between about 250 μm and about 600 μm, between about 250 μm and about 550 μm, between about 250 μm and about 500 μm, between about 250 μm and about 450 μm, between about 250 μm and about 400 μm, between about 250 μm and about 350 μm, between about 250 μm and about 300 μm, between about 300 μm and about 750 μm, between about 300 μm and about 700 μm, between about 300 μm and about 650 μm, between about 300 μm and about 600 μm, between about 300 μm and about 550 μm, between about 300 μm and about 500 μm, between about 300 μm and about 450 μm, between about 300 μm and about 400 μm, between about 300 μm and about 350 μm, between about 350 μm and about 750 μm, between about 350 μm and about 700 μm, between about 350 μm and about 650 μm, between about 350 μm and about 600 μm, between about 350 μm and about 550 μm, between about 350 μm and about 500 μm, between about 350 μm and about 450 μm, between about 350 μm and about 400 μm, between about 400 μm and about 750 μm, between about 400 μm and about 700 μm, between about 400 μm and about 650 μm, between about 400 μm and about 600 μm, between about 400 μm and about 550 μm, between about 400 μm and about 500 μm, between about 400 μm and about 450 μm, between about 450 μm and about 750 μm, between about 450 μm and about 700 μm, between about 450 μm and about 650 μm, between about 450 μm and about 600 μm, between about 450 μm and about 550 μm, between about 450 μm and about 500 μm, between about 500 μm and about 750 μm, between about 500 μm and about 700 μm, between about 500 μm and about 650 μm, between about 500 μm and about 600 μm, between about 500 μm and about 550 μm, between about 550 μm and about 750 μm, between about 550 μm and about 700 μm, between about 550 μm and about 650 μm, between about 550 μm and about 600 μm, between about 600 μm and about 750 μm, between about 600 μm and about 700 μm, between about 600 μm and about 650 μm, between about 650 μm and about 750 μm, between about 650 μm and about 700 μm, or between about 700 μm and 750 μm).

The methods can include, e.g., selecting based on pore type and pore size poloxamer-188 at a greater concentration than about 4.3 g/L (e.g., a greater concentration than about 4.4 g/L, a greater concentration than about 4.5 g/L, a greater concentration than about 4.6 g/L, a greater concentration than about 4.7 g/L, a greater concentration than about 4.8 g/L, a greater concentration than about 4.9 g/L, a greater concentration than about 5.0 g/L, a greater concentration than about 5.1 g/L, a greater concentration than about 5.2 g/L, a greater concentration than about 5.3 g/L, a greater concentration than about 5.4 g/L, a greater concentration than about 5.5 g/L, a greater concentration than about 5.6 g/L, a greater concentration than about 5.7 g/L, a greater concentration than about 5.8 g/L, a greater concentration than about 5.9 g/L, a greater concentration than about 6.0 g/L, a greater concentration than about 6.1 g/L, a greater concentration than about 6.2 g/L, a greater concentration than about 6.3 g/L, a greater concentration than about 6.4 g/L, a greater concentration than about 6.5 g/L, a greater concentration than about 6.6 g/L, a greater concentration than about 6.7 g/L, a greater concentration than about 6.8 g/L, a greater concentration than about 6.9 g/L, a greater concentration than about 7.0 g/L, a greater concentration than about 7.1 g/L, a greater concentration than about 7.2 g/L, a greater concentration than about 7.3 g/L, a greater concentration than about 7.4 g/L, a greater concentration than about 7.5 g/L, a greater concentration than about 7.6 g/L, a greater concentration than about 7.7 g/L, a greater concentration than about 7.8 g/L, a greater concentration than about 7.9 g/L, a greater concentration than about 8.0 g/L, a greater concentration than about 8.1 g/L, a greater concentration than about 8.2 g/L, a greater concentration than about 8.2 g/L, a greater concentration than about 8.3 g/L, a greater concentration than about 8.4 g/L, a greater concentration than about 8.5 g/L, a greater concentration than about 8.6 g/L, a greater concentration than about 8.7 g/L, a greater concentration than about 8.8 g/L, a greater concentration than about 8.9 g/L, a greater concentration than about 9.0 g/L, a greater concentration than about 9.1 g/L, a greater concentration than about 9.2 g/L, a greater concentration than about 9.3 g/L, a greater concentration than about 9.4 g/L, a greater concentration than about 9.5 g/L, a greater concentration than about 9.6 g/L, a greater concentration than about 9.7 g/L, a greater concentration than about 9.8 g/L, a greater concentration than about 9.9 g/L, or a greater concentration than about 10.0 g/L), when the pore type is a drilled pore and the pore size is between about 1 nm and about 250 nm (e.g., between about 1 nm and about 200 nm, between about 1 nm and about 150 nm, between about 1 nm and about 100 nm, between about 1 nm and about 50 nm, between about 1 nm and about 25 nm, between about 10 nm and about 250 nm, between about 10 nm and about 200 μm, between about 10 nm and about 150 nm, between about 10 nm and about 100 nm, between about 10 nm and about 50 nm, between about 10 nm and about 25 nm, between about 25 nm and about 250 nm, between about 25 nm and about 200 nm, between about 25 nm and about 150 nm, between about 25 nm and about 100 nm, between about 25 nm and about 50 nm, between about 50 nm and about 250 nm, between about 50 nm and about 200 nm, between about 50 nm and about 150 nm, between about 50 nm and about 100 nm, between about 100 nm and about 250 nm, between about 100 nm and about 200 μm, between about 100 nm and about 150 nm, between about 150 nm and about 250 μm, between about 150 nm and about 200 nm, or between about 200 nm and about 250 nm).

In some examples, the methods include selecting based on pore type and pore size poloxamer-188 at a greater concentration than 4.3 g/L (e.g., a greater concentration than about 4.4 g/L, a greater concentration than about 4.5 g/L, a greater concentration than about 4.6 g/L, a greater concentration than about 4.7 g/L, a greater concentration than about 4.8 g/L, a greater concentration than about 4.9 g/L, a greater concentration than about 5.0 g/L, a greater concentration than about 5.1 g/L, a greater concentration than about 5.2 g/L, a greater concentration than about 5.3 g/L, a greater concentration than about 5.4 g/L, a greater concentration than about 5.5 g/L, a greater concentration than about 5.6 g/L, a greater concentration than about 5.7 g/L, a greater concentration than about 5.8 g/L, a greater concentration than about 5.9 g/L, a greater concentration than about 6.0 g/L, a greater concentration than about 6.1 g/L, a greater concentration than about 6.2 g/L, a greater concentration than about 6.3 g/L, a greater concentration than about 6.4 g/L, a greater concentration than about 6.5 g/L, a greater concentration than about 6.6 g/L, a greater concentration than about 6.7 g/L, a greater concentration than about 6.8 g/L, a greater concentration than about 6.9 g/L, a greater concentration than about 7.0 g/L, a greater concentration than about 7.1 g/L, a greater concentration than about 7.2 g/L, a greater concentration than about 7.3 g/L, a greater concentration than about 7.4 g/L, a greater concentration than about 7.5 g/L, a greater concentration than about 7.6 g/L, a greater concentration than about 7.7 g/L, a greater concentration than about 7.8 g/L, a greater concentration than about 7.9 g/L, a greater concentration than about 8.0 g/L, a greater concentration than about 8.1 g/L, a greater concentration than about 8.2 g/L, a greater concentration than about 8.2 g/L, a greater concentration than about 8.3 g/L, a greater concentration than about 8.4 g/L, a greater concentration than about 8.5 g/L, a greater concentration than about 8.6 g/L, a greater concentration than about 8.7 g/L, a greater concentration than about 8.8 g/L, a greater concentration than about 8.9 g/L, a greater concentration than about 9.0 g/L, a greater concentration than about 9.1 g/L, a greater concentration than about 9.2 g/L, a greater concentration than about 9.3 g/L, a greater concentration than about 9.4 g/L, a greater concentration than about 9.5 g/L, a greater concentration than about 9.6 g/L, a greater concentration than about 9.7 g/L, a greater concentration than about 9.8 g/L, a greater concentration than about 9.9 g/L, or a greater concentration than about 10.0 g/L), when the pore type is a drilled pore and the pore size is between about 160 μm and about 190 μm (e.g., between about 160 μm and about 185 μm, between about 160 μm and about 180 μm, between about 160 μm and about 175 μm, between about 160 μm and about 170 μm, between about 160 μm and about 165 μm, between about 165 μm and about 190 μm, between about 165 μm and about 185 μm, between about 165 μm and about 180 μm, between about 165 μm and about 175 μm, between about 165 μm and about 170 μm, between about 170 μm and about 190 μm, between about 170 μm and about 185 μm, between about 170 μm and about 180 μm, between about 170 μm and about 175 μm, between about 175 μm and about 190 μm, between about 175 μm and about 185 μm, between about 175 μm and about 180 μm, between about 180 μm and about 190 μm, between about 180 μm and about 185 μm, or between about 185 μm and about 190 μm).

In some embodiments, the methods include selecting based on pore type and pore size poloxamer-188 at a concentration of between about 1.8 g/L and about 3.3 g/L (e.g., between about 1.8 g/L and about 3.2 g/L, between about 1.8 g/L and about 3.1 g/L, between about 1.8 g/L and about 3.0 g/L, between about 1.8 g/L and about 2.9 g/L, between about 1.8 g/L and about 2.8 g/L, between about 1.8 g/L and about 2.7 g/L, between about 1.8 g/L and about 2.6 g/L, between about 1.8 g/L and about 2.5 g/L, between about 1.8 g/L and about 2.4 g/L, between about 1.8 g/L and about 2.3 g/L, between about 1.8 g/L and about 2.2 g/L, between about 1.8 g/L and about 2.1 g/L, between about 1.8 g/L and about 2.0 g/L, between about 1.9 g/L and about 3.3 g/L, between about 1.9 g/L and about 3.2 g/L, between about 1.9 g/L and about 3.1 g/L, between about 1.9 g/L and about 3.0 g/L, between about 1.9 g/L and about 2.9 g/L, between about 1.9 g/L and about 2.8 g/L, between about 1.9 g/L and about 2.7 g/L, between about 1.9 g/L and about 2.6 g/L, between about 1.9 g/L and about 2.5 g/L, between about 1.9 g/L and about 2.4 g/L, between about 1.9 g/L and about 2.3 g/L, between about 1.9 g/L and about 2.2 g/L, between about 1.9 g/L and about 2.1 g/L, between about 2.0 g/L and about 3.3 g/L, between about 2.0 g/L and about 3.2 g/L, between about 2.0 g/L and about 3.1 g/L, between about 2.0 g/L and about 3.0 g/L, between about 2.0 g/L and about 2.9 g/L, between about 2.0 g/L and about 2.8 g/L, between about 2.0 g/L and about 2.7 g/L, between about 2.0 g/L and about 2.6 g/L, between about 2.0 g/L and about 2.5 g/L, between about 2.0 g/L and about 2.4 g/L, between about 2.0 g/L and about 2.3 g/L, between about 2.0 g/L and about 2.2 g/L, between about 2.1 g/L and about 3.3 g/L, between about 2.1 g/L and about 3.2 g/L, between about 2.1 g/L and about 3.1 g/L, between about 2.1 g/L and about 3.0 g/L, between about 2.1 g/L and about 2.9 g/L, between about 2.1 g/L and about 2.8 g/L, between about 2.1 g/L and about 2.7 g/L, between about 2.1 g/L and about 2.6 g/L, between about 2.1 g/L and about 2.5 g/L, between about 2.1 g/L and about 2.4 g/L, between about 2.1 g/L and about 2.3 g/L, between about 2.2 g/L and about 3.3 g/L, between about 2.2 g/L and about 3.2 g/L, between about 2.2 g/L and about 3.1 g/L, between about 2.2 g/L and about 3.0 g/L, between about 2.2 g/L and about 2.9 g/L, between about 2.2 g/L and about 2.8 g/L, between about 2.2 g/L and about 2.7 g/L, between about 2.2 g/L and about 2.6 g/L, between about 2.2 g/L and about 2.5 g/L, between about 2.2 g/L and about 2.4 g/L, between about 2.3 g/L and about 3.3 g/L, between about 2.3 g/L and about 3.2 g/L, between about 2.3 g/L and about 3.1 g/L, between about 2.3 g/L and about 3.0 g/L, between about 2.3 g/L and about 2.9 g/L, between about 2.3 g/L and about 2.8 g/L, between about 2.3 g/L and about 2.7 g/L, between about 2.3 g/L and about 2.6 g/L, between about 2.3 g/L and about 2.5 g/L, between about 2.4 g/L and about 3.3 g/L, between about 2.4 g/L and about 3.2 g/L, between about 2.4 g/L and about 3.1 g/L, between about 2.4 g/L and about 3.0 g/L, between about 2.4 g/L and about 2.9 g/L, between about 2.4 g/L and about 2.8 g/L, between about 2.4 g/L and about 2.7 g/L, between about 2.4 g/L and about 2.6 g/L, between about 2.5 g/L and about 3.3 g/L, between about 2.5 g/L and about 3.2 g/L, between about 2.5 g/L and about 3.1 g/L, between about 2.5 g/L and about 3.0 g/L, between about 2.5 g/L and about 2.9 g/L, between about 2.5 g/L and about 2.8 g/L, between about 2.5 g/L and about 2.7 g/L, between about 2.6 g/L and about 3.3 g/L, between about 2.6 g/L and about 3.2 g/L, between about 2.6 g/L and about 3.1 g/L, between about 2.6 g/L and about 3.0 g/L, between about 2.6 g/L and about 2.9 g/L, between about 2.6 g/L and about 2.8 g/L, between about 2.7 g/L and about 3.3 g/L, between about 2.7 g/L and about 3.2 g/L, between about 2.7 g/L and about 3.1 g/L, between about 2.7 g/L and about 3.0 g/L, between about 2.7 g/L and about 2.9 g/L, between about 2.8 g/L and about 3.3 g/L, between about 2.8 g/L and about 3.2 g/L, between about 2.8 g/L and about 3.1 g/L, between about 2.8 g/L and about 3.0 g/L, between about 2.9 g/L and about 3.3 g/L, between about 2.9 g/L and about 3.2 g/L, between about 2.9 g/L and about 3.1 g/L, between about 3.0 g/L and about 3.3 g/L, between about 3.0 g/L and about 3.2 g/L, or between about 3.1 g/L and about 3.3 g/L), when the pore type is a sintered pore and the pore size is greater than 150 μm (e.g., greater than 155 μm, greater than 160 μm, greater than 165 μm, greater than 170 μm, greater than 175 μm, greater than about 180 μm, greater than 185 μm, greater than about 190 μm, greater than about 195 μm, greater than about 200 μm, greater than about 205 μm, greater than about 210 μm, greater than about 215 μm, greater than about 220 μm, greater than about 225 μm, greater than about 230 μm, greater than about 235 μm, greater than about 240 μm, greater than about 245 μm, greater than about 250 μm, greater than about 255 μm, greater than about 260 μm, greater than about 265 μm, greater than about 270 μm, greater than about 275 μm, greater than about 280 μm, greater than about 290 μm, greater than about 300 μm, greater than about 350 μm, greater than about 400 μm, greater than about 450 μm, or greater than about 500 μm).

The methods can include, e.g., selecting based on pore type and pore size poloxamer-188 at a concentration of between about 3.3 g/L and about 4.3 g/L (e.g., between about 3.3 g/L and about 4.2 g/L, between about 3.3 g/L and about 4.1 g/L, between about 3.3 g/L and about 4.0 g/L, between about 3.3 g/L and about 3.9 g/L, between about 3.3 g/L and about 3.8 g/L, between about 3.3 g/L and about 3.7 g/L, between about 3.3 g/L and about 3.6 g/L, between about 3.3 g/L and about 3.5 g/L, between about 3.4 g/L and about 4.3 g/L, between about 3.4 g/L and about 4.2 g/L, between about 3.4 g/L and about 4.1 g/L, between about 3.4 g/L and about 4.0 g/L, between about 3.4 g/L and about 3.9 g/L, between about 3.4 g/L and about 3.8 g/L, between about 3.4 g/L and about 3.7 g/L, between about 3.4 g/L and about 3.6 g/L, between about 3.5 g/L and about 4.3 g/L, between about 3.5 g/L and about 4.2 g/L, between about 3.5 g/L and about 4.1 g/L, between about 3.5 g/L and about 4.0 g/L, between about 3.5 g/L and about 3.9 g/L, between about 3.5 g/L and about 3.8 g/L, between about 3.5 g/L and about 3.7 g/L, between about 3.6 g/L and about 4.3 g/L, between about 3.6 g/L and about 4.2 g/L, between about 3.6 g/L and about 4.1 g/L, between about 3.6 g/L and about 4.0 g/L, between about 3.6 g/L and about 3.9 g/L, between about 3.6 g/L and about 3.8 g/L, between about 3.7 g/L and about 4.3 g/L, between about 3.7 g/L and about 4.2 g/L, between about 3.7 g/L and about 4.1 g/L, between about 3.7 g/L and about 4.0 g/L, between about 3.7 g/L and about 3.9 g/L, between about 3.8 g/L and about 4.3 g/L, between about 3.8 g/L and about 4.2 g/L, between about 3.8 g/L and about 4.1 g/L, between about 3.8 g/L and about 4.0 g/L, between about 3.9 g/L and about 4.3 g/L, between about 3.9 g/L and about 4.2 g/L, between about 3.9 g/L and about 4.1 g/L, between about 4.0 g/L and about 4.3 g/L, between about 4.0 g/L and about 4.2 g/L, or between about 4.1 g/L and about 4.3 g/L), when the pore type is a sintered pore and the pore size is between about 80 μm and about 150 μm (e.g., between about 80 μm and about 145 μm, between about 80 μm and about 140 μm, between about 80 μm and about 135 μm, between about 80 μm and about 130 μm, between about 80 μm and about 125 μm, between about 80 μm and about 120 μm, between about 80 μm and about 115 μm, between about 80 μm and about 110 μm, between about 80 μm and about 105 μm, between about 80 μm and about 100 μm, between about 80 μm and about 95 μm, between about 80 μm and about 90 μm, between about 80 μm and about 85 μm, between about 85 μm and about 150 μm, between about 85 μm and about 145 μm, between about 85 μm and about 140 μm, between about 85 μm and about 135 μm, between about 85 μm and about 130 μm, between about 85 μm and about 125 μm, between about 85 μm and about 120 μm, between about 85 μm and about 115 μm, between about 85 μm and about 110 μm, between about 85 μm and about 105 μm, between about 85 μm and about 100 μm, between about 85 μm and about 95 μm, between about 85 μm and about 90 μm, between about 90 μm and about 150 μm, between about 90 μm and about 145 μm, between about 90 μm and about 140 μm, between about 90 μm and about 135 μm, between about 90 μm and about 130 μm, between about 90 μm and about 125 μm, between about 90 μm and about 120 μm, between about 90 μm and about 115 μm, between about 90 μm and about 110 μm, between about 90 μm and about 105 μm, between about 90 μm and about 100 μm, between about 90 μm and about 95 μm, between about 95 μm and about 150 μm, between about 95 μm and about 145 μm, between about 95 μm and about 140 μm, between about 95 µm and about 135 µm, between about 95 µm and about 130 µm, between about 95 µm and about 125 µm, between about 95 µm and about 120 µm, between about 95 µm and about 115 µm, between about 95 µm and about 110 µm, between about 95 µm and about 105 µm, between about 95 µm and about 100 µm, between about 100 µm and about 150 µm, between about 100 µm and about 145 µm, between about 100 µm and about 140 µm, between about 100 µm and about 135 µm, between about 100 µm and about 130 µm, between about 100 µm and about 125 µm, between about 100 µm and about 120 µm, between about 100 µm and about 115 µm, between about 100 µm and about 110 µm, between about 100 µm and about 105 µm, between about 105 µm and about 150 µm, between about 105 µm and about 145 µm, between about 105 µm and about 140 µm, between about 105 µm and about 135 µm, between about 105 µm and about 130 µm, between about 105 µm and about 125 µm, between about 105 µm and about 120 µm, between about 105 µm and about 115 µm, between about 105 µm and about 110 µm, between about 110 µm and about 150 µm, between about 110 µm and about 145 µm, between about 110 µm and about 140 µm, between about 110 µm and about 135 µm, between about 110 µm and about 130 µm, between about 110 µm and about 125 µm, between about 110 µm and about 120 µm, between about 110 µm and about 115 µm, between about 115 µm and about 150 µm, between about 115 µm and about 145 µm, between about 115 µm and about 140 µm, between about 115 µm and about 135 µm, between about 115 µm and about 130 µm, between about 115 nm and about 125 nm, between about 115 nm and about 120 nm, between about 120 nm and about 150 nm, between about 120 nm and about 145 nm, between about 120 nm and about 140 µm, between about 120 nm and about 135 nm, between about 120 nm and about 130 µm, between about 120 nm and about 125 nm, between about 125 nm and about 150 µm, between about 125 nm and about 145 nm, between about 125 nm and about 140 nm, between about 125 nm and about 135 nm, between about 125 nm and about 130 µm, between about 130 nm and about 150 nm, between about 130 nm and about 145 µm, between about 130 nm and about 140 nm, between about 130 nm and about 135 µm, between about 135 nm and about 150 nm, between about 135 nm and about 145 µm, between about 135 nm and about 140 nm, between about 140 nm and about 150 µm, between about 140 nm and about 145 nm, or between about 145 nm and about 150 nm).

The methods can include, e.g., selecting based on pore type and pore size poloxamer-188 at a concentration of about 4.5 g/L or at a greater concentration than about 4.5 g/L (e.g., at a concentration of about 4.6 g/L or at a concentration of greater than 4.6 g/L, at a concentration of about 4.7 g/L or at a concentration of greater than 4.7 g/L, at a concentration of about 4.8 g/L or at a concentration of greater than 4.8 g/L, at a concentration of about 4.9 g/L or at a concentration of greater than 4.9 g/L, at a concentration of about 5.0 g/L or at a concentration of greater than 5.0 g/L, at a concentration of about 5.1 g/L or at a concentration of greater than 5.1 g/L, at a concentration of about 5.2 g/L or at a concentration of greater than 5.2 g/L, at a concentration of about 5.3 g/L or at a concentration of greater than 5.3 g/L, at a concentration of about 5.4 g/L or at a concentration of greater than 5.4 g/L, at a concentration of about 5.5 g/L or at a concentration of greater than 5.5 g/L, at a concentration of about 5.6 g/L or at a concentration of greater than 5.6 g/L, at a concentration of about 5.7 g/L or at a concentration of greater than 5.7 g/L, at a concentration of about 5.8 g/L or at a concentration of greater than 5.8 g/L, at a concentration of about 6.0 g/L or at a concentration of greater than 6.0 g/L, at a concentration of about 6.1 g/L or at a concentration of greater than 6.1 g/L, at a concentration of about 6.2 g/L or at a concentration of greater than 6.2 g/L, at a concentration of about 6.3 g/L or at a concentration of greater than 6.3 g/L, at a concentration of about 6.4 g/L or at a concentration of greater than 6.4 g/L, at a concentration of about 6.5 g/L or at a concentration of greater than 6.5 g/L, at a concentration of about 6.6 g/L or at a concentration of greater than 6.6 g/L, at a concentration of about 6.7 g/L or at a concentration of greater than 6.7 g/L, at a concentration of about 6.8 g/L or at a concentration of greater than 6.8 g/L, at a concentration of about 6.9 g/L or at a concentration of greater than 6.9 g/L, at a concentration of about 7.0 g/L or at a concentration of greater than 7.0 g/L, at a concentration of about 7.1 g/L or at a concentration of greater than 7.1 g/L, at a concentration of about 7.2 g/L or at a concentration of greater than 7.2 g/L, at a concentration of about 7.3 g/L or at a concentration of greater than 7.3 g/L, at a concentration of about 7.4 g/L or at a concentration of greater than 7.4 g/L, at a concentration of about 7.5 g/L or at a concentration of greater than 7.5 g/L, at a concentration of about 7.6 g/L or at a concentration of greater than 7.6 g/L, at a concentration of about 7.7 g/L or at a concentration of greater than 7.7 g/L, at a concentration of about 7.8 g/L or at a concentration of greater than 7.8 g/L, at a concentration of about 7.9 g/L or at a concentration of greater than 7.9 g/L, at a concentration of about 8.0 g/L or at a concentration of greater than 8.0 g/L, at a concentration of about 8.1 g/L or at a concentration of greater than 8.1 g/L, at a concentration of about 8.2 g/L or at a concentration of greater than 8.2 g/L, at a concentration of about 8.3 g/L or at a concentration of greater than 8.3 g/L, at a concentration of about 8.4 g/L or at a concentration of greater than 8.4 g/L, at a concentration of about 8.5 g/L or at a concentration of greater than 8.5 g/L, at a concentration of about 8.6 g/L or at a concentration of greater than 8.6 g/L, at a concentration of about 8.7 g/L or at a concentration of greater than 8.7 g/L, at a concentration of about 8.8 g/L or at a concentration of greater than 8.8 g/L, at a concentration of about 8.9 g/L or at a concentration of greater than 8.9 g/L, at a concentration of about 9.0 g/L or at a concentration of greater than 9.0 g/L, at a concentration of about 9.1 g/L or at a concentration of greater than 9.1 g/L, at a concentration of about 9.2 g/L or at a concentration of greater than 9.2 g/L, at a concentration of about 9.3 g/L or at a concentration of greater than 9.3 g/L, at a concentration of about 9.4 g/L or at a concentration of greater than 9.4 g/L, at a concentration of about 9.5 g/L or at a concentration of greater than 9.5 g/L, at a concentration of about 9.6 g/L or at a concentration of greater than 9.6 g/L, at a concentration of about 9.7 g/L or at a concentration of greater than 9.7 g/L, at a concentration of about 9.8 g/L or at a concentration of greater than 9.8 g/L, at a concentration of about 9.9 g/L or at a concentration of greater than 9.9 g/L, or at a concentration of about 10.0 g/L or at a concentration of greater than 10.0 g/L), when the pore type is a sintered pore and the pore size is between about 1 µm and about 80 µm (e.g., between about 1 µm and about 50 µm, between about 1 µm and about 25 µm, between about 1 µm and about 10 µm, between about 1 µm and about 5 µm, between about 5 µm and about 80 µm, between about 5 µm and about 50 µm, between about 5 µm and about 25 µm, between about 5 µm and about 10 µm, between about 10 µm and about 80 µm, between about 10 µm and about 50 µm, between about 10 µm and about 25 µm, between about 25 µm and about 80 µm, between about 25 µm and about 50 µm, or between about 50 µm and about 80 µm).

When the culturing is perfusion culturing, the second liquid medium can include the selected poloxamer-188 concentration.

Increasing Poloxamer-188 Concentration Based on Viable Cell Density

Some embodiments of any of the methods described herein include increasing the poloxamer-188 concentration in the medium over time based on the viable cell density in the medium. For example, any of the methods described herein can include increasing the poloxamer-188 concentration in the medium to greater than 1.8 g/L (e.g., between about 1.8 g/L and about 3.0 g/L, between about 1.8 g/L and about 2.9 g/L, between about 1.8 g/L and about 2.8 g/L, between about 1.8 g/L and about 2.7 g/L, between about 1.8 g/L and about 2.5 g/L, between about 1.8 g/L and about 2.4 g/L, between about 1.8 g/L and about 2.3 g/L, between about 1.8 g/L and about 2.2 g/L, between about 1.8 g/L and about 2.1 g/L, between about 1.8 g/L and about 2.0 g/L, between about 1.9 g/L and about 3.0 g/L, between about 1.9 g/L and about 2.9 g/L, between about 1.9 g/L and about 2.8 g/L, between about 1.9 g/L and about 2.7 g/L, between about 1.9 g/L and about 2.6 g/L, between about 1.9 g/L and about 2.5 g/L, between about 1.9 g/L and about 2.4 g/L, between about 1.9 g/L and about 2.3 g/L, between about 1.9 g/L and about 2.2 g/L, between about 1.9 g/L and about 2.1 g/L, between about 2.0 g/L and about 3.0 g/L, between about 2.0 g/L and about 2.9 g/L, between about 2.0 g/L and about 2.8 g/L, between about 2.0 g/L and about 2.7 g/L, between about 2.0 g/L and about 2.6 g/L, between about 2.0 g/L and about 2.5 g/L, between about 2.0 g/L and about 2.4 g/L, between about 2.0 g/L and about 2.3 g/L, between about 2.0 g/L and about 2.2 g/L, between about 2.1 g/L and about 3.0 g/L, between about 2.1 g/L and about 2.9 g/L, between about 2.1 g/L and about 2.8 g/L, between about 2.1 g/L and about 2.7 g/L, between about 2.1 g/L and about 2.6 g/L, between about 2.1 g/L and about 2.5 g/L, between about 2.1 g/L and about 2.4 g/L, between about 2.1 g/L and about 2.3 g/L, between about 2.2 g/L and about 3.0 g/L, between about 2.2 g/L and about 2.9 g/L, between about 2.2 g/L and about 2.8 g/L, between about 2.2 g/L and about 2.7 g/L, between about 2.2 g/L and about 2.6 g/L, between about 2.2 g/L and about 2.5 g/L, between about 2.2 g/L and about 2.4 g/L, between about 2.3 g/L and about 3.0 g/L, between about 2.3 g/L and about 2.9 g/L, between about 2.3 g/L and about 2.8 g/L, between about 2.3 g/L and about 2.7 g/L, between about 2.3 g/L and about 2.6 g/L, between about 2.3 g/L and about 2.5 g/L, between about 2.4 g/L and about 3.0 g/L, between about 2.4 g/L and about 2.9 g/L, between about 2.4 g/L and about 2.8 g/L, between about 2.4 g/L and about 2.7 g/L, between about 2.4 g/L and about 2.6 g/L, between about 2.5 g/L and about 3.0 g/L, between about 2.5 g/L and about 2.9 g/L, between about 2.5 g/L and about 2.8 g/L, between about 2.5 g/L and about 2.7 g/L, between about 2.6 g/L and about 3.0 g/L, between about 2.6 g/L and about 2.9 g/L, between about 2.6 g/L and about 2.8 g/L, between about 2.7 g/L and about 3.0 g/L, between about 2.7 g/L and about 2.9 g/L, or between about 2.8 g/L and about 3.0 g/L) when the viable cell density in the medium is between about $20\times10^6$ cells/mL to about $60\times10^6$ cells/mL (e.g., between about $20\times10^6$ cells/mL and about $58\times10^6$ cells/mL, between about $20\times10^6$ cells/mL to about $56\times10^6$ cells/mL, between about $20\times10^6$ cells/mL and about $54\times10^6$ cells/mL, between about $20\times10^6$ cells/mL and about $52\times10^6$ cells/mL, between about $20\times10^6$ cells/mL and about $50\times10^6$ cells/mL, between about $20\times10^6$ cells/mL and about $48\times10^6$ cells/mL, between about $20\times10^6$ cells/mL and about $46\times10^6$ cells/mL, between about $20\times10^6$ cells/mL and about $44\times10^6$ cells/mL, between about $20\times10^6$ cells/mL and about $42\times10^6$ cells/mL, between about $20\times10^6$ cells/mL to about $40\times10^6$ cells/mL, between about $20\times10^6$ cells/mL and about $38\times10^6$ cells/mL, between about $20\times10^6$ cells/mL and about $36\times10^6$ cells/mL, between about $20\times10^6$ cells/mL and about $34\times10^6$ cells/mL, between about $20\times10^6$ cells/mL and about $32\times10^6$ cells/mL, between about $20\times10^6$ cells/mL and about $30\times10^6$ cells/mL, between about $20\times10^6$ cells/mL to about $28\times10^6$ cells/mL, between about $20\times10^6$ cells/mL and about $26\times10^6$ cells/mL, between about $20\times10^6$ cells/mL and about $24\times10^6$ cells/mL, between about $20\times10^6$ cells/mL and about $22\times10^6$ cells/mL, between about $22\times10^6$ cells/mL and about $60\times10^6$ cells/mL, between about $22\times10^6$ cells/mL and about $58\times10^6$ cells/mL, between about $22\times10^6$ cells/mL to about $56\times10^6$ cells/mL, between about $22\times10^6$ cells/mL and about $54\times10^6$ cells/mL, between about $22\times10^6$ cells/mL and about $52\times10^6$ cells/mL, between about $22\times10^6$ cells/mL and about $50\times10^6$ cells/mL, between about $22\times10^6$ cells/mL and about $48\times10^6$ cells/mL, between about $22\times10^6$ cells/mL and about $46\times10^6$ cells/mL, between about $22\times10^6$ cells/mL and about $44\times10^6$ cells/mL, between about $22\times10^6$ cells/mL and about $42\times10^6$ cells/mL, between about $22\times10^6$ cells/mL to about $40\times10^6$ cells/mL, between about $22\times10^6$ cells/mL and about $38\times10^6$ cells/mL, between about $22\times10^6$ cells/mL and about $36\times10^6$ cells/mL, between about $22\times10^6$ cells/mL and about $34\times10^6$ cells/mL, between about $22\times10^6$ cells/mL and about $32\times10^6$ cells/mL, between about $22\times10^6$ cells/mL and about $30\times10^6$ cells/mL, between about $22\times10^6$ cells/mL to about $28\times10^6$ cells/mL, between about $22\times10^6$ cells/mL and about $26\times10^6$ cells/mL, between about $22\times10^6$ cells/mL and about $24\times10^6$ cells/mL, between about $24\times10^6$ cells/mL and about $60\times10^6$ cells/mL, between about $24\times10^6$ cells/mL and about $58\times10^6$ cells/mL, between about $24\times10^6$ cells/mL to about $56\times10^6$ cells/mL, between about $24\times10^6$ cells/mL and about $54\times10^6$ cells/mL, between about $24\times10^6$ cells/mL and about $52\times10^6$ cells/mL, between about $24\times10^6$ cells/mL and about $50\times10^6$ cells/mL, between about $24\times10^6$ cells/mL and about $48\times10^6$ cells/mL, between about $24\times10^6$ cells/mL and about $46\times10^6$ cells/mL, between about $24\times10^6$ cells/mL and about $44\times10^6$ cells/mL, between about $24\times10^6$ cells/mL and about $42\times10^6$ cells/mL, between about $24\times10^6$ cells/mL to about $40\times10^6$ cells/mL, between about $24\times10^6$ cells/mL and about $38\times10^6$ cells/mL, between about $24\times10^6$ cells/mL and about $36\times10^6$ cells/mL, between about $24\times10^6$ cells/mL and about $34\times10^6$ cells/mL, between about $24\times10^6$ cells/mL and about $32\times10^6$ cells/mL, between about $24\times10^6$ cells/mL and about $30\times10^6$ cells/mL, between about $24\times10^6$ cells/mL to about $28\times10^6$ cells/mL, between about $24\times10^6$ cells/mL and about $26\times10^6$ cells/mL, between about $26\times10^6$ cells/mL and about $60\times10^6$ cells/mL, between about $26\times10^6$ cells/mL and about $58\times10^6$ cells/mL, between about $26\times10^6$ cells/mL to about $56\times10^6$ cells/mL, between about $26\times10^6$ cells/mL and about $54\times10^6$ cells/mL, between about $26\times10^6$ cells/mL and about $52\times10^6$ cells/mL, between about $26\times10^6$ cells/mL and about $50\times10^6$ cells/mL, between about $26\times10^6$ cells/mL and about $48\times10^6$ cells/mL, between about $26\times10^6$ cells/mL and about $46\times10^6$ cells/mL, between about $26\times10^6$ cells/mL and about $44\times10^6$ cells/mL, between about $26\times10^6$ cells/mL and about $42\times10^6$ cells/mL, between about $26\times10^6$ cells/mL to about $40\times10^6$ cells/mL, between about $26\times10^6$ cells/mL and about $38\times10^6$ cells/mL, between about $26\times10^6$ cells/mL and about $36\times10^6$ cells/mL, between about $26\times10^6$ cells/mL and about $34\times10^6$ cells/mL, between about $26\times10^6$ cells/mL and about $32\times10^6$ cells/mL, between about $26\times10^6$ cells/mL and about $30\times10^6$ cells/mL, between about $26\times10^6$ cells/mL to about $28\times10^6$ cells/mL, between about $28\times10^6$ cells/mL and about $60\times10^6$ cells/mL, between about $28\times10^6$ cells/mL and about $58\times10^6$ cells/mL, between about $28\times10^6$ cells/mL to about $56\times10^{6}$ cells/mL, between about $28\times10^{6}$ cells/mL and about $54\times10^{6}$ cells/mL, between about $28\times10^{6}$ cells/mL and about $52\times10^{6}$ cells/mL, between about $28\times10^{6}$ cells/mL and about $50\times10^{6}$ cells/mL, between about $28\times10^{6}$ cells/mL and about $48\times10^{6}$ cells/mL, between about $28\times10^{6}$ cells/mL and about $46\times10^{6}$ cells/mL, between about $28\times10^{6}$ cells/mL and about $44\times10^{6}$ cells/mL, between about $28\times10^{6}$ cells/mL and about $42\times10^{6}$ cells/mL, between about $28\times10^{6}$ cells/mL to about $40\times10^{6}$ cells/mL, between about $28\times10^{6}$ cells/mL and about $38\times10^{6}$ cells/mL, between about $28\times10^{6}$ cells/mL and about $36\times10^{6}$ cells/mL, between about $28\times10^{6}$ cells/mL and about $34\times10^{6}$ cells/mL, between about $28\times10^{6}$ cells/mL and about $32\times10^{6}$ cells/mL, between about $28\times10^{6}$ cells/mL and about $30\times10^{6}$ cells/mL, between about $30\times10^{6}$ cells/mL and about $60\times10^{6}$ cells/mL, between about $30\times10^{6}$ cells/mL and about $58\times10^{6}$ cells/mL, between about $30\times10^{6}$ cells/mL to about $56\times10^{6}$ cells/mL, between about $30\times10^{6}$ cells/mL and about $54\times10^{6}$ cells/mL, between about $30\times10^{6}$ cells/mL and about $52\times10^{6}$ cells/mL, between about $30\times10^{6}$ cells/mL and about $50\times10^{6}$ cells/mL, between about $30\times10^{6}$ cells/mL and about $48\times10^{6}$ cells/mL, between about $30\times10^{6}$ cells/mL and about $46\times10^{6}$ cells/mL, between about $30\times10^{6}$ cells/mL and about $44\times10^{6}$ cells/mL, between about $30\times10^{6}$ cells/mL and about $42\times10^{6}$ cells/mL, between about $30\times10^{6}$ cells/mL to about $40\times10^{6}$ cells/mL, between about $30\times10^{6}$ cells/mL and about $38\times10^{6}$ cells/mL, between about $30\times10^{6}$ cells/mL and about $36\times10^{6}$ cells/mL, between about $30\times10^{6}$ cells/mL and about $34\times10^{6}$ cells/mL, between about $30\times10^{6}$ cells/mL and about $32\times10^{6}$ cells/mL, between about $32\times10^{6}$ cells/mL and about $60\times10^{6}$ cells/mL, between about $32\times10^{6}$ cells/mL and about $58\times10^{6}$ cells/mL, between about $32\times10^{6}$ cells/mL to about $56\times10^{6}$ cells/mL, between about $32\times10^{6}$ cells/mL and about $54\times10^{6}$ cells/mL, between about $32\times10^{6}$ cells/mL and about $52\times10^{6}$ cells/mL, between about $32\times10^{6}$ cells/mL and about $50\times10^{6}$ cells/mL, between about $32\times10^{6}$ cells/mL and about $48\times10^{6}$ cells/mL, between about $32\times10^{6}$ cells/mL and about $46\times10^{6}$ cells/mL, between about $32\times10^{6}$ cells/mL and about $44\times10^{6}$ cells/mL, between about $32\times10^{6}$ cells/mL and about $42\times10^{6}$ cells/mL, between about $32\times10^{6}$ cells/mL to about $40\times10^{6}$ cells/mL, between about $32\times10^{6}$ cells/mL and about $38\times10^{6}$ cells/mL, between about $32\times10^{6}$ cells/mL and about $36\times10^{6}$ cells/mL, between about $32\times10^{6}$ cells/mL and about $34\times10^{6}$ cells/mL, between about $34\times10^{6}$ cells/mL and about $60\times10^{6}$ cells/mL, between about $34\times10^{6}$ cells/mL and about $58\times10^{6}$ cells/mL, between about $34\times10^{6}$ cells/mL to about $56\times10^{6}$ cells/mL, between about $34\times10^{6}$ cells/mL and about $54\times10^{6}$ cells/mL, between about $34\times10^{6}$ cells/mL and about $52\times10^{6}$ cells/mL, between about $34\times10^{6}$ cells/mL and about $50\times10^{6}$ cells/mL, between about $34\times10^{6}$ cells/mL and about $48\times10^{6}$ cells/mL, between about $34\times10^{6}$ cells/mL and about $46\times10^{6}$ cells/mL, between about $34\times10^{6}$ cells/mL and about $44\times10^{6}$ cells/mL, between about $34\times10^{6}$ cells/mL and about $42\times10^{6}$ cells/mL, between about $34\times10^{6}$ cells/mL to about $40\times10^{6}$ cells/mL, between about $34\times10^{6}$ cells/mL and about $38\times10^{6}$ cells/mL, between about $34\times10^{6}$ cells/mL and about $36\times10^{6}$ cells/mL, between about $36\times10^{6}$ cells/mL and about $60\times10^{6}$ cells/mL, between about $36\times10^{6}$ cells/mL and about $58\times10^{6}$ cells/mL, between about $36\times10^{6}$ cells/mL to about $56\times10^{6}$ cells/mL, between about $36\times10^{6}$ cells/mL and about $54\times10^{6}$ cells/mL, between about $36\times10^{6}$ cells/mL and about $52\times10^{6}$ cells/mL, between about $36\times10^{6}$ cells/mL and about $50\times10^{6}$ cells/mL, between about $36\times10^{6}$ cells/mL and about $48\times10^{6}$ cells/mL, between about $36\times10^{6}$ cells/mL and about $46\times10^{6}$ cells/mL, between about $36\times10^{6}$ cells/mL and about $44\times10^{6}$ cells/mL, between about $36\times10^{6}$ cells/mL and about $42\times10^{6}$ cells/mL, between about $36\times10^{6}$ cells/mL to about $40\times10^{6}$ cells/mL, between about $36\times10^{6}$ cells/mL and about $38\times10^{6}$ cells/mL, between about $38\times10^{6}$ cells/mL and about $60\times10^{6}$ cells/mL, between about $38\times10^{6}$ cells/mL and about $58\times10^{6}$ cells/mL, between about $38\times10^{6}$ cells/mL to about $56\times10^{6}$ cells/mL, between about $38\times10^{6}$ cells/mL and about $54\times10^{6}$ cells/mL, between about $38\times10^{6}$ cells/mL and about $52\times10^{6}$ cells/mL, between about $38\times10^{6}$ cells/mL and about $50\times10^{6}$ cells/mL, between about $38\times10^{6}$ cells/mL and about $48\times10^{6}$ cells/mL, between about $38\times10^{6}$ cells/mL and about $46\times10^{6}$ cells/mL, between about $38\times10^{6}$ cells/mL and about $44\times10^{6}$ cells/mL, between about $38\times10^{6}$ cells/mL and about $42\times10^{6}$ cells/mL, between about $38\times10^{6}$ cells/mL to about $40\times10^{6}$ cells/mL, between about $40\times10^{6}$ cells/mL and about $60\times10^{6}$ cells/mL, between about $40\times10^{6}$ cells/mL and about $58\times10^{6}$ cells/mL, between about $40\times10^{6}$ cells/mL to about $56\times10^{6}$ cells/mL, between about $40\times10^{6}$ cells/mL and about $54\times10^{6}$ cells/mL, between about $40\times10^{6}$ cells/mL and about $52\times10^{6}$ cells/mL, between about $40\times10^{6}$ cells/mL and about $50\times10^{6}$ cells/mL, between about $40\times10^{6}$ cells/mL and about $48\times10^{6}$ cells/mL, between about $40\times10^{6}$ cells/mL and about $46\times10^{6}$ cells/mL, between about $40\times10^{6}$ cells/mL and about $44\times10^{6}$ cells/mL, between about $40\times10^{6}$ cells/mL and about $42\times10^{6}$ cells/mL, between about $42\times10^{6}$ cells/mL and about $60\times10^{6}$ cells/mL, between about $42\times10^{6}$ cells/mL and about $58\times10^{6}$ cells/mL, between about $42\times10^{6}$ cells/mL to about $56\times10^{6}$ cells/mL, between about $42\times10^{6}$ cells/mL and about $54\times10^{6}$ cells/mL, between about $42\times10^{6}$ cells/mL and about $52\times10^{6}$ cells/mL, between about $42\times10^{6}$ cells/mL and about $50\times10^{6}$ cells/mL, between about $42\times10^{6}$ cells/mL and about $48\times10^{6}$ cells/mL, between about $42\times10^{6}$ cells/mL and about $46\times10^{6}$ cells/mL, between about $42\times10^{6}$ cells/mL and about $44\times10^{6}$ cells/mL, between about $44\times10^{6}$ cells/mL and about $60\times10^{6}$ cells/mL, between about $44\times10^{6}$ cells/mL and about $58\times10^{6}$ cells/mL, between about $44\times10^{6}$ cells/mL to about $56\times10^{6}$ cells/mL, between about $44\times10^{6}$ cells/mL and about $54\times10^{6}$ cells/mL, between about $44\times10^{6}$ cells/mL and about $52\times10^{6}$ cells/mL, between about $44\times10^{6}$ cells/mL and about $50\times10^{6}$ cells/mL, between about $44\times10^{6}$ cells/mL and about $48\times10^{6}$ cells/mL, between about $44\times10^{6}$ cells/mL and about $46\times10^{6}$ cells/mL, between about $46\times10^{6}$ cells/mL and about $60\times10^{6}$ cells/mL, between about $46\times10^{6}$ cells/mL and about $58\times10^{6}$ cells/mL, between about $46\times10^{6}$ cells/mL to about $56\times10^{6}$ cells/mL, between about $46\times10^{6}$ cells/mL and about $54\times10^{6}$ cells/mL, between about $46\times10^{6}$ cells/mL and about $52\times10^{6}$ cells/mL, between about $46\times10^{6}$ cells/mL and about $50\times10^{6}$ cells/mL, between about $46\times10^{6}$ cells/mL and about $48\times10^{6}$ cells/mL, between about $48\times10^{6}$ cells/mL and about $60\times10^{6}$ cells/mL, between about $48\times10^{6}$ cells/mL and about $58\times10^{6}$ cells/mL, between about $48\times10^{6}$ cells/mL to about $56\times10^{6}$ cells/mL, between about $48\times10^{6}$ cells/mL and about $54\times10^{6}$ cells/mL, between about $48\times10^{6}$ cells/mL and about $52\times10^{6}$ cells/mL, between about $48\times10^{6}$ cells/mL and about $50\times10^{6}$ cells/mL, between about $50\times10^{6}$ cells/mL and about $60\times10^{6}$ cells/mL, between about $50\times10^{6}$ cells/mL and about $58\times10^{6}$ cells/mL, between about $50\times10^{6}$ cells/mL to about $56\times10^{6}$ cells/mL, between about $50\times10^{6}$ cells/mL and about $54\times10^{6}$ cells/mL, between about $50\times10^{6}$ cells/mL and about $52\times10^{6}$ cells/mL, between about $52\times10^{6}$ cells/mL and about $60\times10^{6}$ cells/mL, between about $52\times10^{6}$ cells/mL and about $58\times10^{6}$ cells/mL, between about $52\times10^{6}$ cells/mL to about $56\times10^{6}$ cells/mL, between about $52\times10^{6}$ cells/mL and about $54\times10^{6}$ cells/mL, between about $54\times10^{6}$ cells/mL and about $60\times10^{6}$ cells/mL, between about $54\times10^{6}$ cells/mL and about $58\times10^{6}$ cells/mL, between about $54\times10^{6}$ cells/mL to about $56\times10^{6}$ cells/mL, between about $56\times10^{6}$ cells/mL and about $60\times10^{6}$ cells/mL, between about $56\times10^{6}$ cells/mL and about $58\times10^{6}$ cells/mL, or between about $58\times10^{6}$ cells/mL and about $60\times10^{6}$ cells/mL).

Any of the methods described herein can include increasing the poloxamer-188 concentration in the medium to between about 3.0 g/L and about 6.0 g/L (e.g., between about 3.0 g/L and about 5.9 g/L, between about 3.0 g/L and about 5.8 g/L, between about 3.0 g/L and about 5.7 g/L, between about 3.0 g/L and about 5.6 g/L, between about 3.0 g/L and about 5.5 g/L, between about 3.0 g/L and about 5.4 g/L, between about 3.0 g/L and about 5.3 g/L, between about 3.0 g/L and about 5.2 g/L, between about 3.0 g/L and about 5.1 g/L, between about 3.0 g/L and about 5.0 g/L, between about 3.0 g/L and about 4.9 g/L, between about 3.0 g/L and about 4.8 g/L, between about 3.0 g/L and about 4.7 g/L, between about 3.0 g/L and about 4.6 g/L, between about 3.0 g/L and about 4.5 g/L, between about 3.0 g/L and about 4.4 g/L, between about 3.0 g/L and about 4.3 g/L, between about 3.0 g/L and about 4.2 g/L, between about 3.0 g/L and about 4.1 g/L, between about 3.0 g/L and about 4.0 g/L, between about 3.0 g/L and about 3.9 g/L, between about 3.0 g/L and about 3.8 g/L, between about 3.0 g/L and about 3.7 g/L, between about 3.0 g/L and about 3.6 g/L, between about 3.0 g/L and about 3.5 g/L, between about 3.0 g/L and about 3.4 g/L, between about 3.0 g/L and about 3.3 g/L, between about 3.0 g/L and about 3.2 g/L, between about 3.1 g/L and about 6.0 g/L, between about 3.1 g/L and about 5.9 g/L, between about 3.1 g/L and about 5.8 g/L, between about 3.1 g/L and about 5.7 g/L, between about 3.1 g/L and about 5.6 g/L, between about 3.1 g/L and about 5.5 g/L, between about 3.1 g/L and about 5.4 g/L, between about 3.1 g/L and about 5.3 g/L, between about 3.1 g/L and about 5.2 g/L, between about 3.1 g/L and about 5.1 g/L, between about 3.1 g/L and about 5.0 g/L, between about 3.1 g/L and about 4.9 g/L, between about 3.1 g/L and about 4.8 g/L, between about 3.1 g/L and about 4.7 g/L, between about 3.1 g/L and about 4.6 g/L, between about 3.1 g/L and about 4.5 g/L, between about 3.1 g/L and about 4.4 g/L, between about 3.1 g/L and about 4.3 g/L, between about 3.1 g/L and about 4.2 g/L, between about 3.1 g/L and about 4.1 g/L, between about 3.1 g/L and about 4.0 g/L, between about 3.1 g/L and about 3.9 g/L, between about 3.1 g/L and about 3.8 g/L, between about 3.1 g/L and about 3.7 g/L, between about 3.1 g/L and about 3.6 g/L, between about 3.1 g/L and about 3.5 g/L, between about 3.1 g/L and about 3.4 g/L, between about 3.1 g/L and about 3.3 g/L, between about 3.2 g/L and about 6.0 g/L, between about 3.2 g/L and about 5.9 g/L, between about 3.2 g/L and about 5.8 g/L, between about 3.2 g/L and about 5.7 g/L, between about 3.2 g/L and about 5.6 g/L, between about 3.2 g/L and about 5.5 g/L, between about 3.2 g/L and about 5.4 g/L, between about 3.2 g/L and about 5.3 g/L, between about 3.2 g/L and about 5.2 g/L, between about 3.2 g/L and about 5.1 g/L, between about 3.2 g/L and about 5.0 g/L, between about 3.2 g/L and about 4.9 g/L, between about 3.2 g/L and about 4.8 g/L, between about 3.2 g/L and about 4.7 g/L, between about 3.2 g/L and about 4.6 g/L, between about 3.2 g/L and about 4.5 g/L, between about 3.2 g/L and about 4.4 g/L, between about 3.2 g/L and about 4.3 g/L, between about 3.2 g/L and about 4.2 g/L, between about 3.2 g/L and about 4.1 g/L, between about 3.2 g/L and about 4.0 g/L, between about 3.2 g/L and about 3.9 g/L, between about 3.2 g/L and about 3.8 g/L, between about 3.2 g/L and about 3.7 g/L, between about 3.2 g/L and about 3.6 g/L, between about 3.2 g/L and about 3.5 g/L, between about 3.2 g/L and about 3.4 g/L, between about 3.3 g/L and about 6.0 g/L, between about 3.3 g/L and about 5.9 g/L, between about 3.3 g/L and about 5.8 g/L, between about 3.3 g/L and about 5.7 g/L, between about 3.3 g/L and about 5.6 g/L, between about 3.3 g/L and about 5.5 g/L, between about 3.3 g/L and about 5.4 g/L, between about 3.3 g/L and about 5.3 g/L, between about 3.3 g/L and about 5.2 g/L, between about 3.3 g/L and about 5.1 g/L, between about 3.3 g/L and about 5.0 g/L, between about 3.3 g/L and about 4.9 g/L, between about 3.3 g/L and about 4.8 g/L, between about 3.3 g/L and about 4.7 g/L, between about 3.3 g/L and about 4.6 g/L, between about 3.3 g/L and about 4.5 g/L, between about 3.3 g/L and about 4.4 g/L, between about 3.3 g/L and about 4.3 g/L, between about 3.3 g/L and about 4.2 g/L, between about 3.3 g/L and about 4.1 g/L, between about 3.3 g/L and about 4.0 g/L, between about 3.3 g/L and about 3.9 g/L, between about 3.3 g/L and about 3.8 g/L, between about 3.3 g/L and about 3.7 g/L, between about 3.3 g/L and about 3.6 g/L, between about 3.3 g/L and about 3.5 g/L, between about 3.4 g/L and about 6.0 g/L, between about 3.4 g/L and about 5.9 g/L, between about 3.4 g/L and about 5.8 g/L, between about 3.4 g/L and about 5.7 g/L, between about 3.4 g/L and about 5.6 g/L, between about 3.4 g/L and about 5.5 g/L, between about 3.4 g/L and about 5.4 g/L, between about 3.4 g/L and about 5.3 g/L, between about 3.4 g/L and about 5.2 g/L, between about 3.4 g/L and about 5.1 g/L, between about 3.4 g/L and about 5.0 g/L, between about 3.4 g/L and about 4.9 g/L, between about 3.4 g/L and about 4.8 g/L, between about 3.4 g/L and about 4.7 g/L, between about 3.4 g/L and about 4.6 g/L, between about 3.4 g/L and about 4.5 g/L, between about 3.4 g/L and about 4.4 g/L, between about 3.4 g/L and about 4.3 g/L, between about 3.4 g/L and about 4.2 g/L, between about 3.4 g/L and about 4.1 g/L, between about 3.4 g/L and about 4.0 g/L, between about 3.4 g/L and about 3.9 g/L, between about 3.4 g/L and about 3.8 g/L, between about 3.4 g/L and about 3.7 g/L, between about 3.4 g/L and about 3.6 g/L, between about 3.5 g/L and about 6.0 g/L, between about 3.5 g/L and about 5.9 g/L, between about 3.5 g/L and about 5.8 g/L, between about 3.5 g/L and about 5.7 g/L, between about 3.5 g/L and about 5.6 g/L, between about 3.5 g/L and about 5.5 g/L, between about 3.5 g/L and about 5.4 g/L, between about 3.5 g/L and about 5.3 g/L, between about 3.5 g/L and about 5.2 g/L, between about 3.5 g/L and about 5.1 g/L, between about 3.5 g/L and about 5.0 g/L, between about 3.5 g/L and about 4.9 g/L, between about 3.5 g/L and about 4.8 g/L, between about 3.5 g/L and about 4.7 g/L, between about 3.5 g/L and about 4.6 g/L, between about 3.5 g/L and about 4.5 g/L, between about 3.5 g/L and about 4.4 g/L, between about 3.5 g/L and about 4.3 g/L, between about 3.5 g/L and about 4.2 g/L, between about 3.5 g/L and about 4.1 g/L, between about 3.5 g/L and about 4.0 g/L, between about 3.5 g/L and about 3.9 g/L, between about 3.5 g/L and about 3.8 g/L, between about 3.5 g/L and about 3.7 g/L, between about 3.6 g/L and about 6.0 g/L, between about 3.6 g/L and about 5.9 g/L, between about 3.6 g/L and about 5.8 g/L, between about 3.6 g/L and about 5.7 g/L, between about 3.6 g/L and about 5.6 g/L, between about 3.6 g/L and about 5.5 g/L, between about 3.6 g/L and about 5.4 g/L, between about 3.6 g/L and about 5.3 g/L, between about 3.6 g/L and about 5.2 g/L, between about 3.6 g/L and about 5.1 g/L, between about 3.6 g/L and about 5.0 g/L, between about 3.6 g/L and about 4.9 g/L, between about 3.6 g/L and about 4.8 g/L, between about 3.6 g/L and about 4.7 g/L, between about 3.6 g/L and about 4.6 g/L, between about 3.6 g/L and about 4.5 g/L, between about 3.6 g/L and about 4.4 g/L, between about 3.6 g/L and about 4.3 g/L, between about 3.6 g/L and about 4.2 g/L, between about 3.6 g/L and about 4.1 g/L, between about 3.6 g/L and about 4.0 g/L, between about 3.6 g/L and about 3.9 g/L, between about 3.6 g/L and about 3.8 g/L, between about 3.7 g/L and about 6.0 g/L, between about 3.7 g/L and about 5.9 g/L, between about 3.7 g/L and about 5.8 g/L, between about 3.7 g/L and about 5.7 g/L, between about 3.7 g/L and about 5.6 g/L, between about 3.7 g/L and about 5.5 g/L, between about 3.7 g/L and about 5.4 g/L, between about 3.7 g/L and about 5.3 g/L, between about 3.7 g/L and about 5.2 g/L, between about 3.7 g/L and about 5.1 g/L, between about 3.7 g/L and about 5.0 g/L, between about 3.7 g/L and about 4.9 g/L, between about 3.7 g/L and about 4.8 g/L, between about 3.7 g/L and about 4.7 g/L, between about 3.7 g/L and about 4.6 g/L, between about 3.7 g/L and about 4.5 g/L, between about 3.7 g/L and about 4.4 g/L, between about 3.7 g/L and about 4.3 g/L, between about 3.7 g/L and about 4.2 g/L, between about 3.7 g/L and about 4.1 g/L, between about 3.7 g/L and about 4.0 g/L, between about 3.7 g/L and about 3.9 g/L, between about 3.8 g/L and about 6.0 g/L, between about 3.8 g/L and about 5.9 g/L, between about 3.8 g/L and about 5.8 g/L, between about 3.8 g/L and about 5.7 g/L, between about 3.8 g/L and about 5.6 g/L, between about 3.8 g/L and about 5.5 g/L, between about 3.8 g/L and about 5.4 g/L, between about 3.8 g/L and about 5.3 g/L, between about 3.8 g/L and about 5.2 g/L, between about 3.8 g/L and about 5.1 g/L, between about 3.8 g/L and about 5.0 g/L, between about 3.8 g/L and about 4.9 g/L, between about 3.8 g/L and about 4.8 g/L, between about 3.8 g/L and about 4.7 g/L, between about 3.8 g/L and about 4.6 g/L, between about 3.8 g/L and about 4.5 g/L, between about 3.8 g/L and about 4.4 g/L, between about 3.8 g/L and about 4.3 g/L, between about 3.8 g/L and about 4.2 g/L, between about 3.8 g/L and about 4.1 g/L, between about 3.8 g/L and about 4.0 g/L, between about 3.9 g/L and about 6.0 g/L, between about 3.9 g/L and about 5.9 g/L, between about 3.9 g/L and about 5.8 g/L, between about 3.9 g/L and about 5.7 g/L, between about 3.9 g/L and about 5.6 g/L, between about 3.9 g/L and about 5.5 g/L, between about 3.9 g/L and about 5.4 g/L, between about 3.9 g/L and about 5.3 g/L, between about 3.9 g/L and about 5.2 g/L, between about 3.9 g/L and about 5.1 g/L, between about 3.9 g/L and about 5.0 g/L, between about 3.9 g/L and about 4.9 g/L, between about 3.9 g/L and about 4.8 g/L, between about 3.9 g/L and about 4.7 g/L, between about 3.9 g/L and about 4.6 g/L, between about 3.9 g/L and about 4.5 g/L, between about 3.9 g/L and about 4.4 g/L, between about 3.9 g/L and about 4.3 g/L, between about 3.9 g/L and about 4.2 g/L, between about 3.9 g/L and about 4.1 g/L, between about 4.0 g/L and about 6.0 g/L, between about 4.0 g/L and about 5.9 g/L, between about 4.0 g/L and about 5.8 g/L, between about 4.0 g/L and about 5.7 g/L, between about 4.0 g/L and about 5.6 g/L, between about 4.0 g/L and about 5.5 g/L, between about 4.0 g/L and about 5.4 g/L, between about 4.0 g/L and about 5.3 g/L, between about 4.0 g/L and about 5.2 g/L, between about 4.0 g/L and about 5.1 g/L, between about 4.0 g/L and about 5.0 g/L, between about 4.0 g/L and about 4.9 g/L, between about 4.0 g/L and about 4.8 g/L, between about 4.0 g/L and about 4.7 g/L, between about 4.0 g/L and about 4.6 g/L, between about 4.0 g/L and about 4.5 g/L, between about 4.0 g/L and about 4.4 g/L, between about 4.0 g/L and about 4.3 g/L, between about 4.0 g/L and about 4.2 g/L, between about 4.1 g/L and about 6.0 g/L, between about 4.1 g/L and about 5.9 g/L, between about 4.1 g/L and about 5.8 g/L, between about 4.1 g/L and about 5.7 g/L, between about 4.1 g/L and about 5.6 g/L, between about 4.1 g/L and about 5.5 g/L, between about 4.1 g/L and about 5.4 g/L, between about 4.1 g/L and about 5.3 g/L, between about 4.1 g/L and about 5.2 g/L, between about 4.1 g/L and about 5.1 g/L, between about 4.1 g/L and about 5.0 g/L, between about 4.1 g/L and about 4.9 g/L, between about 4.1 g/L and about 4.8 g/L, between about 4.1 g/L and about 4.7 g/L, between about 4.1 g/L and about 4.6 g/L, between about 4.1 g/L and about 4.5 g/L, between about 4.1 g/L and about 4.4 g/L, between about 4.1 g/L and about 4.3 g/L, between about 4.2 g/L and about 6.0 g/L, between about 4.2 g/L and about 5.9 g/L, between about 4.2 g/L and about 5.8 g/L, between about 4.2 g/L and about 5.7 g/L, between about 4.2 g/L and about 5.6 g/L, between about 4.2 g/L and about 5.5 g/L, between about 4.2 g/L and about 5.4 g/L, between about 4.2 g/L and about 5.3 g/L, between about 4.2 g/L and about 5.2 g/L, between about 4.2 g/L and about 5.1 g/L, between about 4.2 g/L and about 5.0 g/L, between about 4.2 g/L and about 4.9 g/L, between about 4.2 g/L and about 4.8 g/L, between about 4.2 g/L and about 4.7 g/L, between about 4.2 g/L and about 4.6 g/L, between about 4.2 g/L and about 4.5 g/L, between about 4.2 g/L and about 4.4 g/L, between about 4.3 g/L and about 6.0 g/L, between about 4.3 g/L and about 5.9 g/L, between about 4.3 g/L and about 5.8 g/L, between about 4.3 g/L and about 5.7 g/L, between about 4.3 g/L and about 5.6 g/L, between about 4.3 g/L and about 5.5 g/L, between about 4.3 g/L and about 5.4 g/L, between about 4.3 g/L and about 5.3 g/L, between about 4.3 g/L and about 5.2 g/L, between about 4.3 g/L and about 5.1 g/L, between about 4.3 g/L and about 5.0 g/L, between about 4.3 g/L and about 4.9 g/L, between about 4.3 g/L and about 4.8 g/L, between about 4.3 g/L and about 4.7 g/L, between about 4.3 g/L and about 4.6 g/L, between about 4.3 g/L and about 4.5 g/L, between about 4.4 g/L and about 6.0 g/L, between about 4.4 g/L and about 5.9 g/L, between about 4.4 g/L and about 5.8 g/L, between about 4.4 g/L and about 5.7 g/L, between about 4.4 g/L and about 5.6 g/L, between about 4.4 g/L and about 5.5 g/L, between about 4.4 g/L and about 5.4 g/L, between about 4.4 g/L and about 5.3 g/L, between about 4.4 g/L and about 5.2 g/L, between about 4.4 g/L and about 5.1 g/L, between about 4.4 g/L and about 5.0 g/L, between about 4.4 g/L and about 4.9 g/L, between about 4.4 g/L and about 4.8 g/L, between about 4.4 g/L and about 4.7 g/L, between about 4.4 g/L and about 4.6 g/L, between about 4.5 g/L and about 6.0 g/L, between about 4.5 g/L and about 5.9 g/L, between about 4.5 g/L and about 5.8 g/L, between about 4.5 g/L and about 5.7 g/L, between about 4.5 g/L and about 5.6 g/L, between about 4.5 g/L and about 5.5 g/L, between about 4.5 g/L and about 5.4 g/L, between about 4.5 g/L and about 5.3 g/L, between about 4.5 g/L and about 5.2 g/L, between about 4.5 g/L and about 5.1 g/L, between about 4.5 g/L and about 5.0 g/L, between about 4.5 g/L and about 4.9 g/L, between about 4.5 g/L and about 4.8 g/L, between about 4.5 g/L and about 4.7 g/L, between about 4.6 g/L and about 6.0 g/L, between about 4.6 g/L and about 5.9 g/L, between about 4.6 g/L and about 5.8 g/L, between about 4.6 g/L and about 5.7 g/L, between about 4.6 g/L and about 5.6 g/L, between about 4.6 g/L and about 5.5 g/L, between about 4.6 g/L and about 5.4 g/L, between about 4.6 g/L and about 5.3 g/L, between about 4.6 g/L and about 5.2 g/L, between about 4.6 g/L and about 5.1 g/L, between about 4.6 g/L and about 5.0 g/L, between about 4.6 g/L and about 4.9 g/L, between about 4.6 g/L and about 4.8 g/L, between about 4.7 g/L and about 6.0 g/L, between about 4.7 g/L and about 5.9 g/L, between about 4.7 g/L and about 5.8 g/L, between about 4.7 g/L and about 5.7 g/L, between about 4.7 g/L and about 5.6 g/L, between about 4.7 g/L and about 5.5 g/L, between about 4.7 g/L and about 5.4 g/L, between about 4.7 g/L and about 5.3 g/L, between about 4.7 g/L and about 5.2 g/L, between about 4.7 g/L and about 5.1 g/L, between about 4.7 g/L and about 5.0 g/L, between about 4.7 g/L and about 4.9 g/L, between about 4.8 g/L and about 6.0 g/L, between about 4.8 g/L and about 5.9 g/L, between about 4.8 g/L and about 5.8 g/L, between about 4.8 g/L and about 5.7 g/L, between about 4.8 g/L and about 5.6 g/L, between about 4.8 g/L and about 5.5 g/L, between about 4.8 g/L and about 5.4 g/L, between about 4.8 g/L and about 5.3 g/L, between about 4.8 g/L and about 5.2 g/L, between about 4.8 g/L and about 5.1 g/L, between about 4.8 g/L and about 5.0 g/L, between about 4.9 g/L and about 6.0 g/L, between about 4.9 g/L and about 5.9 g/L, between about 4.9 g/L and about 5.8 g/L, between about 4.9 g/L and about 5.7 g/L, between about 4.9 g/L and about 5.6 g/L, between about 4.9 g/L and about 5.5 g/L, between about 4.9 g/L and about 5.4 g/L, between about 4.9 g/L and about 5.3 g/L, between about 4.9 g/L and about 5.2 g/L, between about 4.9 g/L and about 5.1 g/L, between about 5.0 g/L and about 6.0 g/L, between about 5.0 g/L and about 5.9 g/L, between about 5.0 g/L and about 5.8 g/L, between about 5.0 g/L and about 5.7 g/L, between about 5.0 g/L and about 5.6 g/L, between about 5.0 g/L and about 5.5 g/L, between about 5.0 g/L and about 5.4 g/L, between about 5.0 g/L and about 5.3 g/L, between about 5.0 g/L and about 5.2 g/L, between about 5.1 g/L and about 6.0 g/L, between about 5.1 g/L and about 5.9 g/L, between about 5.1 g/L and about 5.8 g/L, between about 5.1 g/L and about 5.7 g/L, between about 5.1 g/L and about 5.6 g/L, between about 5.1 g/L and about 5.5 g/L, between about 5.1 g/L and about 5.4 g/L, between about 5.1 g/L and about 5.3 g/L, between about 5.2 g/L and about 6.0 g/L, between about 5.2 g/L and about 5.9 g/L, between about 5.2 g/L and about 5.8 g/L, between about 5.2 g/L and about 5.7 g/L, between about 5.2 g/L and about 5.6 g/L, between about 5.2 g/L and about 5.5 g/L, between about 5.2 g/L and about 5.4 g/L, between about 5.3 g/L and about 6.0 g/L, between about 5.3 g/L and about 5.9 g/L, between about 5.3 g/L and about 5.8 g/L, between about 5.3 g/L and about 5.7 g/L, between about 5.3 g/L and about 5.6 g/L, between about 5.3 g/L and about 5.5 g/L, between about 5.4 g/L and about 6.0 g/L, between about 5.4 g/L and about 5.9 g/L, between about 5.4 g/L and about 5.8 g/L, between about 5.4 g/L and about 5.7 g/L, between about 5.4 g/L and about 5.6 g/L, between about 5.5 g/L and about 6.0 g/L, between about 5.5 g/L and about 5.9 g/L, between about 5.5 g/L and about 5.8 g/L, between about 5.5 g/L and about 5.7 g/L, between about 5.6 g/L and about 6.0 g/L, between about 5.6 g/L and about 5.9 g/L, between about 5.6 g/L and about 5.8 g/L, between about 5.7 g/L and about 6.0 g/L, between about 5.7 g/L and about 5.9 g/L, or between about 5.8 g/L and about 6.0 g/L) when the viable cell density in the medium is between about $60\times10^6$ cells/mL to about $90\times10^6$ cells/mL (e.g., between about $60\times10^6$ cells/mL and about $88\times10^6$ cells/mL, between about $60\times10^6$ cells/mL to about $86\times10^6$ cells/mL, between about $60\times10^6$ cells/mL and about $84\times10^6$ cells/mL, between about $60\times10^6$ cells/mL and about $82\times10^6$ cells/mL, between about $60\times10^6$ cells/mL and about $80\times10^6$ cells/mL, between about $60\times10^6$ cells/mL and about $78\times10^6$ cells/mL, between about $60\times10^6$ cells/mL and about $76\times10^6$ cells/mL, between about $60\times10^6$ cells/mL and about $74\times10^6$ cells/mL, between about $60\times10^6$ cells/mL and about $72\times10^6$ cells/mL, between about $60\times10^6$ cells/mL to about $70\times10^6$ cells/mL, between about $60\times10^6$ cells/mL and about $68\times10^6$ cells/mL, between about $60\times10^6$ cells/mL and about $66\times10^6$ cells/mL, between about $60\times10^6$ cells/mL and about $64\times10^6$ cells/mL, between about $60\times10^6$ cells/mL and about $62\times10^6$ cells/mL, between about $62\times10^6$ cells/mL and about $90\times10^6$ cells/mL, between about $62\times10^6$ cells/mL and about $88\times10^6$ cells/mL, between about $62\times10^6$ cells/mL to about $86\times10^6$ cells/mL, between about $62\times10^6$ cells/mL and about $84\times10^6$ cells/mL, between about $62\times10^6$ cells/mL and about $82\times10^6$ cells/mL, between about $62\times10^6$ cells/mL and about $80\times10^6$ cells/mL, between about $62\times10^6$ cells/mL and about $78\times10^6$ cells/mL, between about $62\times10^6$ cells/mL and about $76\times10^6$ cells/mL, between about $62\times10^6$ cells/mL and about $74\times10^6$ cells/mL, between about $62\times10^6$ cells/mL and about $72\times10^6$ cells/mL, between about $62\times10^6$ cells/mL to about $70\times10^6$ cells/mL, between about $62\times10^6$ cells/mL and about $68\times10^6$ cells/mL, between about $62\times10^6$ cells/mL and about $66\times10^6$ cells/mL, between about $62\times10^6$ cells/mL and about $64\times10^6$ cells/mL, between about $64\times10^6$ cells/mL and about $90\times10^6$ cells/mL, between about $64\times10^6$ cells/mL and about $88\times10^6$ cells/mL, between about $64\times10^6$ cells/mL to about $86\times10^6$ cells/mL, between about $64\times10^6$ cells/mL and about $84\times10^6$ cells/mL, between about $64\times10^6$ cells/mL and about $82\times10^6$ cells/mL, between about $64\times10^6$ cells/mL and about $80\times10^6$ cells/mL, between about $64\times10^6$ cells/mL and about $78\times10^6$ cells/mL, between about $64\times10^6$ cells/mL and about $76\times10^6$ cells/mL, between about $64\times10^6$ cells/mL and about $74\times10^6$ cells/mL, between about $64\times10^6$ cells/mL and about $72\times10^6$ cells/mL, between about $64\times10^6$ cells/mL to about $70\times10^6$ cells/mL, between about $64\times10^6$ cells/mL and about $68\times10^6$ cells/mL, between about $64\times10^6$ cells/mL and about $66\times10^6$ cells/mL, between about $66\times10^6$ cells/mL and about $90\times10^6$ cells/mL, between about $66\times10^6$ cells/mL and about $88\times10^6$ cells/mL, between about $66\times10^6$ cells/mL to about $86\times10^6$ cells/mL, between about $66\times10^6$ cells/mL and about $84\times10^6$ cells/mL, between about $66\times10^6$ cells/mL and about $82\times10^6$ cells/mL, between about $66\times10^6$ cells/mL and about $80\times10^6$ cells/mL, between about $66\times10^6$ cells/mL and about $78\times10^6$ cells/mL, between about $66\times10^6$ cells/mL and about $76\times10^6$ cells/mL, between about $66\times10^6$ cells/mL and about $74\times10^6$ cells/mL, between about $66\times10^6$ cells/mL and about $72\times10^6$ cells/mL, between about $66\times10^6$ cells/mL to about $70\times10^6$ cells/mL, between about $66\times10^6$ cells/mL and about $68\times10^6$ cells/mL, between about $68\times10^6$ cells/mL and about $90\times10^6$ cells/mL, between about $68\times10^6$ cells/mL and about $88\times10^6$ cells/mL, between about $68\times10^6$ cells/mL to about $86\times10^6$ cells/mL, between about $68\times10^6$ cells/mL and about $84\times10^6$ cells/mL, between about $68\times10^6$ cells/mL and about $82\times10^6$ cells/mL, between about $68\times10^6$ cells/mL and about $80\times10^6$ cells/mL, between about $68\times10^6$ cells/mL and about $78\times10^6$ cells/mL, between about $68\times10^6$ cells/mL and about $76\times10^6$ cells/mL, between about $68\times10^6$ cells/mL and about $74\times10^6$ cells/mL, between about $68\times10^6$ cells/mL and about $72\times10^6$ cells/mL, between about $68\times10^6$ cells/mL to about $70\times10^6$ cells/mL, between about $70\times10^6$ cells/mL and about $90\times10^6$ cells/mL, between about $70\times10^6$ cells/mL and about $88\times10^6$ cells/mL, between about $70\times10^6$ cells/mL to about $86\times10^6$ cells/mL, between about $70\times10^6$ cells/mL and about $84\times10^6$ cells/mL, between about $70\times10^6$ cells/mL and about $82\times10^6$ cells/mL, between about $70\times10^6$ cells/mL and about $80\times10^6$ cells/mL, between about $70\times10^6$ cells/mL and about $78\times10^6$ cells/mL, between about $70\times10^6$ cells/mL and about $76\times10^6$ cells/mL, between about $70\times10^6$ cells/mL and about $74\times10^6$ cells/mL, between about $70\times10^6$ cells/mL and about $72\times10^6$ cells/mL, between about $72\times10^6$ cells/mL and about $90\times10^6$ cells/mL, between about $72\times10^6$ cells/mL and about $88\times10^6$ cells/mL, between about $72\times10^6$ cells/mL to about $86\times10^6$ cells/mL, between about $72\times10^6$ cells/mL and about $84\times10^6$ cells/mL, between about $72\times10^6$ cells/mL and about $82\times10^6$ cells/mL, between about $72\times10^6$ cells/mL and about $80\times10^6$ cells/mL, between about $72\times10^6$ cells/mL and about $78\times10^6$ cells/mL, between about $72\times10^6$ cells/mL and about $76\times10^6$ cells/mL, between about $72\times10^6$ cells/mL and about $74\times10^6$ cells/mL, between about $74\times10^6$ cells/mL and about $90\times10^6$ cells/mL, between about $74\times10^6$ cells/mL and about $88\times10^6$ cells/mL, between about $74\times10^6$ cells/mL to about $86\times10^6$ cells/mL, between about $74\times10^6$ cells/mL and about $84\times10^6$ cells/mL, between about $74\times10^6$ cells/mL and about $82\times10^6$ cells/mL, between about $74\times10^6$ cells/mL and about $80\times10^6$ cells/mL, between about $74\times10^6$ cells/mL and about $78\times10^6$ cells/mL, between about $74\times10^6$ cells/mL and about $76\times10^6$ cells/mL, between about $76\times10^6$ cells/mL and about $90\times10^6$ cells/mL, between about $76\times10^6$ cells/mL and about $88\times10^6$ cells/mL, between about $76\times10^6$ cells/mL to about $86\times10^6$ cells/mL, between about $76\times10^6$ cells/mL and about $84\times10^6$ cells/mL, between about $76\times10^6$ cells/mL and about $82\times10^6$ cells/mL, between about $76\times10^6$ cells/mL and about $80\times10^6$ cells/mL, between about $76\times10^6$ cells/mL and about $78\times10^6$ cells/mL, between about $78\times10^6$ cells/mL and about $90\times10^6$ cells/mL, between about $78\times10^6$ cells/mL and about $88\times10^6$ cells/mL, between about $78\times10^6$ cells/mL to about $86\times10^6$ cells/mL, between about $78\times10^6$ cells/mL and about $84\times10^6$ cells/mL, between about $78\times10^6$ cells/mL and about $82\times10^6$ cells/mL, between about $78\times10^6$ cells/mL and about $80\times10^6$ cells/mL, between about $80\times10^6$ cells/mL and about $90\times10^6$ cells/mL, between about $80\times10^6$ cells/mL and about $88\times10^6$ cells/mL, between about $80\times10^6$ cells/mL to about $86\times10^6$ cells/mL, between about $80\times10^6$ cells/mL and about $84\times10^6$ cells/mL, between about $80\times10^6$ cells/mL and about $82\times10^6$ cells/mL, between about $82\times10^6$ cells/mL and about $90\times10^6$ cells/mL, between about $82\times10^6$ cells/mL and about $88\times10^6$ cells/mL, between about $82\times10^6$ cells/mL to about $86\times10^6$ cells/mL, between about $82\times10^6$ cells/mL and about $84\times10^6$ cells/mL, between about $84\times10^6$ cells/mL and about $90\times10^6$ cells/mL, between about $84\times10^6$ cells/mL and about $88\times10^6$ cells/mL, between about $84\times10^6$ cells/mL to about $86\times10^6$ cells/mL, between about $86\times10^6$ cells/mL and about $90\times10^6$ cells/mL, between about $86\times10^6$ cells/mL and about $88\times10^6$ cells/mL, or between about $88\times10^6$ cells/mL and about $90\times10^6$ cells/mL).

Any of the methods described herein can include increasing the poloxamer-188 concentration in the medium to greater than 6.0 g/L (e.g., greater than 6.1 g/L, greater than 6.2 g/L, greater than 6.3 g/L, greater than 6.4 g/L, greater than 6.5 g/L, greater than 6.6 g/L, greater than 6.7 g/L, greater than 6.8 g/L, greater than 6.9 g/L, greater than 7.0 g/L, greater than 7.1 g/L, greater than 7.2 g/L, greater than 7.3 g/L, greater than 7.4 g/L, greater than 7.5 g/L, greater than 7.6 g/L, greater than 7.7 g/L, greater than 7.8 g/L, greater than 7.9 g/L, greater than 8.0 g/L, greater than 8.1 g/L, greater than 8.2 g/L, greater than 8.3 g/L, greater than 8.4 g/L, greater than 8.5 g/L, greater than 8.6 g/L, greater than 8.7 g/L, greater than 8.8 g/L, greater than 8.9 g/L, greater than 9.0 g/L, greater than 9.1 g/L, greater than 9.2 g/L, greater than 9.3 g/L, greater than 9.4 g/L, greater than 9.5 g/L, greater than 9.6 g/L, greater than 9.7 g/L, greater than 9.8 g/L, greater than 9.9 g/L, greater than 10.0 g/L, greater than about 10.1 g/L, greater than about 10.2 g/L, greater than about 10.3 g/L, greater than about 10.4 g/L, greater than about 10.5 g/L, greater than about 10.6 g/L, greater than about 10.7 g/L, greater than about 10.8 g/L, greater than about 10.9 g/L, or greater than about 11.0 g/L) poloxamer-188, when the viable cell density in the medium is greater than between about $90\times10^6$ cells/mL (e.g., greater than about $91\times10^6$ cells/mL, greater than about $92\times10^6$ cells/mL, greater than about $93\times10^6$ cells/mL, greater than about $94\times10^6$ cells/mL, greater than about $95\times10^6$ cells/mL, greater than about $96\times10^6$ cells/mL, greater than about $97\times10^6$ cells/mL, greater than about $98\times10^6$ cells/mL, greater than about $99\times10^6$ cells/mL, greater than about $100\times10^6$ cells/mL, greater than about $101\times10^6$ cells/mL, greater than about $102\times10^6$ cells/mL, greater than about $103\times10^6$ cells/mL, greater than about $104\times10^6$ cells/mL, greater than about $105\times10^6$ cells/mL, greater than about $106\times10^6$ cells/mL, greater than about $107\times10^6$ cells/mL, greater than about $108\times10^6$ cells/mL, greater than about $109\times10^6$ cells/mL, greater than about $110\times10^6$ cells/mL, greater than about $111\times10^6$ cells/mL, greater than about $112\times10^6$ cells/mL, greater than about $113\times10^6$ cells/mL, greater than about $114\times10^6$ cells/mL, greater than about $115\times10^6$ cells/mL, greater than about $116\times10^6$ cells/mL, greater than about $117\times10^6$ cells/mL, greater than about $118\times10^6$ cells/mL, greater than about $119\times10^6$ cells/mL, or greater than about $120\times10^6$ cells/mL).

In some embodiments, the methods include: increasing the poloxamer-188 concentration in the medium to between about 1.8 g/L to about 3.0 g/L (e.g., any of the ranges therebetween described herein) when the viable cell density in the medium is between about $35\times10^6$ cells/mL to about $60\times10^6$ cells/mL (e.g., or any of the ranges therebetween described herein); increasing the poloxamer-188 concentration in the medium to between about 3.0 g/L to about 6.0 g/L (e.g., any of the ranges therebetween described herein) when the viable cell concentration density in the medium is between about $60\times10^6$ cells/mL to about $90\times10^6$ cells/mL (e.g., any of the ranges therebetween described herein); and increasing the poloxamer-188 concentration in the medium to greater than 6.0 g/L (e.g., any of the concentrations greater than 6.0 g/L described herein) when the viable cell density concentration in the medium is greater than $90\times10^6$ cells/mL (e.g., any of the viable cell densities greater than $90\times10^6$ cells/mL described herein). Some embodiments of any of the methods described herein further include determining the viable cell density in the medium at one or more (e.g., two, three, four, five, six, seven, eight, nine, ten, eleven, twelve, thirteen, fourteen, fifteen, sixteen, seventeen, eighteen, nineteen, or twenty) time points during the culturing.

Poloxamer-188 to AntiFoam Ratio

In any of the embodiments described herein, the liquid medium comprises antifoam (e.g., antifoam-c) and the ratio of antifoam (g/L) to poloxamer-188 (g/L) in the medium is between about 0.5% to about 6.0% (e.g., between about 0.5% and about 5.5%, between about 0.5% and about 5.0%, between about 0.5% and about 4.5%, between about 0.5% and about 4.0%, between about 0.5% and about 3.5%, between about 0.5% and about 3.0%, between about 0.5% and about 2.5%, between about 0.5% and about 2.0%, between about 0.5% and about 1.5%, between about 0.5% and about 1.0%, between about 1.0% and about 6.0%, between about 1.0% and about 5.5%, between about 1.0% and about 5.0%, between about 1.0% and about 4.5%, between about 1.0% and about 4.0%, between about 1.0% and about 3.5%, between about 1.0% and about 3.0%, between about 1.0% and about 2.5%, between about 1.0% and about 2.0%, between about 1.0% and about 1.5%, between about 2.0% and about 6.0%, between about 2.0% and about 5.5%, between about 2.0% and about 5.0%, between about 2.0% and about 4.5%, between about 2.0% and about 4.0%, between about 2.0% and about 3.5%, between about 2.0% and about 3.0%, between about 2.0% and about 2.5%, between about 2.5% and about 6.0%, between about 2.5% and about 5.5%, between about 2.5% and about 5.0%, between about 2.5% and about 4.5%, between about 2.5% and about 4.0%, between about 2.5% and about 3.5%, between about 2.5% and about 3.0%, between about 3.0% and about 6.0%, between about 3.0% and about 5.5%, between about 3.0% and about 5.0%, between about 3.0% and about 4.5%, between about 3.0% and about 4.0%, between about 3.0% and about 3.5%, between about 3.5% and about 6.0%, between about 3.5% and about 5.5%, between about 3.5% and about 5.0%, between about 3.5% and about 4.5%, between about 3.5% and about 4.0%, between about 4.0% and about 6.0%, between about 4.0% and about 5.5%, between about 4.0% and about 5.0%, between about 4.0% and about 4.5%, between about 4.5% and about 6.0%, between about 4.5% and about 5.5%, between about 4.5% and about 5.0%, between about 5.0% and about 6.0%, between about 5.0% and about 5.5%, or between about 5.5% and about 6.0%).

Culture Media

Liquid culture media are known in the art. The liquid culture media (e.g., a first and/or second liquid medium) can be supplemented with a mammalian serum (e.g., fetal calf serum and bovine serum), and/or a growth hormone or growth factor (e.g., insulin, transferrin, and epidermal growth factor). Alternatively or in addition, the liquid culture media (e.g., a first and/or second liquid medium) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells (e.g., mammalian cells) in any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid medium and medium components are known in the art.

Skilled practitioners will appreciate that the first liquid medium and the second or feed liquid medium described herein can be the same type of media or different media.

Liquid medium obtained from a cell culture can be filtered or clarified to obtain a liquid medium that is substantially free of cells and/or viruses. Methods for filtering or clarifying a liquid medium in order to remove cells are known in the art (e.g., 0.2-μm filtration and filtration using an Alternating Tangential Flow (ATFTM) system). Mammalian cells can also be removed from liquid medium using centrifugation and removing the supernatant that is liquid medium that is substantially free of cells, or by allowing the cells to settle to the gravitational bottom of a vessel or bioreactor containing the liquid medium, and removing the liquid medium (the liquid medium that is substantially free of cells) that is distant from the settled recombinant cells.

Temperature

The step of culturing of mammalian cells can be performed at a temperature of about 31° C. to about 40° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the bioreactor with the cell (e.g., mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20 degrees C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

$CO_2$

The culturing step described herein can further include exposing the liquid medium in the bioreactor to an atmosphere containing at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$).

Recombinant Proteins

Non-limiting examples of recombinant proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). The recombinant protein can be an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant antibodies that can be produced by the methods described herein are known in the art. Additional non-limiting examples of recombinant proteins that can be produced by the present methods include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-la, imiglucerase, dornase alfa, epoetin alfa, insulin or insulin analogs, mecasermin, factor VIII, factor VIIa, anti-thrombin III, protein C, human albumin, erythropoietin, granulocyte colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase.

Additional examples of recombinant proteins that can be produced by the present methods include acid a-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

A secreted, soluble recombinant protein can be recovered from the liquid medium (e.g., a first and/or second liquid medium) by removing or otherwise physically separating the liquid medium from the cells (e.g., mammalian cells). A variety of different methods for removing liquid medium from cells (e.g., mammalian cells) are known in the art, including, for example, centrifugation, filtration, pipetting, and/or aspiration. The secreted recombinant protein can then be recovered and further purified from the liquid medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

Collecting the Recombinant Protein

Some embodiments further include collecting the recombinant protein (e.g., any of the recombinant proteins described herein). In some examples, the collecting includes lysing the mammalian cells. In other examples, collecting can include collecting the recombinant protein from the medium (e.g., one or both of the first and second liquid medium when perfusion culturing is performed, or one or both of the first liquid medium and the feed liquid medium when batch culturing is performed).

Collecting can be performed after the culturing achieves a viable cell density of, e.g., greater than about $30\times10^6$ cells/mL, greater than about $32\times10^6$ cells/mL, greater than about $34\times10^6$ cells/mL, greater than about $36\times10^6$ cells/mL, greater than about $38\times10^6$ cells/mL, greater than about $40\times10^6$ cells/mL, greater than about $42\times10^6$ cells/mL, greater than about $44\times10^6$ cells/mL, greater than about $46\times10^6$ cells/mL, greater than about $48\times10^6$ cells/mL, greater than about $50\times10^6$ cells/mL, greater than about $52\times10^6$ cells/mL, greater than about $54\times10^6$ cells/mL, greater than about $56\times10^6$ cells/mL, greater than about $58\times10^6$ cells/mL, greater than about $60\times10^6$ cells/mL, greater than about $62\times10^6$ cells/mL, greater than about $64\times10^6$ cells/mL, greater than about $66\times10^6$ cells/mL, greater than about $68\times10^6$ cells/mL, greater than about $70\times10^6$ cells/mL, greater than about $72\times10^6$ cells/mL, greater than about $74\times10^6$ cells/mL, greater than about $76\times10^6$ cells/mL, greater than about $78\times10^6$ cells/mL, greater than about $80\times10^6$ cells/mL, greater than about $82\times10^6$ cells/mL, greater than about $84\times10^6$ cells/mL, greater than about $86\times10^6$ cells/mL, greater than about $88\times10^6$ cells/mL, greater than about $90\times10^6$ cells/mL, greater than about $92\times10^6$ cells/mL, greater than about $94\times10^6$ cells/mL, greater than about $96\times10^6$ cells/mL, greater than about $98\times10^6$ cells/mL, greater than about $100\times10^6$ cells/mL, greater than about $102\times10^6$ cells/mL, greater than about $104\times10^6$ cells/mL, greater than about $106\times10^6$ cells/mL, greater than about $108\times10^6$ cells/mL, greater than about $110\times10^6$ cells/mL, greater than about $112\times10^6$ cells/mL, greater than about $114\times10^6$ cells/mL, greater than about $116\times10^6$ cells/mL, greater than about $118\times10^6$ cells/mL, greater than about $120\times10^6$ cells/mL, greater than about $122\times10^6$ cells/mL, greater than about $124\times10^6$ cells/mL, greater than about $126\times10^6$ cells/mL, greater than about $128\times10^6$ cells/mL, greater than about $130\times10^6$ cells/mL, greater than about $132\times10^6$ cells/mL, greater than about $134\times10^6$ cells/mL, greater than about $136\times10^6$ cells/mL, greater than about $138\times10^6$ cells/mL, greater than about $140\times10^6$ cells/mL, greater than about $142\times10^6$ cells/mL, greater than about $144\times10^6$ cells/mL, greater than about $146\times10^6$ cells/mL, greater than about $148\times10^6$ cells/mL, greater than about $150\times10^6$ cells/mL, greater than about $152\times10^6$ cells/mL, greater than about $154\times10^6$ cells/mL, greater than about $156\times10^6$ cells/mL, greater than about $158\times10^6$ cells/mL, greater than about $160\times10^6$ cells/mL, greater than about $162\times10^6$ cells/mL, greater than about $164\times10^6$ cells/mL, greater than about $166\times10^6$ cells/mL, greater than about $168\times10^6$ cells/mL, greater than about $170\times10^6$ cells/mL, greater than about $172\times10^6$ cells/mL, greater than about $174\times10^6$ cells/mL, greater than about $176\times10^6$ cells/mL, greater than about $178\times10^6$ cells/mL, greater than about $180\times10^6$ cells/mL, greater than about $182\times10^6$ cells/mL, greater than about $184\times10^6$ cells/mL, greater than about $186\times10^6$ cells/mL, greater than about $188\times10^6$ cells/mL, greater than about $190\times10^6$ cells/mL, greater than about $192\times10^6$ cells/mL, greater than about $194\times10^6$ cells/mL, greater than about $196\times10^6$ cells/mL, greater than about $198\times10^6$ cells/mL, or greater than about $200\times10^6$ cells/mL).

Formulating the Recombinant Protein

Some embodiments of any of the methods described herein further include a step of formulating the recombinant protein (e.g., collected recombinant protein) into a pharmaceutical composition. For example, formulating can include adding a pharmaceutically acceptable excipient to the recombinant protein (e.g., collected recombinant protein). Formulating can include mixing a pharmaceutically acceptable excipient with the recombinant protein (e.g., collected recombinant protein). Examples of pharmaceutically acceptable excipients (e.g., non-naturally occurring pharmaceutically acceptable excipients) are well known in the art. In some embodiments, the recombinant protein (e.g., collected recombinant protein) is formulated for intravenous, intraarterial, subcutaneous, intraperitoneal, or intramuscular administration.

EXAMPLES

Example 1. Effect of Increased Concentrations of Poloxamer-188 on a Perfusion Cell Culture Producing a Secreted Recombinant Antibody This set of experiments was performed to test the effect of increasing concentrations of poloxamer-188 on cell growth and recombinant antibody production in a perfusion cell culture including mammalian cells containing a nucleic acid encoding the recombinant antibody. In these experiments, a first perfusion cell culture run was performed which used CD-CHO media containing 1.8 g/L over the entire culture period and a second perfusion cell culture run was performed which used CD-CHO media containing increasing concentrations of poloxamer-188 over the culture period (increasing from 1.8 g/L to 6.8 g/L poloxamer-188 over the culture period). For each cell culture run, perfusion was performed at a rate of 4 reactor volumes (RVs)/day on day 12 through day 33 of the culture, switching to a rate of 6 RVs/day on day 33 through day 63 of the culture, and switching to a rate of 7 RVs/day on day 63 through day 72 of the culture. The second cell culture run was performed using CD-CHO medium containing 1.8 g/L poloxamer-188 on day 0 through day 14 of the culture, CD-CHO medium, containing 2.8 g/L poloxamer-188 on day 15 through day 34 of the culture, CD-CHO medium containing 3.8 g/L poloxamer-188 on day 35 through day 39 of the culture, CD-CHO medium containing 4.8 g/L poloxamer-188 on day 40 through day 56 of the culture, and CD-CHO medium containing 5.8 g/L poloxamer-188 on day 57 through day 72 of the culture.

The viable cell density, the specific growth rate, the percentage of viable cells, the volumetric productivity rate, and the specific productivity rate were determined each day for both the first and second perfusion cultures using well-known methods.

Figure 1:
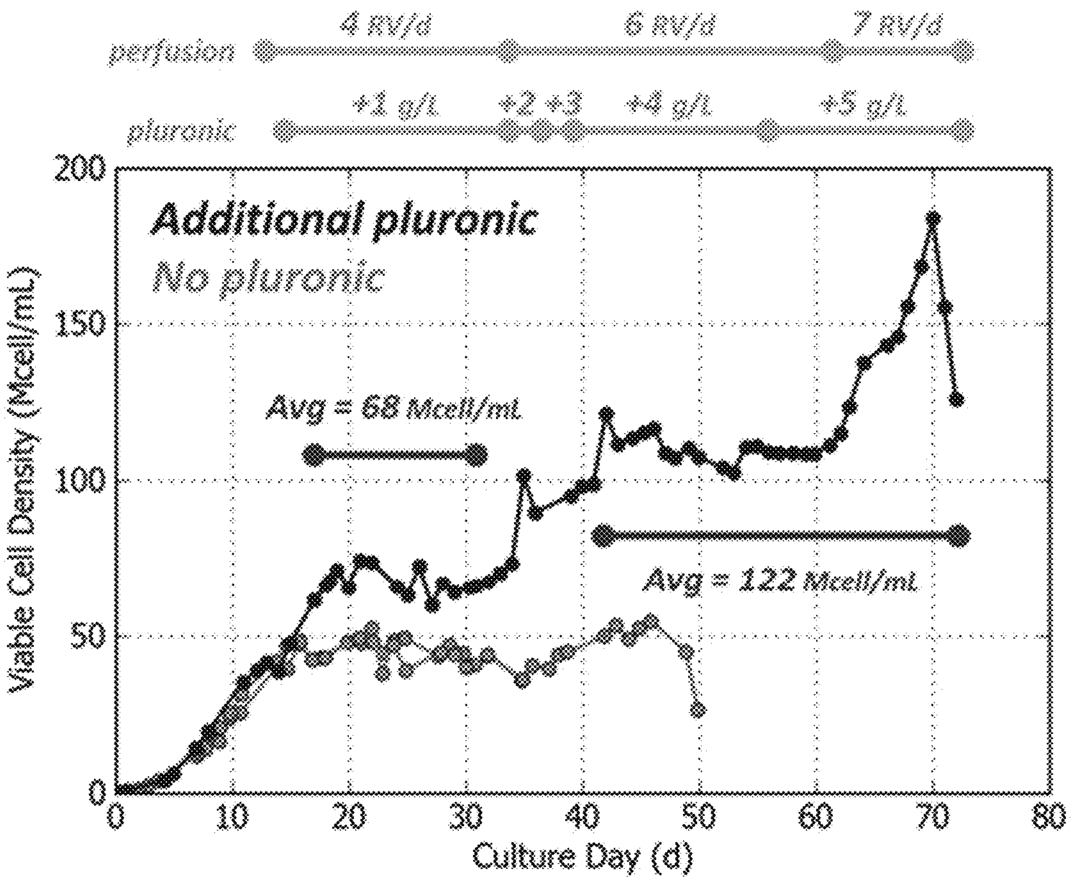
FIG. 1 is a graph of the viable cell density over time in a perfusion cell culture run performed using a liquid medium containing no additional poloxamer-188 over the length of the culture period (a steady concentration of 1.8 g/L poloxamer-188 over the length of the culture period) (grey data) and a perfusion cell culture run performed using liquid culture media that contain increasing amounts of poloxamer- 188 over the length of the culture period (increasing from 1.8 g/L to 6.8 g/L poloxamer-188 over the length of the culture period) (black data).
Figure 2:
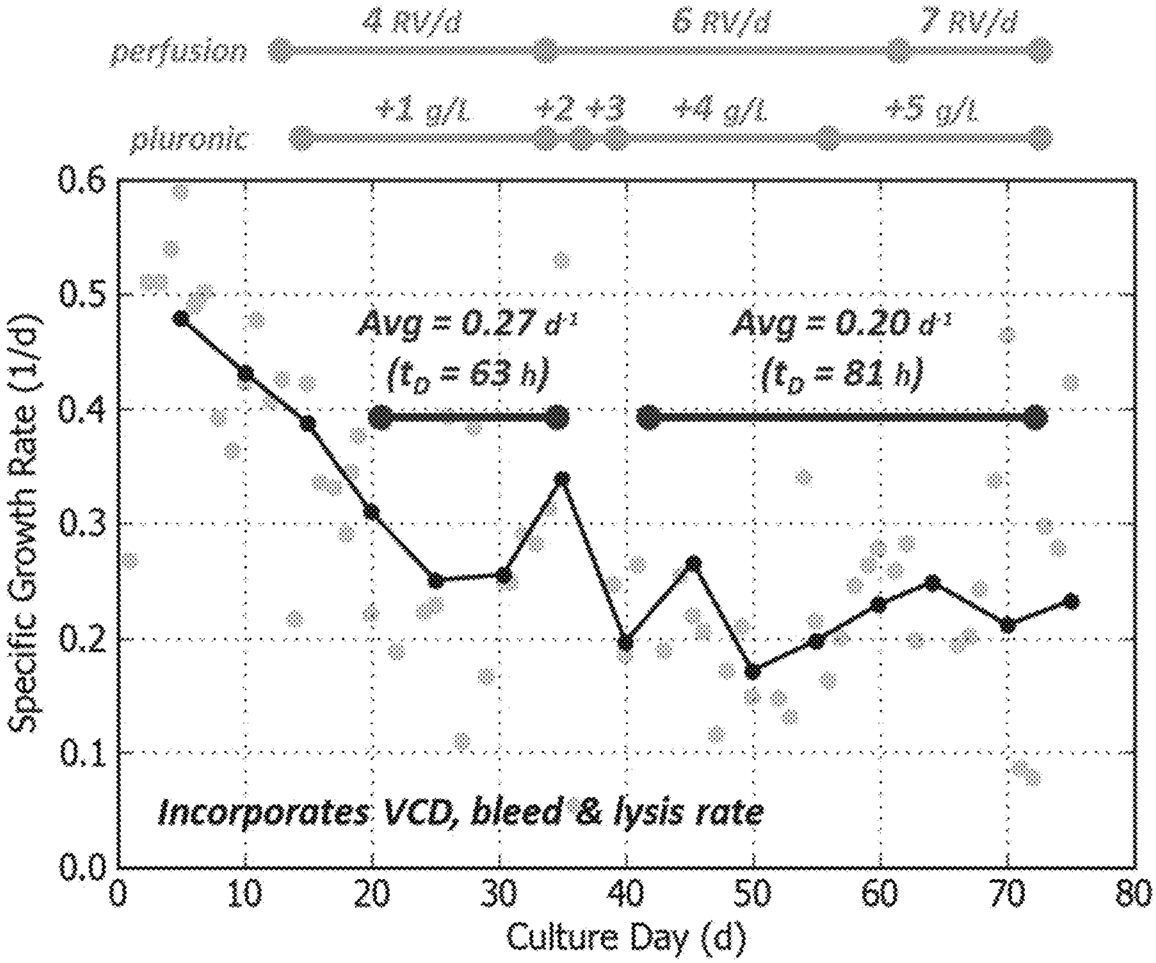
FIG. 2 is a graph of the specific growth rate over time in a perfusion cell culture run performed using liquid culture media that contain increasing amounts of poloxamer-188 over the length of the culture period (increasing from 1.8 g/L to 6.8 g/L poloxamer-188 over the length of the culture period).
Figure 3:
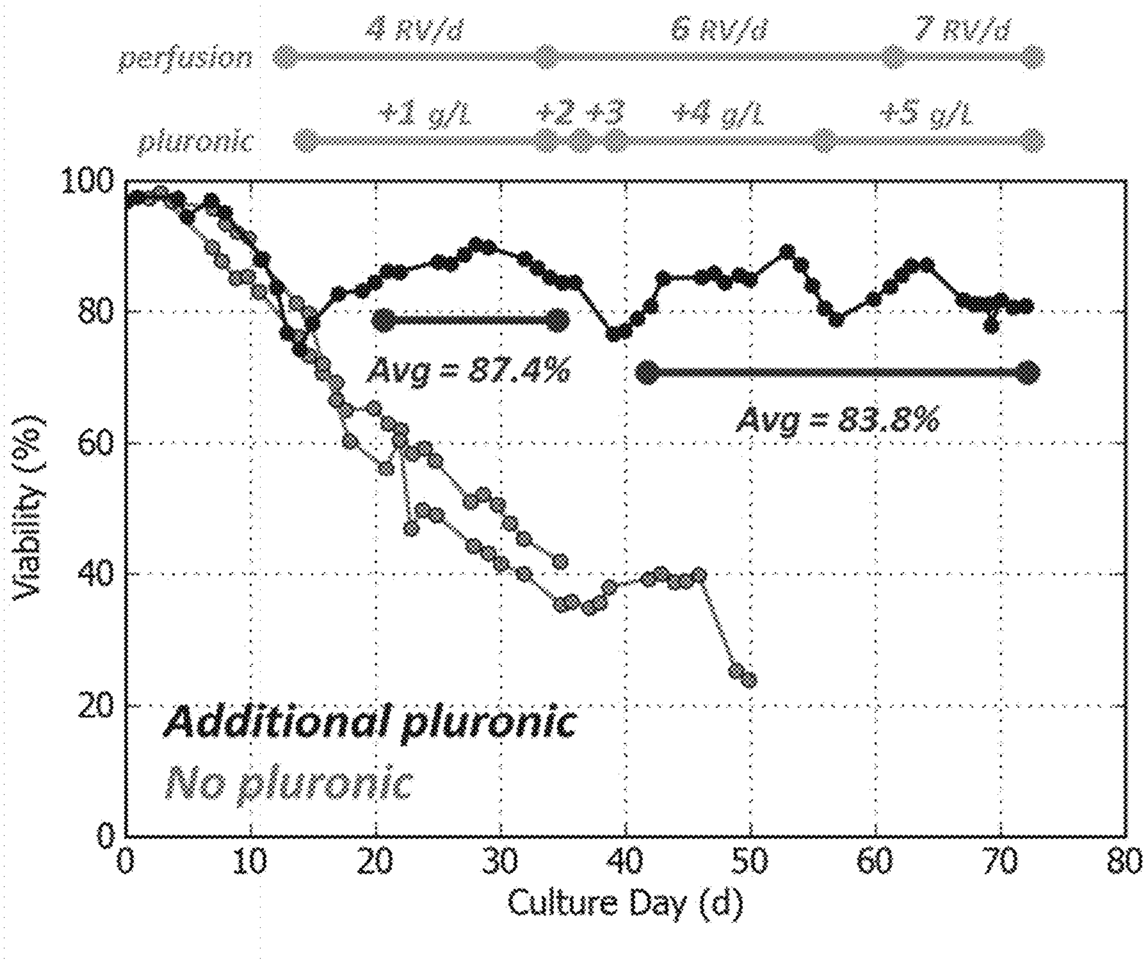
FIG. 3 is a graph of the percentage of viable cells in two perfusion cell culture runs performed using a liquid medium containing no additional poloxamer-188 over the length of the culture period (a steady concentration of 1.8 g/L poloxamer-188 over the length of the culture period) (grey data) and a perfusion cell culture run performed using liquid culture media that contain increasing amounts of poloxamer-188 over the length of the culture period (increasing from 1.8 g/L to 6.8 g/L poloxamer-188 over the length of the culture period) (black data).

The data show that viable cell densities exceeding 100×$10^6$ cells/mL are achieved by establishing a poloxamer-188 concentration of greater than 1.8 g/L in the culture (FIG. 1). In contrast, the first cell culture run that used only 1.8 g/L poloxamer-188 in the culture media only achieved a viable cell density of 50×$10^6$ cells/mL (FIG. 1). The data for the second cell culture run also show that establishing a poloxamer-188 concentration of greater than 1.8 g/L in the culture results in a robust specific growth rate, even when the cell culture has a viable cell density greater than 100×$10^6$ cells/mL (FIG. 2). The data in FIG. 3 also show that establishing a poloxamer-188 concentration of greater than 1.8 g/L in the culture results in a high and steady percentage of viable cells (above 80% throughout the culture period) as compared to the perfusion cell culture run that used culture media containing 1.8 g/L poloxamer-188 throughout the culture period (FIG. 3).

Figure 4:
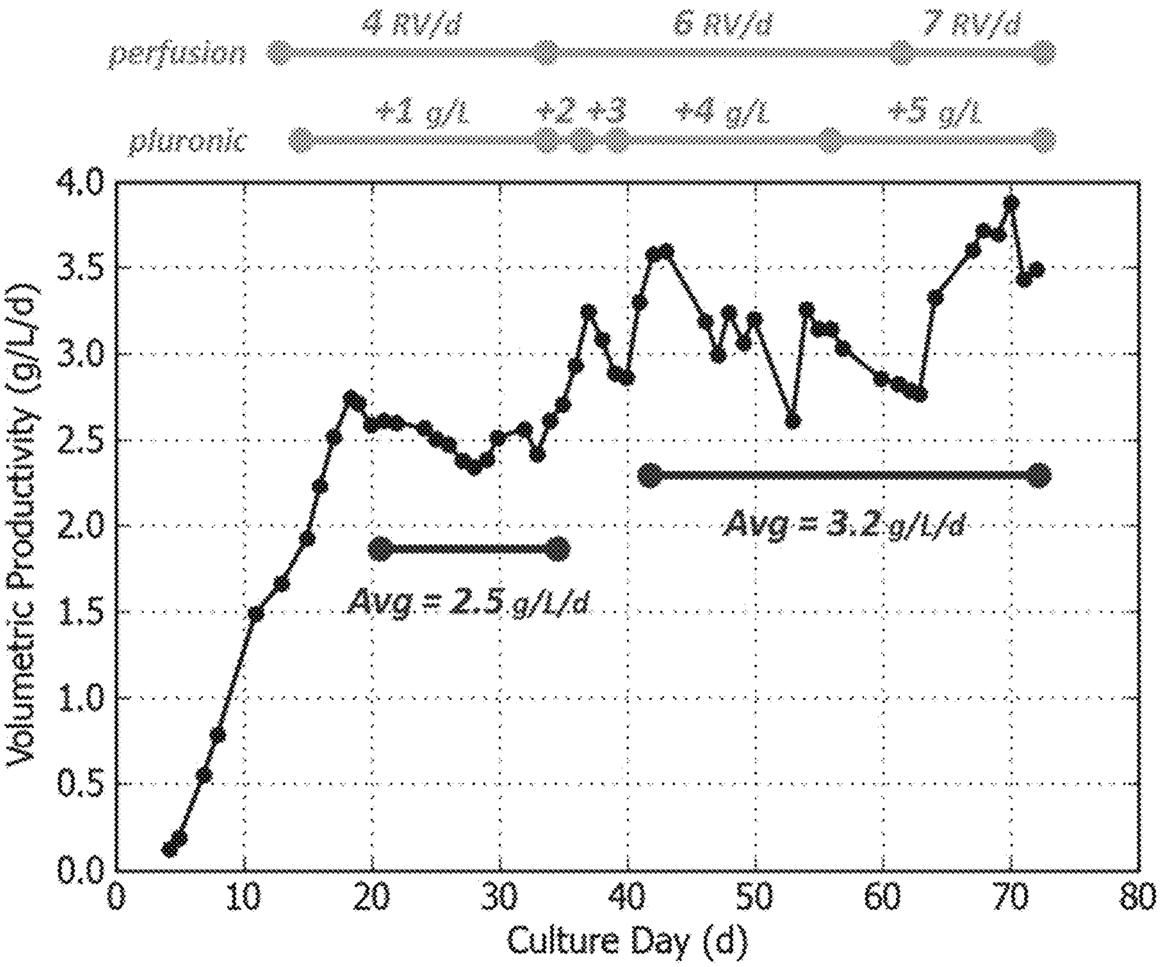
FIG. 4 is a graph of the volumetric productivity over time in a perfusion cell culture run performed using liquid culture media that contain increasing amounts of poloxamer-188 over the length of the culture period (increasing from 1.8 g/L to 6.8 g/L poloxamer-188 over the length of the culture period).
Figure 5:
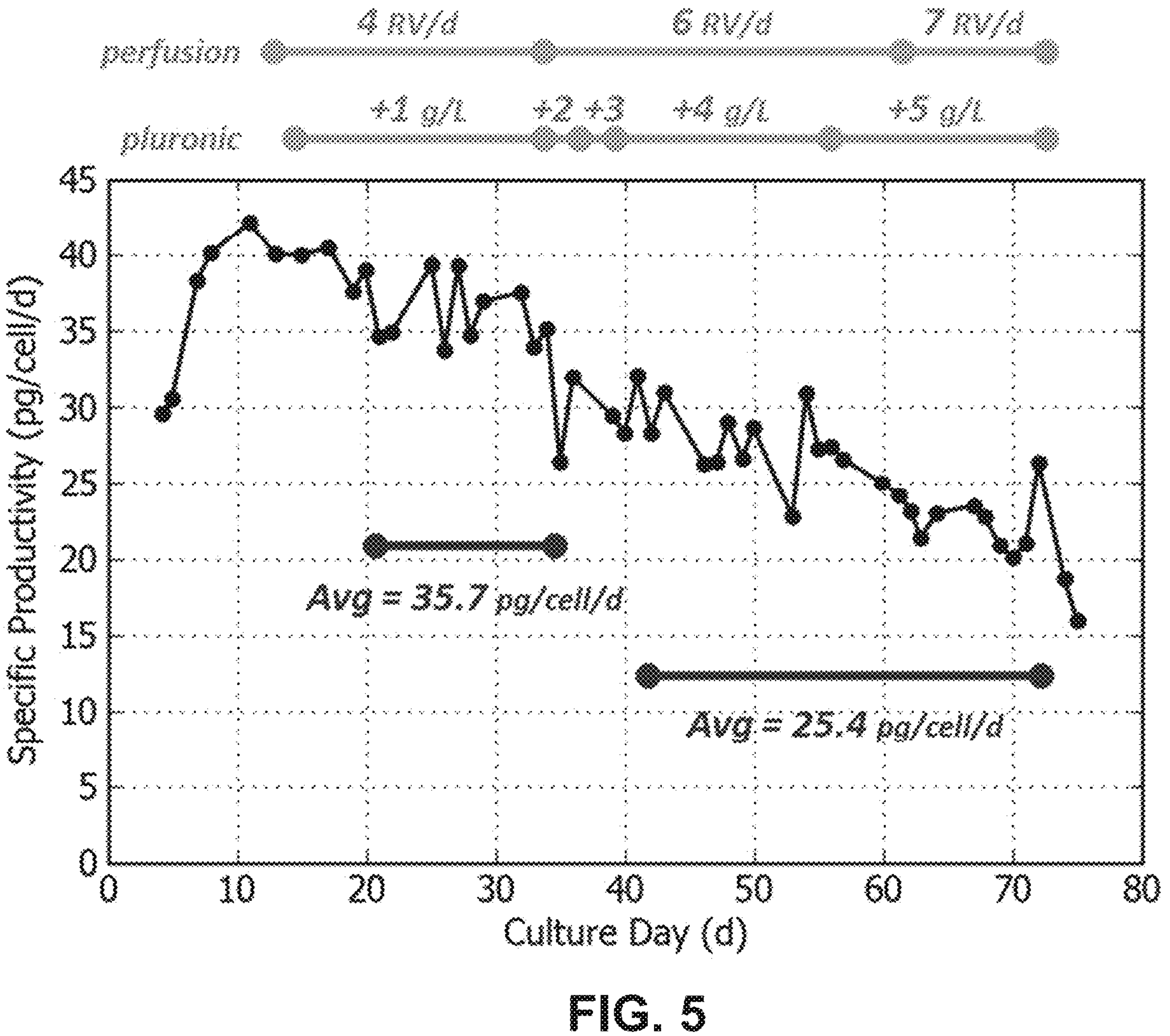
FIG. 5 is a graph of the specific productivity over time in a perfusion cell culture run performed using liquid culture media that contain increasing amounts of poloxamer-188 over the length of the culture period (increasing from 1.8 g/L to 6.8 g/L poloxamer-188 over the length of the culture period).

The data in FIGS. 4 and 5 also show that the second perfusion cell culture run performed with culture media containing increasing concentrations of poloxamer-188 over the culture period (increasing from 1.8 g/L to 6.8 g/L poloxamer-188) has high volumetric productivity rates (greater than 3 g/L/d) and high specific productivity rates (between 15 pg/cell/day to 42 pg/cell/day), respectively.

Example 2. Effect of Increased Concentrations of Poloxamer-188 on Stability of a Recombinant Antibody in Liquid Medium A set of experiments was performed to determine whether increased concentrations of poloxamer-188 would inhibit degradation of a recombinant protein present in a clarified liquid medium after harvest from a cell culture. In these experiments, a perfusion cell culture run similar to the second perfusion cell culture run described in Example 1 was performed, except after the culture achieved a concentration of 6.8 g/L poloxamer-188, the poloxamer-188 concentration in the culture was reduced to 3.95 g/L poloxamer-188, and then reduced once again to 3.0 g/L poloxamer-188. In these experiments, two or three samples of the liquid medium were removed from the culture at the following time points: a first time point when the culture contained 6.8 g/L poloxamer-188, a second time point when the culture contained a concentration of 3.95 g/L poloxamer-188, and a third time point when the culture contained a concentration of 3.0 g/L poloxamer-188. One sample collected from each of the time points was stored at 4° C., one sample collected from each of the time points was incubated for 7 days at room temperature prior to storage at 4° C., and for each of the second and third time points, a sample was supplemented with poloxamer-188 to achieve a concentration of 6.8 g/L polaxmer-188 in each sample, and then each sample was incubated for 9 days at room temperature prior to storage at 4° C. The resulting untreated and treated samples were run on a 4-20% Bis-Tris Gel and stained with Coomassie Blue.

Figure 6:
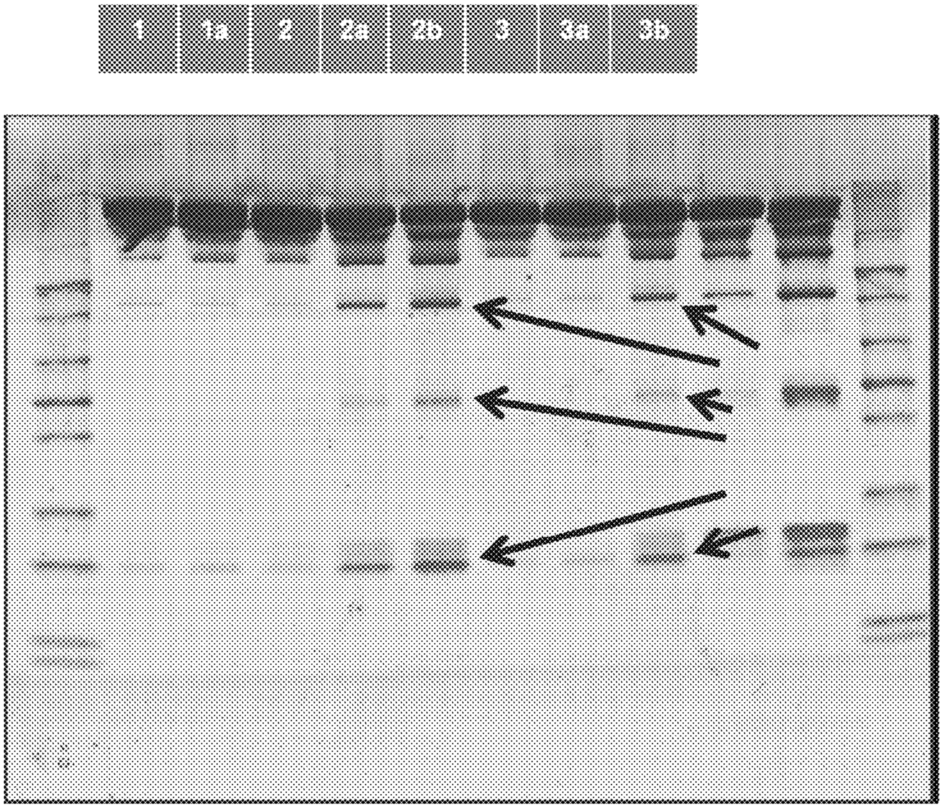
FIG. 6 is a Bis-Tris gel showing the degradation products of a recombinant antibody present in: clarified liquid medium harvested from a perfusion cell culture containing 6.8 g/L poloxamer-188 (lane 1); clarified liquid medium harvested from a perfusion cell culture containing 6.8 g/L poloxamer-188 that has been incubated for 7 days at room temperature (lane 1*a*); clarified liquid medium harvested from a perfusion cell culture containing 3.95 g/L poloxamer-188 (lane 2); clarified liquid medium harvested from a perfusion cell culture containing 3.95 g/L poloxamer-188 and incubated for 7 days at room temperature (lane 2*a*); clarified liquid medium harvested from a perfusion cell culture containing 3.95 g/L poloxamer-188, supplemented with poloxmer-188 to reach a concentration of 6.8 g/L poloxamer-188, and incubated at room temperature for 9 days (lane 2*b*); clarified liquid medium harvested from a perfusion cell culture containing 3.0 g/L poloxamer-188 (lane 3); clarified liquid medium harvested from a perfusion cell culture containing 3.0 g/L poloxamer-188 and incubated at room temperature for 7 days (lane 3*a*); and clarified liquid medium harvested from a perfusion cell culture containing 3.0 g/L poloxamer-188, supplemented with poloxamer-188 to reach a concentration of 6.8 g/L poloxamer-188, and incubated for 9 days at room temperature (lane 3*b*).

The data in FIG. 6 show that the untreated samples containing 6.8 g/L, 3.95 g/L, or 3.0 g/L poloxamer-188 all showed similar product stability (lanes 1, 2, and 3). The data also surprisingly show that the sample containing 6.8 g/L poloxamer-188 does not show substantial degradation after a 7-day incubation at room temperature, while the samples containing 3.0 g/L or 3.95 g/L poloxamer-188 both showed detectable degradation after the same incubation (FIG. 6; lanes 1*a*, 2*a*, and 3*a*). The data also demonstrate that addition of poloxamer-188 to a sample containing low poloxamer-188 does not improve product stability (FIG. 6; lanes 2*b* and 3*b*). These data show that the use of concentrations of poloxamer-188 that are greater than 1.8 g/L in the culture can reduce or inhibit degradation of recombinant proteins in the culture, and indicate that poloxamer-188 may be achieving this effect by providing for a healthier cell culture.

Example 3. Effect of Sparger Pore Type and Size on Amount of Poloxamer-188 Necessary to Achieve Beneficial Effect on Cell Culture Growth and Productivity A set of experiments was performed to test the effect of sparger pore type and size on the amount of poloxamer-188 necessary to achieve beneficial growth and productivity properties in a perfusion cell culture. In these experiments, different perfusion cell culture runs were performed using different spargers: a sparger having a sintered pore having a size of 20 μm (1 reactor); a sparger having a drilled pore having a size of 200 μm (2 reactors); or a sparger having a drilled pore having a size of 500 μm (1 reactor). Each perfusion culture initially used CD CHO medium containing 1.8 g/L poloxamer-188 and poloxamer-188 was added to the culture in increasing increments in order to maintain cell viability and minimize cell lysis as necessary. The viable cell density, the specific growth rate, the specific lactate dehydrogenase production rate, the percentage of viable cells, the volumetric productivity rate, and the aerobic glucose consumption for each cell culture was performed at different time points during the culture period using well-known methods.

Figure 7:
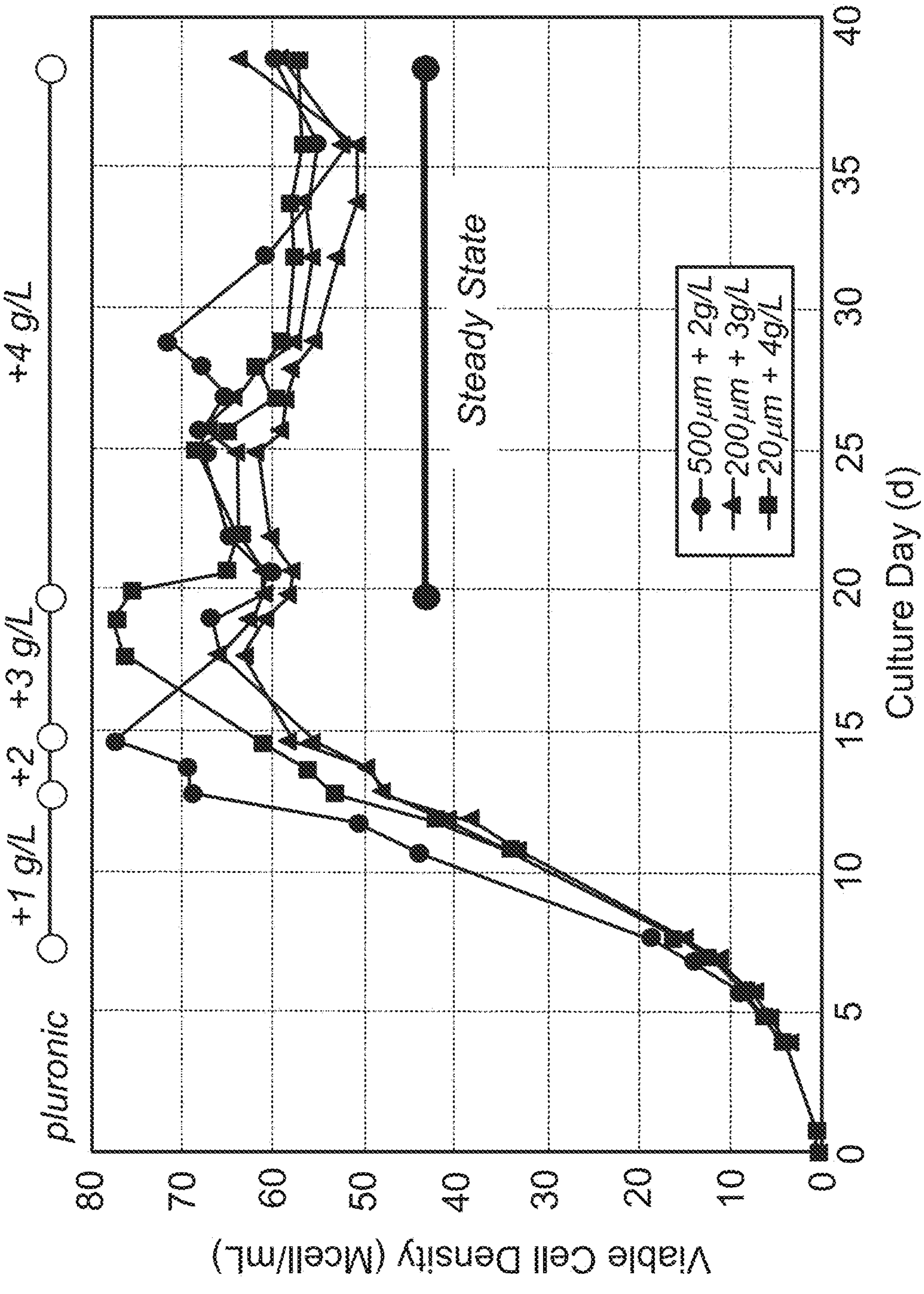
FIG. 7 is a graph of the viable cell density over time for a perfusion cell culture run performed using a sparger with a sintered pore having a size of 20 pin and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period) (triangles); and a perfusion cell culture run performed using a sparger with a drilled pore having a size of 500 μm and culture media that contain increasing amounts of poloxamer-188 over the length of the culture period (increasing from 1.8 g/L to 3.8 g/L) (circles).

The data show that a concentration of 3.8 g/L poloxamer-188 in the culture was able to maintain the viable cell density in the perfusion cell culture run performed using a sparger having a drilled pore having a size of 500 μm, a concentration of 4.8 g/L poloxamer-188 was able to maintain the viable cell density in the perfusion cell culture run performed using a sparger having a drilled pore having a size of 200 μm, and a concentration of 5.8 g/L poloxamer-188 was able to maintain the viable cell density in the perfusion cell culture run performed using a sparger having a sintered pore having a size of 20 μm (FIG. 7).

Figure 8:
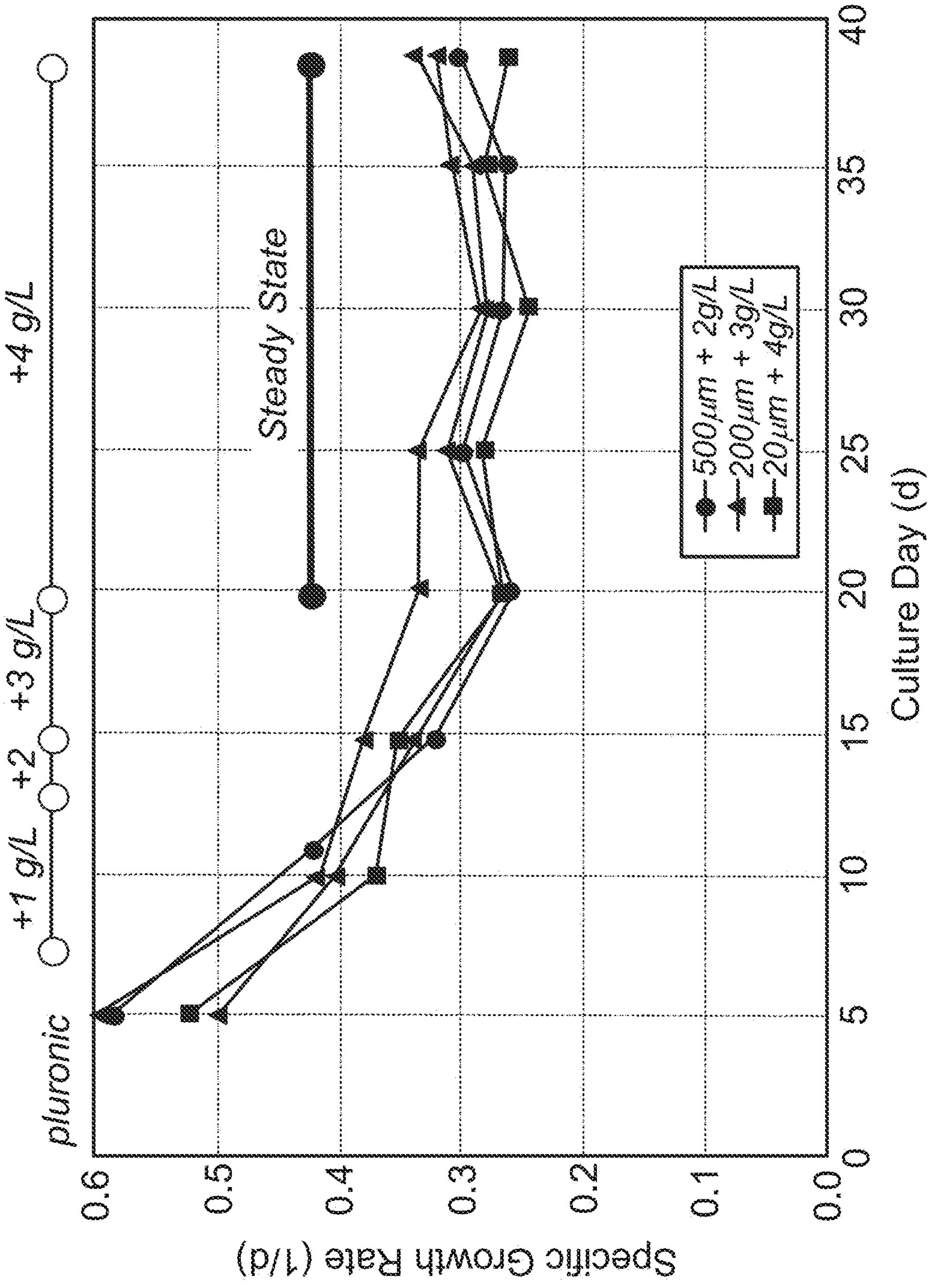
FIG. 8 is a graph of the specific growth rate over time for a perfusion cell culture run performed using a sparger with a sintered pore having a size of 20 pin and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period) (triangles); and a perfusion cell culture run performed using a sparger with a drilled pore having a size of 500 μm and culture media that contain increasing amounts of poloxamer-188 over the length of the culture period (increasing from 1.8 g/L to 3.8 g/L) (circles).
Figure 9:
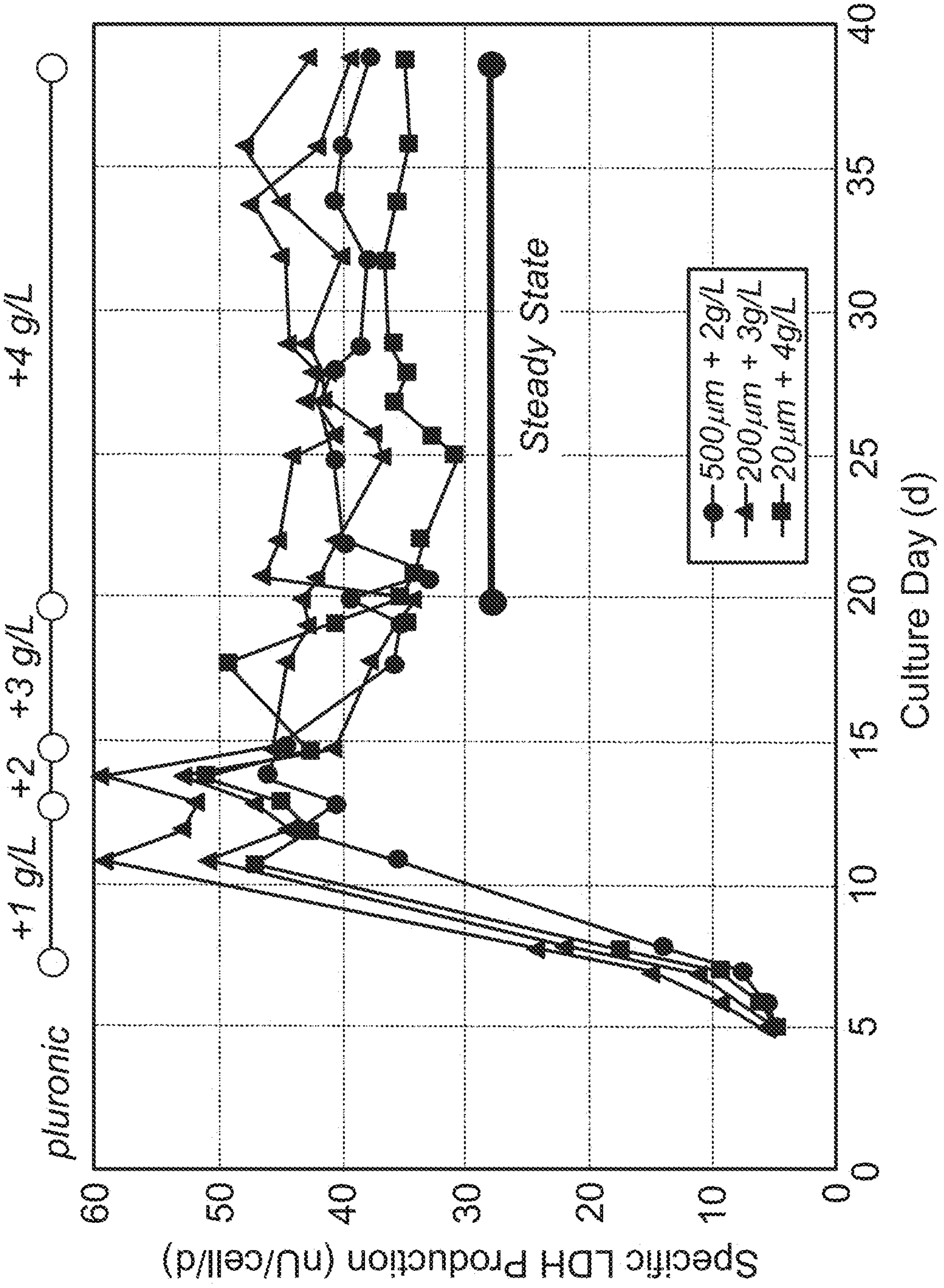
FIG. 9 is a graph of the specific lactose dehydrogenase production over time for a perfusion cell culture run performed using a sparger with a sintered pore having a size of 20 μm and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period) (triangles); and a perfusion cell culture run performed using a sparger with a drilled pore having a size of 500 μm and culture media that contain increasing amounts of poloxamer-188 over the length of the culture period (increasing from 1.8 g/L to 3.8 g/L) (circles).
Figure 10:
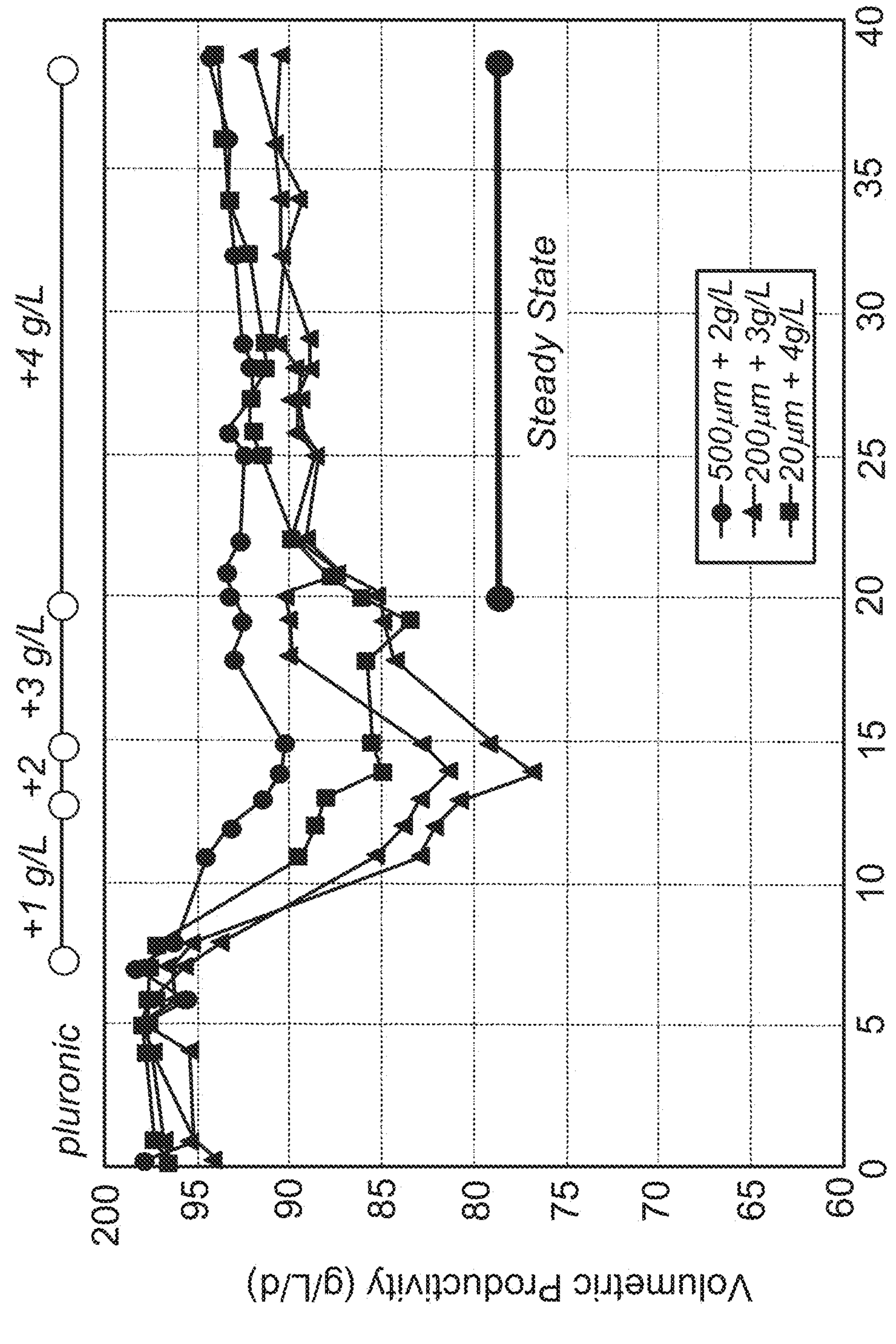
FIG. 10 is a graph of the percentage viable cells over time for a perfusion cell culture run performed using a sparger with a sintered pore having a size of 20 μm and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period) (triangles); and a perfusion cell culture run performed using a sparger with a drilled pore having a size of 500 μm and culture media that contain increasing amounts of poloxamer-188 over the length of the culture period (increasing from 1.8 g/L to 3.8 g/L) (circles).
Figure 11:
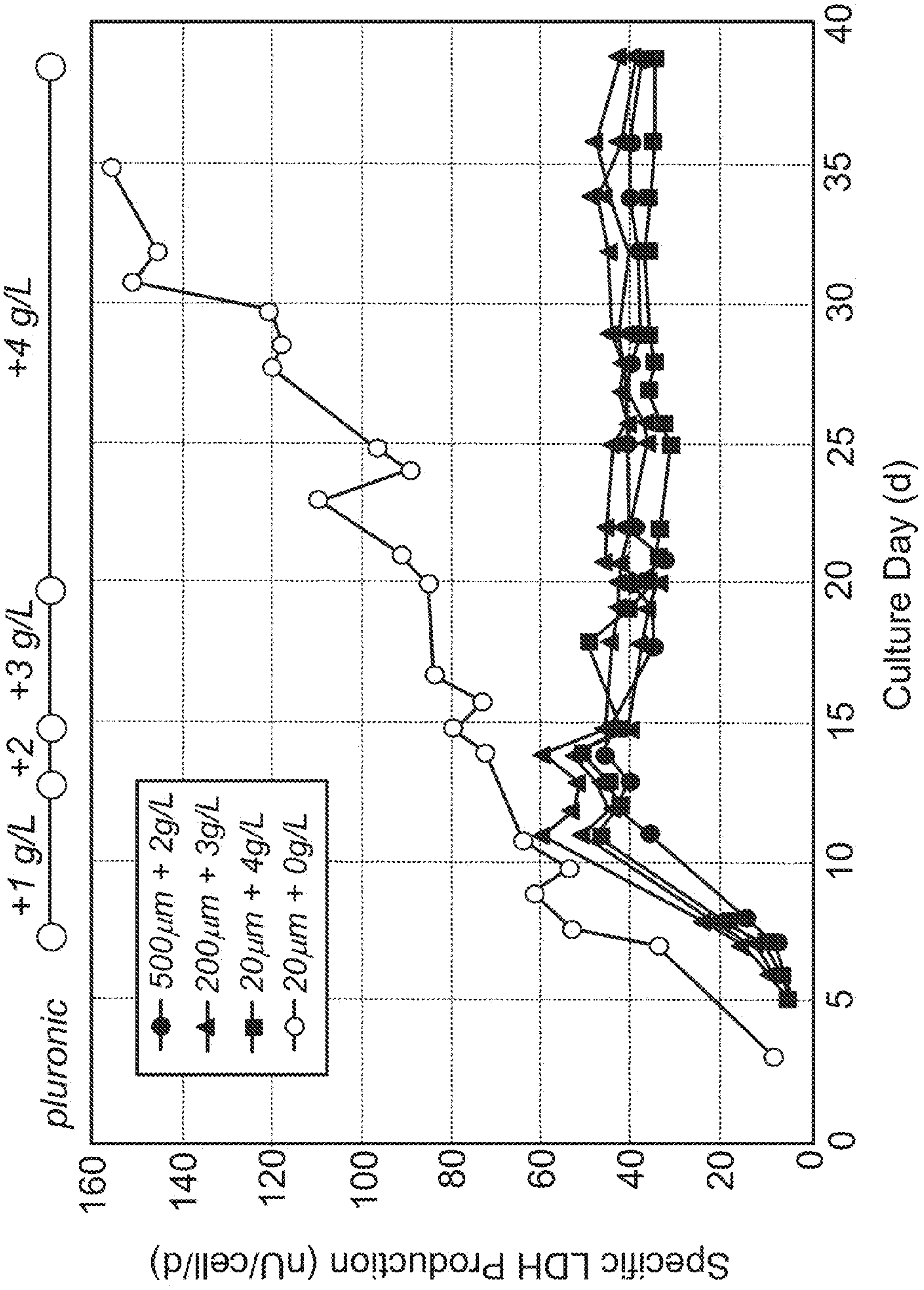
FIG. 11 is a graph of the specific lactose dehydrogenase production over time for a perfusion cell culture run performed using a sparger with a sintered pore having a size of 20 μm and culture media that contain 1.8 g/L poloxamer-188 over the length of the culture period (open circles); a perfusion cell culture run performed using a sparger with a sintered pore having a size of 20 μm and culture media that contain increasing amounts of poloxamer-188 over the length of the culture period (increasing from 1.8 g/L to 5.8 g/L poloxamer-188 over the length of the culture period) (squares); a perfusion cell culture run performed using a sparger with a drilled pore having a size of 200 μm and culture media that contain increasing amounts of poloxamer-188 over the length of the culture period (increasing from 1.8 g/L to 4.8 g/L over the length of the culture period)

The data also show that similar specific growth rates (FIG. 8), specific lactose dehydrogenase production rates (FIGS. 9 and 11), percentages of viable cells (FIG. 10), volumetric productivity rates (FIG. 12), and aerobic glucose consumption rates (FIG. 13) were achieved for the perfusion cell culture run performed using 3.8 g/L poloxamer-188 and a sparger having a drilled pore having a size of 500 μm, the perfusion cell culture run performed using 4.8 g/L poloxamer-188 and a sparger having a sintered pore having a size of 200 μm, and the perfusion cell culture run performed using 5.8 g/L poloxamer-188 and a sparger having a sintered pore having a size of 20 μm.

The data show that all the tested spargers can be used to achieve a viable cell density of $60\times10^6$ cells/mL, when poloxamer-188 is present in a concentration of greater than 1.8 g/L in the culture. For example, a viable cell density of greater than $60\times10^6$ cells/mL can be achieved in: a perfusion cell culture run using a sparger with a drilled pore having a size of 1 mm by using 2.8 g/L poloxamer-188 in the culture, a perfusion cell culture run using a sparger with a drilled pore having a size of 500 μm by using 3.8 g/L poloxamer-188 in the culture, a perfusion cell culture run using a sparger with a drilled pore having a size of 200 μm by using 4.8 g/L poloxamer-188 in the culture, a perfusion cell culture run using a sparger with a sintered pore having a size of 100 μm by using 3.8 g/L poloxamer-188 in the culture, and a perfusion culture using a sparger with a sintered pore having a size of 20 μm by using 5.8 g/L poloxamer-188 in the culture. The data indicate that the smaller the pore size, the more poloxamer-188 is required to maintain a healthy culture.

Example 4. Effect of Sparger Pore Type, Pore Size, and Antifoam to Poloxamer-188 Ratio on Perfusion Culture Cell Growth An additional set of experiments was performed to determine the steady-state cell growth in perfusion cultures using spargers with different pore types and sizes and different antifoam to poloxamer-188 ratios in the culture (shown in Table 1 below).

The data in Table 1 show that a smaller pore size requires that more antifoam-c needs to be added to the culture to mitigate the generation of foam, that additional antifoam-c is needed as the sparge rate increases, and that the optimal ratio of antifoam-c to poloxamer-188 may be between 0 and <5% (e.g., between about 1% to about 3%).

TABLE 1

Steady State Viable Cell Density Achieved for Tested Perfusion Cultures

| Exp | Sparger Type | Steady-State Viable Cell Density ($10e^6$ cells/mL) | Additional Pluronic (g/L) (CD-CHO = 1.8 g/L) | Antifoam Addition rate (ppm/day) | Antifoam addition to total pluronic ratio (%/day) | Sparge Rate (vol gas per min to volume of reactor) | Antifoam addition to sparge rate ratio (ppm) | Perfusion Rate (RV/day) |
|---|---|---|---|---|---|---|---|---|
| 2 | 20 μm drilled hole | 60 | 4 | 43 | 0.7 | 0.03 | 1 | 4 |
| 1 | 100 μm sintered | 110 | 4 | 160 | 2.8 | 0.43 | 0.26 | 6 |
| 2 | 200 μm drilled hole | 60 | 3 | 77-116 | 1.6-2.4 | 0.16-0.19 | 0.33-0.42 | 4 |
| 2 | 500 μm drilled hole | 60 | 2 | 69 | 1.8 | 0.15 | 0.32 | 4 |
| 1 | 1 mm drilled hole | 65 | 1 | 64 | 2.3 | 0.69 | 0.06 | 4 |

Example 5. Effect of Antifoam-C to Poloxamer-188 Ratio on Cell Growth in Batch Cell Culture Runs A set of experiments was performed to test the effect of antifoam-c to poloxamer-188 ratio on cell growth in a batch shake flask cell culture runs using CD-CHO medium containing 0% antifoam-c to poloxamer-188 ratio, a 5.6% antifoam-c to poloxamer-188 ratio, an 11.1% antifoam-c to poloxamer-188 ratio, a 27.8% antifoam-c to poloxamer-188 ratio, or a 55.6% antifoam-c to poloxamer-188 ratio. The shake flask cell cultures were baffled to passively generate bubbles to simulate a bioreactor. The viable cell density and specific lactate dehydrogenase production rate in each cell culture run were determined each day over the culture period using well-known methods.

The data show that lower antifoam-c to poloxamer-188 ratios demonstrate improved viable cell densities (FIG. 14) and lower specific lactate dehydrogenase production rates (FIG. 15). These data further suggest that the optimal ratio of antifoam-c to poloxamer-188 in a culture is between 0 and less than about 5% (e.g., between about 1% and about 3%).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of culturing a CHO cell in a liquid culture medium to achieve a viable cell density of greater than $60\times10^6$ cells/mL, the method comprising:

providing a culturing system comprising a vessel, a liquid culture medium disposed within the vessel, and a sparger disposed within the vessel comprising a plurality of pores configured to dispense gas through the sparger into the liquid culture medium; and perfusion culturing a CHO cell comprising a recombinant protein-encoding nucleic acid in the culturing system comprising the liquid culture medium comprising an amount of poloxamer-188 and antifoam under conditions and a gas flow rate sufficient to produce the recombinant protein in the system, wherein the ratio of antifoam (g/L) to poloxamer-188 (g/L) is about 1.0% to about 3.0% in the liquid culture medium, and wherein:

(i) the plurality of pores are drilled pores with a pore size of 900 μm to 1.1 mm and the poloxamer-188 concentration is 2.5 g/L to 3.1 g/L;

(ii) the plurality of pores are drilled pores with a pore size of 400 μm to 600 μm and the poloxamer-188 concentration is 3.5 g/L to 4.1 g/L;

(iii) the plurality of pores are drilled pores with a pore size of 1 μm to 250 μm and the poloxamer-188 concentration is 4.3 g/L to 8.0 g/L; or (iv) the plurality of pores are sintered pores with a pore size of 100 μm and the poloxamer-188 concentration is 5.8 g/L, and wherein the method results in a viable cell density in the liquid culture medium that is greater than $60\times10^6$ cells/mL.

2. The method of claim 1, wherein the plurality of pores are drilled pores with a pore size of 900 μm to 1.1 mm and the poloxamer-188 concentration is 2.5 g/L to 3.1 g/L.

3. The method of claim 1, wherein the plurality of pores are drilled pores with a pore size of 1 μm to 250 μm and the poloxamer-188 concentration is 4.3 g/L to 8.0 g/L.

4. The method of claim 1, wherein the plurality of pores are drilled pores with a pore size of 400 μm to 600 μm and the poloxamer-188 concentration is 3.5 g/L to 4.1 g/L.

5. The method of claim 1, wherein the plurality of pores are sintered pores with a pore size that is 100 μm and the poloxamer-188 concentration is 5.8 g/L.

* * * * *